United States Patent [19]

MacInnes et al.

[11] Patent Number: 6,019,984
[45] Date of Patent: Feb. 1, 2000

[54] BACTERIAL PREPARATIONS, METHOD FOR PRODUCING SAME, AND THEIR USE AS VACCINES

[75] Inventors: Janet MacInnes; Paul Ricciatti, both of Guelph; Bonnie Mallard, Ariss; Soren Rosendal, deceased, late of Guelph, all of Canada, by Lillian Rosendal, legal representative

[73] Assignee: University of Guelph, Guelph, Canada

[21] Appl. No.: 08/772,270

[22] Filed: Dec. 23, 1996

Related U.S. Application Data

[63] Continuation-in-part of application No. 08/396,244, Mar. 1, 1995, abandoned.

[51] Int. Cl.$^7$ ........................ A61K 39/102; A61K 39/02; A01N 63/00; C12N 1/00
[52] U.S. Cl. .................... 424/255.1; 424/93.4; 424/93.2; 424/93.48; 424/184.1; 424/278.1; 424/823; 424/824; 424/825; 424/826; 424/827; 424/828; 424/829; 435/243
[58] Field of Search ............................... 424/255.1, 93.4, 424/93.2, 93.48, 184.1, 278.1, 823–829; 435/243

[56] References Cited

FOREIGN PATENT DOCUMENTS

| | | |
|---|---|---|
| 1189790 | of 0000 | Canada . |
| 2040544 | of 0000 | Canada . |
| 2045950 | of 0000 | Canada . |
| A-420743 | of 0000 | European Pat. Off. . |
| WO93/08283 | of 0000 | WIPO . |
| WO93/21951 | of 0000 | WIPO . |

OTHER PUBLICATIONS

Anderson et al., Infect. Immun. 59:4110–4116, 1991.
Azad et al., J Gen. Microbiol. 138:1185–196, 1992.
Betsou, et al., Infection and Immunity. 61:3683–3589, 1993.
Bossé, et al., Can. J. Vet. Res. 54:320–325, 1990.
Braun and Focareta. Critic. Rev. Microbiol. 18:115–158, 1991.
Chang, et al., DNA 8:635–647, 1989.
Chang–Jo Lian, et al., Infect. Immun.57:3377–3382, 1989.
Chiang, et al., Vet. Microbiol. 27:49–62, 1991.
Conlon, et al., Infect. Immun. 59:587–591, 1991.
Deneer and Potter, Infect. Immun. 59:798–804, 1989.
Devenish, et al., Infect. Immun. 58:3829–3832, 1990.
Fedorka–Cray, P. J., 1989. *Actinobacillus (Haemophilous) pleuropneumoniae* virulence factors: Partial characterization and efficacy studies in swine. University of Nebraska, Ph.D. Thesis.
Fedorka–Cray, et al., Infect. Immun. 53:298–304, 1990.
Fenwick, et al., Infect. Immun. 53:298–304, 1986.
Fenwick and Osburn, Infect. Immun. 54:583–586, 1986.
Fenwick, et al., Am. J. Vet. Res. 47:1433–1441, 1986.
Fenwick and Osburn, Infect. Immun. 54:575–582, 1986.
Frey et al., in Bacterial Protein Toxins, Zbl.Bakt.Suppl. 24, In Freer et al. (Eds)., Gustav Fischer, Stuttgart, Jena, New York, 1994.
Frey, Res. Microbiol. 143:263–269, 1992.
Frey and Nicolet, 1988. FEMS Microbiol. Lett. 55:41–46, 1988.
Frey et al., Infect. Immun. 57:2050–2056, 1989.
Frey et al., J. Gen. Microbiol. 139:1723–1728, 1993.
Frey, et al., FEMS Microbiol. Let. 124:245–252, 1994.
Glisson and Cheng, Avian Dis. 35:392–396, 1991.
Gygi, et al. Mol. Microbiol. 4:123–128, 1990.
Hancock, ASM News. 57:175–182, 1991.
Heuther, et al., FEMS Microbiol. Let. 48:179–182, 1987.
Hirsch et al., Gene 48:203–209, 1986.
Inzana, et al Infect. Immun. 56:1880–1889, 1988.
Inzana, T.J., Infect. Immun. 55:1573–1579, 1987.
Inzana, et al., Micro. Path. 10:281–296, 1991.
Inzana, T. J., Microb. Path. 11:305–316, 1991.
Inzana and Mathison, Infect. Immun. 55:1580–1587, 1987.
Jansen, et al., Infect. Immun. 60:630–636, 1992.
Jansen, R., The RTX toxins of *Actinobacillus pleuropneumoniae*, Ph.D. thesis. DLO–Central Veterinary Institute, Lelystad, The Netheralands, 1994, pp. 111–131; Appendix to General Introduction.
Jensen and Bertran, Infect. Immun. 51:419–424, 1986.
Kamp, et al., Infect. Immun. 59:3079–3085, 1991.
Kamp, E. M et al., Veterinary Microbiology 13:249–257, 1987.
Koronakis, et al., J. Bacteriol. 169:1509–1515, 1987.
Korvuo, et al., Am. J. Vet. Res. 49:2072–2075, 1988.
Kume and Nakai, Jpn. J. Vet. Sci. 48:993–997, 1986.
Kume, et al., Infect. Immun. 51:563–570, 1986.
MacInnes and N.L. Smart, *Actinobacillus and Haemophilus*, In Pathogenesis of Bacterial Infections in Animals, 2nd ed. C.L. Gyles and C.O. Thoen, Iowa State University Press, Ames, Chapter 16.
MacInnes, et al., J. Bacteriol. 175:5633–5638, 1992.
MacInnes and Rosendal, Infect. Immun. 55:1626–1634, 1987.
MacInnes, et al., Can. J. Vet. Res. 54:244–250, 1990.
Martin, et al., Can. J. Vet. Res. 53:355–362, 1989.
Martin, et al., Can. J. Vet. Res. 31:456–462, 1985.
Maudsley, et al., Infect. Immun. 51:501–5–6, 1986.
Maudsley and Kadis. Can. J. Microbiol. 32:801–805, 1986.
Menestrina G., et al, Toxicology 87:249–267, 1994.
Mittal and Bourdon, J. Clin. Microbiol. 29:1344–1347, 1991.
Mosier et al., Infect. Immun. 57:711–716, 1989.
Nakai et al., Am. J. Vet. Res. 44:344–347, 1983.
Neilson, Nord. Vet. Med. 36:221–229, 1984.

(List continued on next page.)

*Primary Examiner*—Nita Minnifield
*Attorney, Agent, or Firm*—Bereskin & Parr

[57] ABSTRACT

Novel bacterial preparations containing one or more isolated and purified strain of a microorganism which produces one or more RTX toxins, and which strain has at least one RTX toxin which is substantially cell-associated. Methods of preparing the bacterial preparations and their use as vaccines and to produce antibodies for passive immunization are described.

23 Claims, 45 Drawing Sheets

OTHER PUBLICATIONS

Nielsen, R., et al. Vet. Scand. 27:453–455, 1986.
Nicolet, Can. Vet. J. 29:578–580, 1988.
Nicolet, J. 1992. *Actinobacillus pleuropneumoniae,* in Diseases of swine. 7th Ed. Ed. A. D. Lehman, B. E. Straw, W. L. Mengeling, S. D'Allaire, and D. J. Taylor, pp. 401–408. Ames: Iowa State University Press.
Nicolet et al., Arch. Tierheilkd. 113:1919–200, 1971.
Niven et al., Mol. Micro. 3:1083–1089, 1989.
O'Reilly et al., Vet. Microbiol. 29:159–172, 1991.
Perry et al., Serodiag. Immun. Inf. DIs. 4:299–308, 1990.
Pohl et al., Int. J. System. Bacteriol. 33:510–514, 1983.
Rapp and Ross, Can. Vet. J. 29:585–587, 1988.
Rosendal and MacInnes, Am. J. Vet. Res. 51:711–717, 1990.
Rosendal, et al., Vet. Microbiol. 12:229–240, 1986.
Rycroft and Taylor, Vet. Microbiol. 15:303–314, 1987.
Rycroft, et al., J. Gen. Microbiol. 137:561–568, 1991.
Setcavage and Kim Immunochem. 13:643–652, 1976.
Shewen, et al., Vet. Med. 83:1078–1083, 1988.
Shewen and Wilkie, Can. J. Vet. Res. 52:30–36, 1988.
Smits, et al., Infect. Immun. 59:4497–4504, 1991.
Strathdee and Lo, J. Bacteriol. 171:5955–5962, 1989.
Strathdee and Lo, J. Bacteriol. 171:916–928, 1989.
Thwaits and Kadis, Infect. Immun. 59:544–549, 1991.
Van den Bosch et al., 1992. Protection induced by a trivalent *A. pleuropneumoniae* subunit vaccine. abst. 194. Proceedings of the 12th International Pig Veterinary Society, The Hague, Netherlands.
van Leengoed, and Dickerson, Infect. Immun. 60:353–359, 1992.
Welch and Pellett, J. Bacteriol. 170:1622–1630, 1988.

Prior Art

SEQUENCES OF APXICA

| | |
|---|---|
| LOCUS | APAPXICA   3762 bp   DNA   circular   BCT      14-OCT-1993 |
| DEFINITION | A.pleuropneumoniae apxICA gene for RTX-toxins, serotype 9. |
| ACCESSION | X73117 |
| NID | g312897 |
| VERSION | X73117.1  GI:312897 |
| KEYWORDS | secreted protein; virulence marker. |
| SOURCE | Actinobacillus pleuropneumoniae. |
| ORGANISM | Actinobacillus pleuropneumoniae<br>Bacteria; Proteobacteria; gamma subdivision;<br>Pasteurellaceae; Actinobacillus. |
| REFERENCE | 1   (bases 1 to 3762) |
| AUTHORS | Jansen,R., Briaire,J., Kamp,E.M., Gielkens,A.L. and Smits,M.A. |
| TITLE | Structural analysis of the Actinobacillus pleuropneumoniae-RTX-toxin I (ApxI) operon |
| JOURNAL | Infect. Immun. 61 (9), 3688-3695 (1993)MEDLINE 93366425 |
| REFERENCE | 2   (bases 1 to 3762) |
| AUTHORS | Jansen,R. |
| TITLE | Direct Submission |
| JOURNAL | Submitted (01-JUN-1993) R. Jansen, DLO-Central Veterinary Institute, Postbox 65, 8200 AB Lelystad, NETHERLANDS |
| FEATURES | Location/Qualifiers |
| source | 1..3762<br>/organism="Actinobacillus pleuropneumoniae"<br>/sub_species="serotype 9"<br>/strain="13261" |

Figure 1(a)

```
                        /db_xref="taxon:715"
     gene               166..684
                        /gene="apxIC"
     CDS                166..684
                        /gene="apxIC"
                        /codon_start=1
                        /transl_table=11
                        /protein_id="CAA51547.1"
                        /db_xref="PID:g312898"
                        /db_xref="GI:312898"
                        /db_xref="SWISS-PROT:P55132"
/translation="MSKKINGFEVLGEVAWLWASSPLHRKWPLSLLAINVLPAIESNQYVLLKRDG
FPIAFCSWANLNLENEIKYLDDVASLVADDWTSGDRRWFIDWIAPFGDSAALYKHMRDNFPNELFR
AIRVDPDSRVGKISEFHGGKIDKKLASKIFQQYHFELMSELKNKQNFKFSLVNS"
     gene               694..3762
                        /gene="apxIA"
     CDS                694..3762
                        /gene="apxIA"
                        /codon_start=1
                        /transl_table=11
                        /protein_id="CAA51548.1"
                        /db_xref="PID:g312899"
                        /db_xref="GI:312899"
                        /db_xref="SWISS-PROT:P55128"
/translation="MANSQLDRVKGLIDSLNQHTKSAAKSGAGALKNGLGQVKQAGQKLILYIPKD
YQASTGSSLNDLVKAAEALGIEVHRSEKNGTALAKELFGTTEKLLGFSERGIALFAPQFDKLLNKN
QKLSKSLGGSSEALGQRLNKTQTALSALQSFLGTAIAGMDLDSLLRRRRNGEDVSGSELAKAGVDL
AAQLVDNIASATGTVDAFAEQLGKLGNALSNTRLSGLASKLNNLPDLSLAGPGFDAVSGILSVVSA
SFILSNKDADAGTKAAAGIEISTKILGNIGKAVSQYIIAQRVAAGLSTTAATGGLIGSVVALAISP
LSFLNVADKFERAKQLEQYSERFKKFGYEGDSLLASFYRETGAIEAALTTINSVLSAASAGVGAAA
TGSLVGAPVAALVSAITGIISGILDASKQAIFERVATKLANKIDEWEKKHGKNYFENGYDARHSAF
LEDTFELLSQYNKEYSVERVVAITQQRWDVNIGELAGITRKGSDTKSGKAYVDFFEEGKLLEKEPD
```

Figure 1(b)

RFDKKVFDPLEGKIDLSSINKTTLLKFVTPVFTAGEEIRERKQTGKYEYMTELFVKGKEKWVVTGV
QSHNAIYDYTNLIQLAIDKKGEKRQVTIESHLGEKNDRIYLSSGSSIVYAGNGHDVAYYDKTDTGY
LTFDGQSAQKAGEYIVTKELKADVKVLKEVVKTQDISVGKRSEKLEYRDYELSPFELGNGIRAKDE
LHSVEEIIGSNRKDKFFGSRFTDIFHGAKGDDEIYGNDGHDILYGDDGNDVIHGGDGNDHLVGGNG
NDRLIGGKGNNFLNGGDGDDELQVFEGQYNVLLGGAGNDILYGSDGTNLFDGGVGNDKIYGGLGKD
IYRYSKEYGRHIIIEKGGDDDTLLLSDLSFKDVGFIRIGDDLLVNKRIGGTLYYHEDYNGNALTIK
DWFKEGKEGQNNKIEKIVDKDGAYVLSQYLTELTAPGRGINYFNGLEEKLYYGEGYNALPQLRKDI
EQIISSTGAFTGDHGKVSVGSGGPLVYNNSANNVANSLSYSLAQAA"

```
BASE COUNT     1204 a    598 c    878 g   1082 t
ORIGIN
   1    agattaatga gcgatattgt tataaaatca taatgtaaac ctcatttgta
  51    atgaattggt aaattatata ataatcaaa  aaacttactt tttttattt
 101    ttatcggtaa gtatttacaa tcaagtcaga caaacggcaa tattgttata
 151    aatctggggg gatgaatgag taaaaaaatt aatggatttg aggttttagg
 201    agaggtggca tggttatggg caagttctcc tttacatcga aagtggccgc
 251    tttctttgtt agcaattaat gtgctacctg cgattgagag taatcaatat
 301    gttttgttaa agcgtgacgg ttttcctatt gcatttgta  gctgggcaaa
 351    tttgaatttg gaaaatgaaa ttaaatacct tgatgatgtt gcctcgctag
 401    ttgcggatga ttggacttcc ggcgatcgtc gatggtttat agattggata
 451    gcaccgttcg gagacagtgc cgcattatac aaacatatgc gagataactt
 501    cccgaatgag ctgtttaggg ctattcgagt tgatccggac tctcgagtag
 551    ggaaaatttc agaatttcat ggaggaaaaa ttgataagaa actggcaagt
 601    aaaattttc  aacaatatca ctttgaatta atgagtgagc taaaaaataa
 651    acaaaatttt aaattttcat tagtaaatag ctaaggagac aacatggcta
 701    actctcagct cgatagagtc aaaggattga ttgattcact taatcaacat
 751    acaaaaagtg cagctaaatc aggtgccggc gcattaaaaa atggtttggg
 801    acaggtgaag caagcagggc agaaattaat tttatatatt ccgaaagatt
 851    atcaagctag taccggctca agtcttaatg atttagtgaa agcggcggag
 901    gctttaggga tcgaagtaca tcgctcggaa aaaacggta  ccgcactagc
 951    gaaagaatta ttcggtacaa cggaaaaact attaggtttc tcggaacgag
1001    gcatcgcatt atttgcacct cagtttgata agttactgaa taagaaccaa
```

Figure 1(c)

```
1051 aaattaagta aatcgctcgg cggttcatcg gaagcattag gacaacgttt
1101 aaataaaacg caaacggcac tttcagcctt acaaagtttc ttaggtacgg
1151 ctattgcggg tatggatctt gatagcctgc ttcgtcgccg tagaaacggt
1201 gaggacgtca gtggttcgga attagctaaa gcaggtgtgg atctagccgc
1251 tcagttagtg gataacattg caagtgcaac gggtacggtg gatgcgtttg
1301 ccgaacaatt aggtaaattg ggcaatgcct tatctaacac tcgcttaagc
1351 ggtttagcaa gtaagttaaa taaccttcca gatttaagcc ttgcaggacc
1401 tgggtttgat gccgtatcag gtatcttatc tgttgtttcg gcttcattca
1451 ttttaagtaa taaagatgcc gatgcaggta caaaagcggc ggcaggtatt
1501 gaaatctcaa ctaaaatctt aggcaatatc ggtaaagcgg tttctcaata
1551 tattattgcg caacgtgtgg cggcaggctt atccacaact gcggcaaccg
1601 gtggtttaat cggttcggtc gtagcattag cgattagccc gctttcgttc
1651 ttaaatgttg cggataagtt tgaacgtgcg aaacagcttg aacaatattc
1701 ggagcgcttt aaaaagttcg gttatgaagg tgatagttta ttagcttcat
1751 tctaccgtga aaccggtgcg attgaagcgg cattaaccac gattaacagt
1801 gtgttaagtg cggcttccgc aggtgttggg gctgctgcaa ccggctcatt
1851 agtcggtgcg ccggtagcag ctttagttag tgcaatcacc ggtattattt
1901 caggtatttt agatgcttct aaacaggcaa tcttcgaacg agttgcaacg
1951 aaattagcga ataagattga cgaatgggag aaaaaacacg gtaaaaacta
2001 ttttgaaaac ggttatgacg cccgccattc cgcattctta aagatacct
2051 ttgaattgtt atcacaatac aataaagagt attcggtaga gcgtgtcgtt
2101 gctattacgc aacagcgttg ggatgtcaat atcggtgaac ttgccggcat
2151 tactcgcaaa ggttctgata cgaaaagcgg taaagcttac gttgatttct
2201 ttgaagaagg aaaacttta gagaagaac cggatcgttt tgataaaaaa
2251 gtgtttgatc cgcttgaagg taaaatcgac ctttcttcaa ttaacaaaac
2301 cactttattg aaatttgtta cgccggtctt taccgcaggt gaagagattc
2351 gtgagcgtaa gcaaaccggt aaatacgaat atatgaccga attattcgtt
2401 aaaggtaaag aaaaatgggt ggtaaccggt gtgcagtcac ataatgcgat
2451 ttatgactat acgaatctta tccaattagc gatagataaa aaaggtgaaa
2501 aacgtcaagt gaccattgaa tctcatttgg gtgagaaaaa tgatcgtata
2551 tatctttcat ccggttcatc tatcgtatat gcgggtaacg acatgatgt
2601 agcatattac gataaaaccg atacaggtta cttaacattt gacggacaaa
```

Figure 1(d)

```
2651 gtgcacagaa agccggtgaa tatattgtca ctaaagaact taaagctgat
2701 gtaaaagttt taaaagaagt ggttaaaact caggatattt cagttggaaa
2751 acgcagtgaa aaattagaat atcgtgatta tgagttaagc ccattcgaac
2801 ttgggaacgg tatcagagct aaagatgaat tacattctgt tgaagaaatt
2851 atcggtagta atcgtaaaga caaattcttt ggtagtcgct ttaccgatat
2901 tttccatggt gcgaaaggcg atgatgaaat ctacggtaat gacggccacg
2951 atatcttata cggagacgac ggtaatgatg taatccatgg cggtgacggt
3001 aacgaccatc ttgttggtgg taacggaaac gaccgattaa tcggcggaaa
3051 aggtaataat ttccttaatg gcggtgatgg tgacgatgag ttgcaggtct
3101 ttgagggtca atacaacgta ttattaggtg gtgcgggtaa tgacattctg
3151 tatggcagcg atggtactaa cttatttgac ggtggtgtag gcaatgacaa
3201 aatctacggt ggtttaggta aggatattta tcgctacagt aaggagtacg
3251 gtcgtcatat cattattgag aaaggcggtg atgatgatac gttattgtta
3301 tcggatctta gttttaaaga tgtaggattt atcagaatcg gtgatgatct
3351 tcttgtgaat aaaagaatcg gaggaacact gtattaccat gaagattaca
3401 atgggaatgc gctcacgatt aaagattggt tcaaggaagg taaagaagga
3451 caaaataata aaattgaaaa aatcgttgat aaagatggag cttatgtttt
3501 aagccaatat ctgactgaac tgacagctcc tggaagaggt atcaattact
3551 ttaatgggtt agaagaaaaa ttgtattatg gagaaggata taatgcactt
3601 cctcaactca gaaaagatat tgaacaaatc atttcatcta cgggtgcatt
3651 taccggtgat cacggaaaag tatctgtagg ctcaggcgga ccgttagtct
3701 ataataactc agctaacaat gtagcaaatt ctttgagtta ttctttagca
3751 caagcagctt aa
```

Figure 1(e)

SEQUENCES OF APXIBD

| | |
|---|---|
| LOCUS | APCLYI     5120 bp     DNA     BCT     01-DEC-1993 |
| DEFINITION | A.pleuropneumoniae clyIB and clyID genes. |
| ACCESSION | X61112 S66061 |
| NID | g38943 |
| VERSION | X61112.1 GI:38943 |
| KEYWORDS | clyIB gene; clyID gene; cytolysin. |
| SOURCE | Actinobacillus pleuropneumoniae. |
|   ORGANISM | Actinobacillus pleuropneumoniae |
| | Bacteria; Proteobacteria; gamma subdivision; |
| | Pasteurellaceae; |
| | Actinobacillus. |
| REFERENCE | 1   (bases 1 to 5120) |
|   AUTHORS | Smits,M.A. |
|   TITLE | Direct Submission |
|   JOURNAL | Submitted (31-JUL-1991) M.A. Smits, DLO-Central |
| | Veterinary Inst, |
| | Dept of Molecular Biology, Postbox 65, NL-8200-Ab |
| | Lelystad, THE NETHERLANDS |
| REFERENCE | 2   (bases 1 to 5120) |
|   AUTHORS | Smits,M.A., Briaire,J., Jansen,R., Smith,H.E., |
| | Kamp,E.M. and Gielkens,A.L. |
|   TITLE | Cytolysins of Actinobacillus pleuropneumoniae |
| | serotype 9 |
|   JOURNAL | Infect. Immun. 59 (12), 4497-4504 (1991) |
|   MEDLINE | 92040145 |
| COMMENT | See also X61111. |
| FEATURES | Location/Qualifiers |
|     source | 1..5120 |
| | /organism="Actinobacillus pleuropneumoniae" |
| | /strain="serotype 9" |

Figure 1B(a)

|  |  |
|---|---|
|  | /isolate="CVI 13261" |
|  | /db_xref="taxon:715" |
|  | /clone_lib="lambda Gem11" |
| -35_signal | 524..530 |
| -10_signal | 548..553 |
| terminator | 572..577 |
| RBS | 582..588 |
| gene | 592..2715 |
|  | /gene="clyIB" |
| CDS | 592..2715 |
|  | /gene="clyIB" |
|  | /codon_start=1 |
|  | /transl_table=11 |
|  | /product="ClyI-B protein" |
|  | /protein_id="CAA43425.1" |
|  | /db_xref="PID:g38944" |
|  | /db_xref="GI:38944" |
|  | /db_xref="SWISS-PROT:P26760" |

/translation="MDFYREEDYGLYALTILAQYHNIAVNPEELKHKFDLEGKGLDLTAWLLAAK
SLELKAKQVKKAIDRLAFIALPALVWREDGKHFILTKIDNEAKKYLIFDLETHNPRILEQAEFES
LYQGKLILVASRASIVGKLAKFDFTWFIPAVIKYRKIFIETLIVSIFLQIFALITPLFFQVVMDK
VLVHRGFSTLNVITVALAIVVLFEIVLNGLRTYIFAHSTSRIDVELGARLFRHLLALPISYFENR
RVGDTVARVRELDQIRNFLTGQALTSVLDLMFSFIFFAVMWYYSPKLTLVILGSLPFYMGWSIFI
SPILRRRLDEKFARGADNQSFLVESVTAINTIKALAVTPQMTNTWDKQLASYVSAGFRVTTLATI
GQQGVQFIQKVVMVITLWLGAHLVISGDLSIGQLIAFNMLSGQVIAPVIRLAQLWQDFQQVGISV
TRLGDVLNSPTESYQGKLALPEIKGDITFRNIRFYKPDAPVILNDVNLSIQQGEVIGIVGRSGS
GKSTLTKLIQRFYIPENGQVLIDGHDLALADPNWLRRQVGVVLQDNVLLNRSIRDNIALADPGMP
MEKIVHAAKLAGAHEFISELREGYNTIVGEQGAGLSGGQRQRIAIARALVNNPKILIFDEATSAL
DYESEHIIMRNMHQICKGRTVIIIAHRLSTVKNADRIIVMEKGQIV
EQGKHKELLADPNGLYHYLHQLQSE"

| RBS | 2713..2720 |

Figure 1B(b)

```
gene            2724..4160
                /gene="clyID"
CDS             2724..4160
                /gene="clyID"
                /codon_start=1
                /transl_table=11
                /product="ClyI-D protein"
                /protein_id="CAA43426.1"
                /db_xref="PID:g38945"
                /db_xref="GI:38945"
                /db_xref="SWISS-PROT:P26761"

/translation="MKTWLMGLYEFFQRYKTVWTEIWKIRHQLDTPDREKDENEFLPAHLELIET
PVSKKPRLIAYLIMLFLFLALVISIVSHVEIVATATGKLAFSDRSKEIKPIENALVKEIFVQDGQ
FVEKDQLLLHLTALGADADQQKTKSSLSLTKLERYRYEILLEAVAADRLPLIELTKDEFKHATEE
DKTRIRYLITEQFEAWQKQKYQKELALQRREAEKQTVLANIRKYEGISRVENERLKDLKKLFNSK
STSKHDVLTQENRHIEAVNELAVYKSRLNEVESDLRQAKEEIHLITQLFRADILEKLKQNVEAEK
QLSLELEKNEQRQIASVIRAPVSGTVQQLKTHTVGGVVTTAETLMVIAPEDDVLEVTALIQNKDI
GFIEVGQDAVIKVETFPYTRYGYLMGKVKNITLEAIEHPQLGLVFNSIISIDRKTLSGKDGKEIE
LGSGMSVTAEIKTGERSVISYLLSPLEESVSESLRER"
BASE COUNT      1580 a    880 c    1139 g    1521 t
ORIGIN
   1    tcgtcatatc attattgaga aaggcggtga tgatgatacg ttattgttat
  51    cggatcttag ttttaaagat gtaggattta tcagaatcgg tgatgatctt
 101    cttgtgaata aaagaatcgg aggaacactg tattaccatg aagattacaa
 151    tgggaatgcg ctcacgatta agattggtt caaggaaggt aaagaaggac
 201    aaaataataa aattgaaaaa atcgttgata agatggagc ttatgtttta
 251    agccaatatc tgactgaact gacagctcct ggaagaggta tcaattactt
 301    taatgggtta gaagaaaaat tgtattatgg agaaggatat aatgcacttc
 351    ctcaactcag aaaagatatt gaacaaatca tttcatctac gggtgcattt
 401    accggtgatc acggaaaagt atctgtaggc tcaggcggac gttagtcta
 451    taataactca gctaacaatg tagcaaattc tttgagttat tctttagcac
```

Figure 1B(c)

```
 501  aagcagctta agatagttat ttttagatga taaatagcaa tcctatatat
 551  attaggtgtg taggattgct attttattta tggaggagca aatggatttt
 601  tatcgggaag aagactacgg attatacgca ctgacgattt tagcccagta
 651  ccataatatt gctgtaaatc cggaagaact aaaacataaa ttcgaccttg
 701  aaggaaaagg cttagatcta accgcttggc tattagccgc aaaatcatta
 751  gaacttaaag caaacaagt aaaaaaagcg attgatcgtt tggcgtttat
 801  cgcactaccg gcacttgtat ggcgagaaga cggtaaacat tttattttga
 851  ctaaaattga taatgaagca aaaaaatatt taattttttga tttggaaacg
 901  cataatcctc gcatttggga acaagcggaa ttcgagagct ataccaagg
 951  aaaactgatt ttagttgcat caagagcttc catcgtaggt aagctggcaa
1001  agtttgactt cacttggttt ataccggcgg taattaagta tcgtaagatt
1051  tttattgaaa cgttaattgt ttcaatttt ttgcaaattt tcgcactaat
1101  tacaccgctt tttttccaag tcgtgatgga taaagtcttg gtacaccgag
1151  gttttcaac cttaaatgtg attacggtgg cattagcgat cgtcgtgctg
1201  tttgaaattg tgctaaacgg tttacgtacc tatattttg cgcatagtac
1251  cagccgtatt gatgtggagt tgggagcaag attattcaga catttattag
1301  cactcccaat ctcttatttt gaaaatcgtc gagtcggcga tacggtggct
1351  cgtgtacgag aactcgatca aattcgtaac ttcttaaccg ggcaggcact
1401  tacttccgtg ttggatttaa tgttttcctt tatcttcttt gcagtgatgt
1451  ggtattacag ccctaaactt actcttgtga ttttaggctc gttaccgttt
1501  tatatggggt ggtcgatttt tatcagccct attttacgtc gccgtttaga
1551  tgaaaaattc gcacgtggtg cggacaatca gtcattctta gtggaatcgg
1601  tgactgcaat caatacgatt aaagcgttgg cggttacccc tcaaatgact
1651  aatacctggg ataagcaatt agccagctat gtatcggcgg gattccgtgt
1701  aaccacatta gctactatcg gacagcaagg tgtacaattt attcaaaaag
1751  tcgtgatggt tattacctta tggctaggcg cacatttagt gatttcaggc
1801  gatttaagta tcggacaatt aatcgcattt aatatgttat ccggtcaagt
1851  gattgcaccg gtgattcgtt tagcgcaact ttggcaagat ttccaacaag
1901  tgggaatttc ggtaacgcgt ttaggtgatg ttttaaactc tccgaccgag
1951  agctatcaag gaaaattggc gttaccggaa attaaggcg atattacctt
2001  ccgtaatata cgcttccgct acaaaccgga tgcgccggtg attttaaatg
2051  atgtgaattt atcgattcag caaggtgaag tgatcggtat cgtaggacgt
```

Figure 1B(d)

```
2101 tcaggctcag ggaagagcac cttaacgaaa ttaattcaac gtttttatat
2151 tccggaaaac ggtcaggtat taatagatgg gcatgattta gcattggcgg
2201 atccgaactg gctacgtcgt caagtcgggg tggtattaca agataacgta
2251 ctattaaatc gtagtattcg agataatatt gccttagcgg atccgggtat
2301 gccaatggaa aaaattgtcc atgcggcaaa attagccggc gcacatgaat
2351 ttatttctga attgcgtgag ggatataaca cgattgttgg tgagcaaggt
2401 gcggggctat ctggcgggca acgccaacgt attgcgattg cacgcgcttt
2451 ggtgaataac ccgaaaatct taatttttga tgaagcgacc agcgcattag
2501 attatgaatc cgagcatatc atcatgcgca atatgcacca gatttgtaaa
2551 gggagaacgg taattatcat tgcacaccgt ttatctacgg taaaaaatgc
2601 cgaccgtatt attgtgatgg aaaaaggtca gattgtggaa caaggtaagc
2651 ataaagagct gcttgctgat ccaaacggct tatatcacta cttacaccaa
2701 ttacaatcgg aataggagga cttatgaaaa catggctaat gggtttatat
2751 gagttttttcc aacgctataa aacggtttgg acggagatct ggaaaattcg
2801 tcatcaattg gatacgccgg atcgagaaaa ggatgaaaat gaatttttac
2851 ctgcacactt agagctgatt gaaacaccgg tgtcaaaaaa accgagattg
2901 atcgcttatt taattatgct gttcctattt ttggcattag ttatttcaat
2951 tgtcagtcac gtagaaattg tggcgaccgc aacgggtaaa ttagcgttta
3001 gcgaccgtag caaagaaatt aagccgattg aaaacgcctt ggttaaagaa
3051 atctttgtgc aagacggaca atttgttgag aaagatcagt tgctgttaca
3101 cttgaccgca ttgggagccg atgcggatca acaaaaaacc aaaagttcgt
3151 tatcgctgac taaattggaa cgttatcgtt atgaaatttt attagaggcg
3201 gttgcggcgg ataggttgcc gctcattgaa ctgacaaagg atgaatttaa
3251 acatgctacg gaagaagata aaaccagaat tcgctatttg atcaccgagc
3301 aatttgaagc ttggcaaaag caaaagtatc aaaaagaatt agctttgcaa
3351 cgtagagaag cagaaaaaca aacggttcta gctaatattc gtaaatatga
3401 gggaatcagt cgagttgaaa atgaaagatt aaaagatctt aaaaaattat
3451 ttaattcgaa atcgacttct aaacatgatg tcttgactca agaaaatcgt
3501 catatcgaag cggtaaatga gttggcggtg tataaatctc ggttgaatga
3551 agtggaaagt gacttacgtc aagccaaaga ggaaatacat ttaataactc
3601 agttgtttag agccgatatt ctggagaagt tgaaacaaaa tgttgaagcg
3651 gagaaacagc tttcgctcga attagaaaaa aatgagcagc gtcaaattgc
```

Figure 1B(e)

```
3701 ttcggtgatt cgtgcgccgg tttccggtac ggttcagcaa cttaaaaccc
3751 atacggtagg cggcgtcgtg acgactgccg aaaccttgat ggtaattgct
3801 ccggaagatg atgttttaga ggtaacggcg ttaattcaaa ataaggatat
3851 cggttttatc gaggtcggtc aggatgcggt gattaaagta gaaacttttc
3901 cttatactcg ttacggctat ttaatgggta aagtaaaaaa tatcacgctg
3951 gaagccatcg aacatccgca actcggtcta gttttaact cgattatttc
4001 tattgataga aaactttat ccggcaaaga cggcaaagaa attgaacttg
4051 gatcaggtat gagtgtgacg gcggaaatta aaactggaga acgtagcgtt
4101 attagttatt tactcagtcc gttggaagaa tccgtttcgg agagtttaag
4151 agaacgctaa agcagataaa acaagcggcc atatttctt acttttttgc
4201 aaaaaacgta tgaaatatga ccgcttgtcg tttgtaaaag actatttatt
4251 tacaataatt ttagcaccgt tagaaaatac gatctgacga gcttcaaatt
4301 gagcggagag ctgtgcttgc gggtttagaa atacggcttg tgcttcttgc
4351 ggtaagtctg aaaccggtac gcaaaggcaa gttccgccgt ggtttggcgt
4401 tttaagttat ctttaaaggt aacgggcgca tcttgcgtga ggataacttt
4451 atcattgtaa acatagttta ccgcccattg aacgatacga atattgcgtt
4501 tggttttatt ttcaatactg tatttaaagc taaccatcgg ctgcccttct
4551 ttatttttag ccaattcata accgaaaaaa cgtaacccga tactgtcatt
4601 aaattgttta aggcgttttt ctttagccga aagaggtgca ttttcgtta
4651 ctgatttatg ttcaaccgtc ggttgaattt tattgccttc agcttgagca
4701 ttaaacgcta aaaagaatga tgctaccgcc gtgctaagta atttaatgtg
4751 tttcataatt cacctcgtaa tgagagctaa agccgactt gatatattac
4801 gctatatatt gtcagattta cggcacagtt gcaatgaccg cataaccgtc
4851 cgattcggca ataatctcga cttggctttc cgccgcaatg aaaatcgctt
4901 cgccttgttg gagataaatg gactcttcac cgaggtcgat atagatactg
4951 cctttcatca ccaataagat acttgcacag tcggccgtaa agttttcttc
5001 gtcaaatgcg ttgaattgca tatgttgcaa tgcaaaatct ttcgcttcag
5051 gcgtcggata aagatgaatg aaaccgtcgt tttcttgata aggcggaata
5101 acttcggggt aatcgggcga
```

Figure 1B(f)

Prior Art

SEQUENCES OF APXIICAB'

```
LOCUS       APCLY      4731 bp   DNA         BCT      21-JAN-1993
DEFINITION  A.pleuropneumoniae clyIIC, clyIIA and clyIIB genes.
ACCESSION   X61111 S66041 S66050
NID         g38939
VERSION     X61111.1  GI:38939
KEYWORDS    clyIIA gene; clyIIB gene; clyIIC gene; cytolysin.
SOURCE      Actinobacillus pleuropneumoniae.
  ORGANISM  Actinobacillus pleuropneumoniae
            Bacteria; Proteobacteria; gamma subdivision;
            Pasteurellaceae; Actinobacillus.
REFERENCE   1  (bases 1 to 4731)
  AUTHORS   Smits,M.A.
  TITLE     Direct Submission
  JOURNAL   Submitted (31-JUL-1991) M.A. Smits, DLO-Central
            Veterinary Inst,
            Dept of Molecular Biology, Postbox 65, NL-8200-Ab
            Lelystad, THE NETHERLANDS
REFERENCE   2  (bases 1 to 4731)
  AUTHORS   Smits,M.A., Briaire,J., Jansen,R., Smith,H.E.,
            Kamp,E.M. and Gielkens,A.L.
  TITLE     Cytolysins of Actinobacillus pleuropneumoniae serotype
            9
  JOURNAL   Infect. Immun. 59 (12), 4497-4504 (1991)
  MEDLINE   92040145
COMMENT     See also X61112.
FEATURES            Location/Qualifiers
     source         1..4731
                    /organism="Actinobacillus pleuropneumoniae"
                    /strain="serotype 9"
                    /isolate="CVI 13261"
```

Figure 2(a)

```
                    /db_xref="taxon:715"
/clone_lib="lambda Gem11"
        RBS             226..230
        gene            233..712
                        /gene="clyIIC"
        CDS             233..712
                        /gene="clyIIC"
                        /codon_start=1
                        /transl_table=11
                        /product="ClyII-C protein"
                        /protein_id="CAA43422.1"
                        /db_xref="PID:g38940"
                        /db_xref="GI:38940"
                        /db_xref="SWISS-PROT:P15376"

/translation="MLKNDFNVLGQIAWLWANSPMHRNWSVSLLMKNVIPAIENDQYLLLVDDGFP
IAYCSWAKLTLESEARYVKDTNSLKIDDWNAGDRIWIIDWIAPFGDSSLLYKHMRQRFPYDIGRAI
RIYPSKKDTGKIIYLKGGKITKKVAEKTFLQYEQELITALQ"
        RBS             738..743
        gene            751..3621
                        /gene="clyIIA"
        CDS             751..3621
                        /gene="clyIIA"
                        /codon_start=1
                        /transl_table=11
                        /product="ClyII-A protein   (cytolysin II)"
                        /protein_id="CAA43423.1"
                        /db_xref="PID:g38941"
                        /db_xref="GI:38941"
                        /db_xref="SWISS-PROT:P15377"

/translation="MSKITLSSLKSSLQQGLKNGKNKLNQAGTTLKNGLTQTGHSLQNGAKKLILY
```

Figure 2(b)

IPQGYDSGQGNGVQDLVKAANDLGIEVWREERSNLDIAKTSFDTTQKILGFTDRGIVLFAPQLDNL
LKKNPKIGNTLGSASSISQNIGKANTVLGGIQSILGSVLSGVNLNELLQNKDPNQLELAKAGLELT
NELVGNIASSVQTVDAFAEQISKLGSHLQNVKGLGGLSNKLQNLPDLGKASLGLDIISGLLSGASA
GLILADKEASTEKKAAAGVEFANQIIGNVTKAVSSYILAQRVASGLSSTGPVAALIASTVALAVSP
LSFLNVADKFKQADLIKSYSERFQKLGYDGDRLLADFHRETGTIDASVTTINTALAAISGGVGAAS
AGSLVGAPVALLVAGVTGLITTILEYSKQAMFEHVANKVHDRIVEWEKKHNKNYFEQGYDSRHLAD
LQDNMKFLINLNKELQAERVVAITQQRWDNQIGDLAAISRRTDKISSGKAYVDAFEEGQHQSYDSS
VQLDNKNGIINISNTNRKTQSVLFRTPLLTPGEENRERIQEGKNSYITKLHIQRVDSWTVTDGDAS
SSVDFTNVVQRIAVKFDDAGNIIESKDTKIIANLGAGNDNVFVGSSTTVIDGGDGHDRVHYSRGEY
GALVIDATAETEKGSYSVKRYVGDSKALHETIATHQTNVGNREEKIEYRREDDRFHTGYTVTDSLK
SVEEIIGSQFNDIFKGSQFDDVFHGGNGVDTIDGNDGDDHLFGGAGDDVIDGGNGNNFLVGGTGND
IISGGKDNDIYVHKTGDGNDSITDSGGQDKLAFSDVNLKDLTFKKVDSSLEIINQKGEKVRIGNWF
LEDDLASTVANYKATNDRKIEEIIGKGGERITSEQVDKLIKEGNNQISAEALSKVVNDYNTSKDRQ
NVSNSLAKLISSVGSFTSSSDFRNNLGTYVPSSIDVSNNIQLARAA"

```
    misc_binding    2905..3111
                    /gene="clyIIA"
                    /bound_moiety="Ca2+"
    terminator      3633..3666
                    /note="putative"
    RBS             3676..3682
    gene            3686..3739
                    /gene="clyIIB"
    CDS             3686..3739
                    /gene="clyIIB"
                    /codon_start=1
                    /transl_table=11
                    /product="truncated ClyII-B protein"
                    /protein_id="CAA43424.1"
                    /db_xref="PID:g38942"
                    /db_xref="GI:38942"
                    /translation="MEPNKNKDLGLAVENQT"
BASE COUNT      1577 a      787 c      921 g      1446 t
```

Figure 2(c)

```
ORIGIN
   1    cttaaccatt acagaacgtt ggtacaaaaa attttacagg aaaatgatgg
  51    atagtcctta acaaaaatta atgttttatt tcctataaaa catccgacca
 101    gtattatttt tgattaaaaa aagaacaaac agatcatgac aaacgtttgc
 151    cttgttttcc ttcacaaaaa tattatggtt ttttatttag aataaattat
 201    ctatattcat tttttaggga atgggaggga tgatgctaaa aaatgatttt
 251    aacgtattgg gacaaattgc ttggttatgg gcaaattctc caatgcaccg
 301    aaattggtca gtttcactgt taatgaagaa tgttattcct gcaattgaaa
 351    atgaccaata tttgttacta gttgatgatg gttttcctat tgcatattgc
 401    agttgggcca aattaactct agagagtgag gctcgctatg taaaggacac
 451    caattcatta aaaatagatg attggaatgc aggagatcgt atatggatca
 501    ttgattggat tgccccattc ggggattcat ctctattgta taacatatg
 551    agacaacgtt ttccatacga tattggaagg gcaattagaa tctatcctag
 601    caaaaaagat actggaaaaa tcatatattt aaaaggagga aaaataacaa
 651    aaaaagtagc tgaaaagaca tttcttcagt atgagcaaga gttaataaca
 701    gctctacaat aatatcttta aatgatcaat tatataagg agactctttt
 751    atgtcaaaaa tcactttgtc atcattaaaa tcgtccttac aacaaggatt
 801    gaaaatggg aaaaacaagt taaatcaagc aggtacaaca ctgaagaatg
 851    gtttaactca aactggtcat tctctacaga atgggctaa aaaattaatc
 901    ttatatattc ctcaaggcta tgattcgggt caaggaaatg gagttcaaga
 951    tttagttaaa gctgctaatg atttaggtat tgaagtatgg cgagaagaac
1001    gcagcaattt ggacattgca aaaactagct tgatacaac tcagaaaatt
1051    ctaggtttta ctgatagagg aattgtatta tttgcacctc agctagataa
1101    tttattaaag aagaatccta aaattggcaa tacattagga agtgcttcta
1151    gcatctcaca aaatataggt aaagccaata ctgtattagg tggtattcaa
1201    tctattttag gatctgtttt atctggagta aatctgaatg aattacttca
1251    aaataaagat cctaatcaat tagaacttgc aaaagcaggg ctagaactga
1301    ctaatgaatt agttggtaat attgctagct cggtgcaaac tgtagatgca
1351    tttgcagaac aaatatctaa actaggttca catttacaga atgtgaaagg
1401    attaggagga ttgagtaata aattacaaaa tctaccagat ctaggaaaag
1451    caagtttagg tttggacatt atctctggtt tactttctgg agcatctgca
1501    ggtctcattt tagcagataa agaggcttca acagaaaaga aagctgccgc
```

Figure 2(d)

1551 aggtgtagaa tttgctaacc aaattatagg taatgtaaca aaagcggtct
1601 catcttacat tcttgcccaa cgagtcgctt caggtttgtc ttcaactggt
1651 cctgtcgctg cattaatcgc atctacagtt gcactagctg ttagccctct
1701 ttcattctta aatgtagctg ataagtttaa acaagctgat ttaatcaaat
1751 catattctga acgcttccaa aaattaggat atgatggaga tcgtttatta
1801 gctgattttc accgtgagac aggaactatt gatgcttctg taacaacaat
1851 taacactgct ttagcagcta tctccggtgg agttggagct gcaagcgcgg
1901 gttctctagt cggagctcca gttgcgttac tcgttgctgg tgttacggga
1951 cttattacaa ctattctaga atattctaaa caagccatgt ttgaacatgt
2001 tgcaaataag gttcatgaca gaatagttga atgggagaaa aaacataata
2051 aaaactattt tgagcaaggt tatgattctc gtcatttagc tgatttacaa
2101 gacaatatga agtttcttat caatttaaat aaagaacttc aggctgaacg
2151 cgtagtagct attacccaac aaagatggga taaccaaatt ggagacctag
2201 cggcaattag ccgtagaacg gataaaattt ccagtggaaa agcttatgtg
2251 gatgcttttg aggaggggca acaccagtcc tacgattcat ccgtacagct
2301 agataacaaa aacggtatta ttaatattag taatacaaat agaaagacac
2351 aaagtgtttt attcagaact ccattactaa ctccaggtga agagaatcgg
2401 gaacgtattc aggaaggtaa aaattcttat attacaaaat tacatataca
2451 aagagttgac agttggactg taacagatgg tgatgctagc tcaagcgtag
2501 atttcactaa tgtagtacaa cgaatcgctg tgaaatttga tgatgcaggt
2551 aacattatag aatctaaaga tactaaaatt atcgcaaatt taggtgctgg
2601 taacgataat gtatttgttg ggtcaagtac taccgttatt gatggcgggg
2651 acggacatga tcgagttcac tacagtagag gagaatatgg cgcattagtt
2701 attgatgcta cagccgagac agaaaaaggc tcatattcag taaaacgcta
2751 tgtcggagac agtaaagcat tacatgaaac aattgccacc caccaaacaa
2801 atgttggtaa tcgtgaagaa aaaattgaat atcgtcgtga agatgatcgt
2851 tttcatactg gttatactgt gacggactca ctcaaatcag ttgaagagat
2901 cattggttca caatttaatg atatttcaa aggaagccaa tttgatgatg
2951 tgttccatgg tggtaatggt gtagacacta ttgatggtaa cgatggtgac
3001 gatcatttat ttggtggcgc aggcgatgat gttatcgatg gaggaaacgg
3051 taacaatttc cttgttggag gaaccggtaa tgatattatc tcgggaggta
3101 aagataatga tatttatgtc cataaaacag gcgatggaaa tgattctatt

Figure 2(e)

```
3151 acagactctg gcggacaaga taaactggca ttttcggatg taaatcttaa
3201 agacctcacc tttaagaaag tagattcttc tctcgaaatc attaatcaaa
3251 aaggagaaaa agttcgtatt gggaattggt tcttagaaga tgatttggct
3301 agcacagttg ctaactataa agctacgaat gaccgaaaaa ttgaggaaat
3351 tattggtaaa ggaggagaac gtattacatc agaacaagtt gataaactga
3401 ttaaggaggg taacaatcaa atctctgcag aagcattatc caaagttgtg
3451 aatgattaca atacgagtaa agatagacag aacgtatcta atagcttagc
3501 aaaattgatt tcttcagtcg ggagctttac gtcttcctca gactttagga
3551 ataatttagg aacatatgtt ccttcatcaa tagatgtctc gaataatatt
3601 caattagcta gagccgctta atattcaaat catagcaatc ctatggtgta
3651 aattatagga ttgttatttt tttaaaggag aagttatgga acccaataaa
3701 aataaggatc ttggtttagc tgtagaaaat caaacctaat ctgacagttc
3751 ccgtttaaaa ttaccgtgtc tgtcagatta atttgagctt aaattctttt
3801 ctgcccaaat ccgttttcca tcaagtaatg ttgccatcgg tgttctgcca
3851 cagcacactt ttccttgatg tgttcgatgg tgattataat acattcatct
3901 aaatcagctt gtaatgtcgc taaatccgta tatattttct tcctaaatgc
3951 gacttggtaa aattcttgta agatagtctt atgaaaacgt tcacagatac
4001 cattcgtctg tggatgcttc actttcgttt tagtatgctc tatgtcattt
4051 atcgctaaat aaagctcata atcgtgattt tccactttgc cacaatattc
4101 actgccacgg tcggtgagaa tacgcaacat cggtaatcct tgggcttcaa
4151 agaacggcag tactttatga ttgagcatat ctgcagcggc aattgcggtt
4201 ttcattgtgt agagctttgc aaaagcaacc ttactataag tatcaacaaa
4251 tgtttgctga taaatgcgtc caacaccttt taaattacct acataaaagg
4301 tatcttgtga acctaaatag cccggatgag cggtttcaat ttctccactc
4351 gatatatcat cctctttctt acgtctagg gcttggactt gactttcatt
4401 tagaataatg cctttctcag ccacttcttt ctctagtgca tttaaacgct
4451 gtttaaagtt agtaagatta tgacgtagcc aaatggaacg aacaccaccg
4501 gctgaaacaa acacaccttg cttgcgaagt tcgttactca ctcgaacttg
4551 tccgtaagct ggaaaatcta gagcaaattt tacaacagct tgctcaatgt
4501 gctcgtctac tcgattttg atattcggta cccgacgagt ttgcttaagt
4551 aatgcttcaa caccgccttg cgctacggct tgttgatagc gatagaatgt
4601 atctcggctc attcccatcg ctttacaagc t
```

Figure 2(f)

SEQUENCES OF APXIII

```
LOCUS       ACNNON    7721 bp   DNA         BCT     11-APR-1994
DEFINITION  Actinobacillus pleuropneumoniae (serotype 2) RTX
            toxin III (apxIII CABD) genes, complete cds.
ACCESSION   L12145
NID         g349605
VERSION     L12145.1  GI:349605
KEYWORDS    RTX toxin III.
SOURCE      Actinobacillus pleuropneumoniae 2 DNA.
  ORGANISM  Actinobacillus pleuropneumoniae 2
            Bacteria; Proteobacteria; gamma subdivision;
            Pasteurellaceae; Actinobacillus.
REFERENCE   1  (bases 1 to 7721)
  AUTHORS   Chang,Y.-f., Shi,J., Ma,D.-P., Shin,S.J. and
            Lein,D.H.
  TITLE     Molecular analysis of the Actinobacillus
            pleuropneumoniae RTX
            toxin-III gene cluster
  JOURNAL   DNA Cell Biol. 12, 351-362 (1993)
  MEDLINE   93263992
FEATURES             Location/Qualifiers
     source          1..7721
                     /organism="Actinobacillus pleuropneumoniae
                     2"
                     /db_xref="taxon:34063"
     promoter        152..157
     TATA_signal     173..178
     gene            195..733
                     /gene="apxIIIC"
     RBS             195..197
                     /gene="apxIIIC"
```

Figure 2B(a)

```
        CDS             212..733
        /gene="apxIIIC"
                        /codon_start=1
                        /transl_table=11
                        /product="RTX toxin"
                        /protein_id="AAA21923.1"
                        /db_xref="PID:g470684"
                        /db_xref="GI:470684"
```

/translation="MSYKNVKNLTDDFTTLGHIAWLWANSPLHKEWSISLFTKNILPAIQHDQYI
LLMRDEFPVAFCSWANLTLTNEVKYVRDVTSLTFEDWNSGERKWLIDWIAPFGDNNTLYRYMRKK
FPNEVFRAIRVYPGSTEAKIIHVQGGQINKFTAKKLIQQYQEELIQVLNNHKKIVRG"

```
        gene            727..3886
                        /gene="apxIIIA"
        RBS             727..730
                        /gene="apxIIIC"
        CDS             737..3886
                        /gene="apxIIIA"
                        /codon_start=1
                        /transl_table=11
                        /product="RTX toxin"
                        /protein_id="AAA21924.1"
                        /db_xref="PID:g470685"
                        /db_xref="GI:470685"
```

/translation="MSTWSSMLADLKKRAEEAKRQVKKGYDVTKNGLQYGVSQAKLQALAAGKAV
QKYGNKLVLVIPKEYDGSVGNGFFDLVKAAEELGIQVKYVNRNELEVAHKSLGTADQFLGLTERG
LTLFAPQLDQFLQKHSKISNVVGSSTGDAVSKLAKSQTIISGIQSVLGTVLAGINLNEAIISGGS
ELELAEAGVSLASELVSNIAKGTTTIDAFTTQIQNFGKLAENAKGLGGVGRQLQNISGSALSKTG
LGLDIISSLLSGVTRSFALRNKNASTSTKVAAGFELSNQVIGGITKAVSSYILAQRLRAGLSTTG
PAAALIASSISLAISPLAFLRVADNFNRSKEIGEFAERFKKLGYDGDKLLSEFYHEAGTIDASIT
TISTALSAIAAGTAAASAGALVGAPITLLVTGITGLISGILEFSKQPMLDHVASKIGNKIDEWEK

Figure 2B(b)

KYGKNYFENGYDARHKAFLEDSFSLLSSFNKQYETERAVLITQQRWDEYIGELAGITGKGDKLSS
GKAYVDYFQEGKLLEKKPDDFSKVVFDPTKGEIDISNSQTSTLLKFVTPLLTPGTESRERTQTGK
YEYITKLVVKGKDKWVVNGVKDKGAVYDYTNLIQHAHISSSVARGEEYREVRLVSHLGNGNDKVF
LAAGSAEIHAGEGHDVVYYDKTDTGLLVIDGTKATEQGRYSVTRELSGATKILREVIKNQKYAVG
KREETLEYRDYELTQSGNSNLKAHDELHSVEEIGSNQRDEFKGSKFRDIFHGADGDDLLNGNDGD
DILYGDKGNDELRGDNGNDQLYGGEGDDKLLGGNGNNYLSGGDGNDELQVLGNGFNVLRGGKGDD
KLYGSSGSDLLDGGEGNDYLEGGDGSDFYVYRSTSGNHTIYDQGKASDSDKLYLSDLSFDNILVK
RVNDNLEFRSNNNSNSGVLTIKDWFKGGNSYNHKIEQIVDKNGRKLTAGNLGNNFHDTQQASSLL
KNVTQEQNESNLSSLKTELGKIITNAGNFGVAKQGNTGINTAALNNEVNKIISSANTFATSQLGG
SGMGTLPSTNVNSMMLGNLARAA"

```
     stem_loop       3903..3935
     gene            3925..6078
                     /gene="apxIIIB"
     RBS             3925..3928
                     /gene="apxIIIB"
     CDS             3943..6078
                     /gene="apxIIIB"
                     /codon_start=1
                     /transl_table=11
                     /product="RTX toxin"
                     /protein_id="AAA21925.1"
                     /db_xref="PID:g470686"
                     /db_xref="GI:470686"
```

/translation="MESQMPFNEKIDYGLHALVILAQYHNVAVNPEEVKHKFDLDGKGLDLVAWL
LAAKSLELKVKRVKKSIERLPFIHLPALIWRDDGQHVILMKIDTQTNRYLIFDLEERNPKVLSAA
EFHEIFQGGMILITSRASIMGQLAKFDFTWFIPAVIKYRKIFVETIIVSIFLQLFALITPLFFQV
VMDKVLVHRGFSTLNVITVALSVVVIFEIVLSGLRTYIFSHSTSRIDVELGAKLFRHLLALPISY
FENRRVGDTVARVRELDQIRNFLTGQALTSVLDLLFSFIFFAVMWYYSPKLTIVILLSLPCYIAW
SIFISPILRRRLDEKFARNADNQSFLVESVSAIDTIKALAVTPQMTNIWDKQLASYVSADFRVTV
LATIGQQGVQLIQKTVMIINLWLGAHLVISGDLSIGQLITFNMLSGQVIAPVVRLAQLWQDFQQV
GISITRLGDVLNSPTENYQGKLSLPEIFGDIAFKHIRFRYKPDAPIILDDVNLSVKQGEVIGIVG

Figure 2B(c)

RSGSGKSTLTKLLQRFYIPENGQVLIDGHDLALADPNWLRRQIGVVLQDNVLLNRSIRDNIALTD
PSMSMERVIYAAKLAGAHDFISELREGYNTIVGELGAGLSGGQRQRIAIARALVNNPRILIFDEA
TSALDYESEHIIMQNMQKICHGRTVIIIAHRLSTVKNADRIIVMEKGHIVEQGKHNQLLENENGL
YYYLNQLQSN"

```
        gene            6090..7523
                        /gene="apxIIID"
        CDS             6090..7523
                        /gene="apxIIID"
                        /codon_start=1
                        /transl_table=11
                        /product="RTX toxin"
                        /protein_id="AAA21926.1"
                        /db_xref="PID:g470687"
                        /db_xref="GI:470687"
```

/translation="MKLWILGLGEFFQRYRNIWREIWKIRKQLDTPARQKDENEFLPRHLELIET
PISKKPRLIAYLIMLFLFLAIVISIISKVEIVASATGKLVFSGHSKEIKPIENALVKDIFVKDGQ
FVEKGQLLLNLTALGCDADKQKTKVSLGLERLDGYRYKSLLYSIEHNRLPLLDFNQADFDSVQEE
DKTGARHLITEQFETWQKQKYQKELAYQRKQAEKQTVLANIRKYESASRIEKEKLSDLKKLYDVK
SISKHELLAQENRYVEASNELSVYQSHLKEVESDLLKAQEDLKLVTQLFKSDILEKLQQNIQREK
QLTLELEKNEQRQLASIIRAPVSGTVQQLKTHTKGGVVTTAETLMVIAPEDDVLEVSALIQNKDV
GFVEIGQEAVIKVETFPYTRYGYLYGKVKTITLDAIEHPQLGLVFNSIIEINKKTLTDGDKEIQL
GSGMSVIAEIKTGERSVISFLLSPLEESITESLRER"

```
        stem_loop       7580..7615
BASE COUNT     2593 a   1146 c   1520 g   2462 t
ORIGIN
1       tcttgaataa tagttggttt tgtagatatt cttttaatat caaacaacta
51      ttgttatttg tctgagtgta gatatgtagc attgtgtatt tctttattta
101     caactctaat cttaatctaa aaagatttct atatttctt  tgtaagaaat
151     tttgttaaaa tccgactaac tatataatta acggttctta aagtggataa
201     ataataaaat tatgagttat aaaaatgtta aaaatttaac agatgatttt
251     acaactttag ggcatatcgc ttggttgtgg gctaattctc cgttacataa
```

Figure 2B(d)

```
301   ggagtggtct atctctttgt ttactaagaa tattttgcca gccattcaac
351   atgatcaata tattttactt atgcgagatg agttccctgt agcgttttgt
401   agttgggcaa atttaacgtt aactaatgaa gtgaagtatg tacgtgatgt
451   gacgtcattg acttttgaag attggaattc aggagaacga aaatggttga
501   tcgattggat tgcgccattt ggggataaca atacgcttta tagatatatg
551   cgtaaaaaat ttcctaatga agtattccgg gccattcgag tatatcctgg
601   ttctacagaa gcgaaaatca ttcatgttca aggaggacaa attaataaat
651   ttacagctaa aaaattaata caacaatatc aggaagaact tattcaagtt
701   cttaacaatc acaaaaaaat tgtaagagga taaaatatga gtacttggtc
751   aagcatgtta gccgacttaa aaaaagggc tgaagaagcc aaaagacaag
801   ttaaaaaagg ctacgatgta actaaaaatg gtttgcaata tggggtgagt
851   caagcaaaat tacaagcatt agcagctggt aaagccgttc aaaagtacgg
901   taataaatta gttttagtta ttccaaaaga gtatgacgga agtgttggta
951   acggtttctt tgatttagta aaagcagctg aggaattagg cattcaagtt
1001  aaatatgtta accgtaatga attggaagtt gcccataaaa gtttaggtac
1051  cgcagaccaa ttcttgggtt taacagaacg tggacttact ttatttgcac
1101  cgcaactaga tcagttctta caaaaacatt caaaaatttc taacgtagtg
1151  ggcagttcta ctggtgatgc agtaagtaaa cttgctaaga gtcaaactat
1201  tatttcagga attcaatctg tattaggtac tgtattagca ggtattaatc
1251  ttaatgaagc tattattagt ggcggttcag agctcgaatt agctgaagct
1301  ggtgtttctt tagcctctga gctcgttagc aatattgcta aaggtacaac
1351  aacaatagat gctttcacta cacaaatcca gaactttggg aaattagcgg
1401  aaaatgctaa agggttaggt ggtgttggcc gccaattaca gaatatttca
1451  ggttctgcat taagcaaaac tggattaggt ttggatatta tctcaagctt
1501  actttcagga gtaactcgaa gttttgcttt acggaataag aatgcttcaa
1551  caagcactaa agttgctgct ggctttgaac tctcaaatca gtaattggt
1601  ggtattacga aagcagtatc aagctatatt cttgcacagc gtttacgtgc
1651  tggtttatca acgacaggtc ctgctgcagc actaattgcg tctagtattt
1701  ctttagcaat cagtccattg gcgttttac gtgtagctga taattttaat
1751  cgttctaaag aaattggcga atttgctgaa cgtttcaaaa aattgggcta
1801  tgacggcgat aaactacttt cagagtttta tcacgaagct ggtactattg
1851  atgcctcaat tactacaatt agtacagcac tttctgctat cgcagctgga
```

Figure 2B(e)

```
1901 acggccgccg cgagtgcagg tgcattagtt ggcgcaccaa ttactttgtt
1951 ggttactggt atcacaggat taatttctgg tattttagag ttctctaaac
2001 aaccaatgtt agatcatgtt gcatcgaaaa ttggtaacaa aattgacgaa
2051 tgggagaaaa atacggtaa  aaattacttc gagaatggct atgatgctcg
2101 tcataaagct ttcttagaag attcattctc attattgtct agttttaata
2151 aacaatatga aactgaaaga gctgttttaa ttacacaaca acgttgggat
2201 gaatatattg gcgaacttgc gggtattact ggtaaaggtg acaaactctc
2251 tagtggtaag gcgtatgtag attactttca agaaggtaaa ttattagaga
2301 aaaaacctga tgactttagc aaagtagttt tcgatccaac taagggcgaa
2351 attgatattt caaatagcca acgtcaacg  ttgttaaaat ttgttacgcc
2401 attattaaca ccaggtacag agtcacgtga agaactcaa  acaggtaaat
2451 atgaatatat cacgaagtta gttgtaaaag gtaaagataa atggttgtt
2501 aatggcgtta aagataaagg tgccgtttat gattatacta atttaattca
2551 acatgctcat attagttcat cagtagcacg tggtgaagaa taccgtgaag
2601 ttcgtttggt atctcatcta ggcaatggta atgacaaagt gttcttagct
2651 gcgggttccg cagaaattca cgctggtgaa ggtcatgatg tggtttatta
2701 tgataaaacc gatacaggtc ttttagtaat tgatggaacc aaagcgactg
2751 aacaagggcg ttattctgtt acgcgcgaat tgagtggtgc tacaaaaatc
2801 ctgagagaag taataaaaaa tcaaaaatat gctgttggta aacgtgaaga
2851 aaccttggaa tatcgtgatt atgaattaac gcaatcaggt aatagtaacc
2901 taaaagcaca tgatgaatta cattcagtag aagaaattgg aagtaatcag
2951 agagacgaat ttaaaggtag taaattcaga gatattttcc atggtgccga
3001 tggtgatgat ctattaaatg gtaatgatgg ggatgatatt ctatacggtg
3051 ataaaggtaa cgatgagtta agaggtgata acggtaacga ccaactttat
3101 ggtggtgaag gtgatgacaa actattagga ggtaatggca ataattacct
3151 cagtggtggt gatggcaatg atgagcttca agtattaggc aatggtttta
3201 atgtgcttcg tggcggtaaa ggcgatgata aactttatgg tagctcaggt
3251 tctgatttac ttgatggtgg agaaggtaat gattatctag aaggaggcga
3301 tggtagcgat ttttatgttt atcgttccac ttcaggtaat catactattt
3351 atgatcaagg taaagctagc gattcagata agctatattt gtcagatctt
3401 tcttttgata atatttagt  taaaagggtt aacgataacc ttgagtttag
3451 aagcaataat aacagtaata gtggtgtgct tacgatcaag gactggttca
```

Figure 2B(f)

```
3501 aaggcggcaa tagttacaat cataaaattg aacaaattgt tgataaaaat
3551 ggtagaaaat tgacagctgg gaatttagga ataacttcc atgatactca
3601 acaagctagt agtttactta aaatgttac acaagaacaa aatgaaagca
3651 atttatcttc acttaaaact gaattaggta aaattattac taatgcaggt
3701 aattttggtg tggcaaaaca aggtaatact ggaatcaata cagctgcctt
3751 gaacaatgaa gtgaataaaa tcatttcttc tgctaatacc tttgctactt
3801 cacaattggg tggctcaggg atgggaacat taccatcaac gaatgtaaat
3851 tcaatgatgc taggtaacct agctagagca gcttaatcat ctgcaataat
3901 caatagcaat cctatggtta ttctaggatt gctattttat ttatggagtc
3951 acaaatgcct tttaacgaaa aaatagatta cggattacat gcattggtaa
4001 ttctcgcgca atatcacaat gttgccgtaa accctgaaga ggtaaaacat
4051 aaatttgatc ttgatggcaa aggattggat cttgttgctt ggttattagc
4101 agcaaaatca ttagaattaa aagtcaaacg agtaaaaaag agtattgagc
4151 gtttaccatt tattcatctt cctgctttaa tctggcgaga tgatggtcaa
4201 cacgttattt tgatgaaaat tgacacccaa actaaccgtt accttatttt
4251 tgacttagaa gaacgaaacc ctaaagtact aagtgcggct gaatttcacg
4301 aaattttca aggtggtatg attcttatta cttcacgagc ttctattatg
4351 gggcaattgg cgaagtttga tttcacttgg tttatccccg cagtaattaa
4401 ataccgtaaa attttgtag aaactattat tgtttctatt ttttgcagc
4451 ttttgcact aattactccc ttattttcc aagttgtgat ggataaagtt
4501 cttgtccatc gtggattttc tacacttaat gttatcacgg ttgcattatc
4551 tgtagtggtt atctttgaaa ttgtattaag cggtctacgg acttatatat
4601 tttcccatag cactagccga attgatgtag aacttggtgc aaaattattt
4651 cgtcacttgt tagcgttacc tatttcttat ttcgaaaata gacgtgtagg
4701 tgacacagtt gctcgagtac gagaattgga tcaaatacgc aatttttaa
4751 caggtcaggc acttacctct gtattagatc tcttattctc ttttatttc
4801 tttgcagtga tgtggtatta cagcccaaaa ctaactattg tgattttact
4851 ttcattacct tgttatatcg catggtcaat atttattagc ccaatattac
4901 gtcgtcgtct agatgaaaaa tttgctcgta atgctgataa tcaatctttt
4951 ttagttgaat ctgtttctgc aatagacacg atcaaggctc ttgctgtaac
5001 acctcaaatg acaaatattt gggataaaca gttagcaagt tatgtatcag
5051 cagattttag agtgacagta ttggcaacta ttggacagca aggtgtacaa
```

Figure 2B(g)

```
5101 cttatccaaa aaacagtaat gataattaat ttatggttag gtgcacattt
5151 agtaatttca ggggatctta gcattggaca attaattact tttaatatgc
5201 tttcaggaca agttattgca cctgtagttc gtttagcaca attgtggcaa
5251 gactttcaac aagtaggaat ttctattaca cgattgggag atgtcttaaa
5301 ttacctaca gaaaattatc aaggtaagct ttcactacca gaaatctttg
5351 gggatatcgc atttaaacat attcgctttc gctataagcc cgatgctcca
5401 atcattttag atgatgtaaa tttatcggtt aaacaggggg aagttattgg
5451 gatagtagga cgttcaggtt caggtaaaag tactctcact aaattattac
5501 aacgttttta tattccggaa aatggccaag tattgattga tggtcacgat
5551 cttgcgcttg ctgatcctaa ttggttacgt cgtcaaattg gtgttgtttt
5601 acaagataat gtgttattaa accgtagtat tcgcgataat atcgcactca
5651 ctgatccaag catgtctatg gaacgtgtta tctatgcggc aaaattagca
5701 ggggcacatg attttatttc tgaattacgt gaaggttaca atactattgt
5751 aggagagctt ggtgcaggct tatctggtgg acaacgtcaa cggattgcta
5801 ttgcacgagc tttagtcaat aaccctagga ttttgatttt tgatgaggcg
5851 acaagtgcat tagattatga atctgaacat atcattatgc aaaatatgca
5901 aaaaatctgc catggacgga cagtaatcat tattgcccac cgtctttcta
5951 cagtaaaaaa tgcggatcgc attattgtta tggaaaaggg acatattgta
6001 gagcaaggta aacataacca attactggaa aatgaaaatg gactctatta
6051 ttacctcaac caactacaat caaattaagg tgaaacaaca tgaagttatg
6101 gattctagga cttggggaat tttttcaacg ttatcgtaat atttggcgtg
6151 aaatatggaa aatccgcaaa caattagata ccccagcaag acaaaaagat
6201 gaaaacgaat ttttgcctcg gcatttagag ttaattgaga cacctatttc
6251 aaaaaagcca cggctgatcg cttatttgat aatgctattt ctattttag
6301 ctattgtaat ttccattatt agtaaagtag aaattgttgc tagtgctaca
6351 ggtaagttgg tatttagtgg acatagtaaa gaaataaagc ctattgagaa
6401 tgctttagta aaagacattt ttgttaaaga tggacaattt gttgaaaaag
6451 gacaattatt attaaatctc accgcacttg gctgcgatgc agacaaacaa
6501 aaaactaaag tatcgttagg attggaaaga ttagatggtt accgatataa
6551 gtcattgtta tatagcattg aacacaatag attacctta ttggattta
6601 accaagctga ttttgattct gttcaggaag aagataagac tggcgcacgt
6651 catttaatta ccgaacaatt tgagacttgg caaaaacaaa aatatcagaa
```

Figure 2B(h)

```
6701 ggaattagcg tatcaacgta aacaagctga aaaacaaaca gtattagcaa
6751 atatccgtaa atatgaaagc gctagtcgta ttgaaaagga gaaattaagt
6801 gatttaaaaa aattatatga tgtaaagtct atttctaagc atgagttgtt
6851 agcacaagaa aatagatatg ttgaagctag taatgaattg tctgtttatc
6901 aatctcatct caaagaagta gaaagtgact tgcttaaagc acaagaagat
6951 ttaaagcttg ttactcaatt atttaagagt gatattttgg aaaaactaca
7001 gcaaaatata caacgcgaaa agcagctcac tttagaactt gagaaaaatg
7051 aacaacgtca attagcctct atcattaggg cgccagtatc aggcacagtc
7101 caacaattaa aaactcatac taaaggtggc gtagtaacta ctgcagaaac
7151 cttaatggtc attgctcctg aggatgacgt gttggaagta agtgctttaa
7201 ttcaaaacaa agatgttggt tttgttgaaa ttggacagga agcagttatt
7251 aaagtggaaa cttttcccta cacaagatat ggttatctct atggaaaagt
7301 aaaaactatt actcttgatg ctattgagca ccctcagctt ggtttagttt
7351 tcaattctat tattgagatt aacaagaaaa cattaacaga tggtgataaa
7401 gaaattcaat taggttctgg aatgagcgtt attgcagaaa ttaaaacagg
7451 agaacgcagt gttatcagtt tcctactcag tccattagaa gaatctatta
7501 ctgaaagtct aagagaacgt taattatctc ttctaaatta agcaaatata
7551 taactttgt aaaaacgtta tttaaggaga gttgctaata gaagttaaaa
7601 tatctattag caactatatt atctctttga gctattttta gcttctttag
7651 aagttagaga ttttagata ttcataatat atgaaactat ttgctgatct
7701 aatttaaaac taaaatctag a
```

BACTERIAL PREPARATIONS, METHOD FOR PRODUCING SAME, AND THEIR USE AS VACCINES

The present application is a continuation in part application of U.S. patent application Ser. No. 08/396,244 filed on Mar. 1, 1995 now abandoned.

FIELD OF THE INVENTION

The invention relates to novel bacterial preparations, methods for producing the preparations, and the use of the preparations as vaccines and to prepare antibodies.

BACKGROUND OF THE INVENTION

A family of toxins, referred to as the Repeats in Toxins (RTX), have been associated with infections caused by gram-negative organisms including *E. coli*, Proteus, Morganella, Pasteurelia, Actinobacillus, and Bordetella spp. (Menestrina G., et al, Toxicology 87 (1994) 249–267, and references referred to therein). The prototype toxin is *Escherichia coli* α-hemolysin which is a primary virulence factor of urinary infections, peritonitis, meningitis, and septicemia caused by virulent strains of *E. coli*. The RTX toxins share several common features which are discussed in the review by Welch, Mol. Microbiol. 5, 521, 1991.

The RTX toxins of *Actinobacillus pleuropneumoniae* play an important role in infections cause by strains of *Actinobacillus pleuropneumoniae* (J. Frey et al., in Bacterial Protein Toxins, Zbl.Bakt. Suppl. 24, Freer et al. (Eds)., Gustav Fischer, Stuttgart, Jena, N.Y., 1994). *Actinobacillus pleuropneumoniae* is the agent responsible for swine pleuropneumonia, a severe contagious disease which causes great economic losses (J. I. MacInnes and N. L Smart, Actinobacillus and Haemophilus in Pathogenesis of Bacterial Infections in Animals, 2nd ed. C. L. Gyles and C. O. Thoen, Iowa State University Press, Ames, Chapter 16). *A. pleuropneumoniae* is a gram-negative bacterium of the family Pasteurellaceae J. I. MacInnes and N. L Smart, supra). Twelve serotypes of the organism have been described by serotyping based on capsular polysaccharides (Nicolet, J. Can. Vet. J. 29:578–580, 1988 and Nielsen, R., cta. Vet. Scand. 27:453–455, 1986). Differences in virulence have been observed among the serotypes and a number of virulence factors have been considered responsible for the differences. These factors include capsular polysaccharides, liposaccharides, exotoxins and adhesion factors (J. I. MacInnes and N. L Smart, supra).

Two hemolytic RTX toxins, ApxI and ApXII, and one non-hemolytic RTX toxin, ApxIII have been identified in different *A. pleuropneumoniae* serotype strains J. Frey et al., supra) The toxins are secreted into the growth medium by *A. pleuropneumoniae*, they have different molecular masses, and they can be distinguished serologically by polyclonal and monoclonal antibodies (J. Frey et al., supra). It has been reported that *A. pleuropneumoniae* serotypes which produce a combination of two Apx toxins are more virulent than serotypes with one toxin alone (J. Frey et al., supra). The serotypes producing ApxI and ApxII are the most virulent (J. Frey et al., supra). No *A. pleuropneumoniae* strains have been identified which produce all three toxins J. Frey et al., supra).

RTX toxins have also been reported to be secreted in other bacterial strains including *Bordetella pertussis* (Betsou et al.1993 and CA 1,189,790) *E. coli*, Listeria, Moraxella, Pseudomonas, Staphylococcus, Vibrio (Nakai et al. 1983) and *Neisseria meningitidis* (Thompson et al.1993).

Vaccines which have been developed for preventing infections by *A. pleuropneumoniae* have been based on whole live cells, attenuated cells, lysates, culture supernatants, and extracts of *A. pleuropneumoniae*. Canadian Patent 1,189,790 describes a vaccine containing *A. pleuropneumoniae* cells, cell fragments, extracts and/or metabolites, and an adjuvant derived from *Bordetella pertussis*. Other proposed vaccines contain: (a) inactivated toxin of serotype I and optionally a toxin of another serotype (EP-A-420.743); (b) whole cell or sonicated whole cell components of a virulent strain obtained after passage in a host (WO9321951-A); (c) transferring binding protein, cytolysin and/or APP4 (WO9308283-A); (d) at least one immunogenic part of at least one cytolytic *A. pleuropneumoniae* protein prepared by recombinant DNA methods (Canadian Patent Application 2,045,950); (e) an iron-repressible outer membrane protein of molecular weight 105 kD (Canadian Patent Application 2,045,950); (f) outer membrane proteins having a major dominant antigenic protein component of 42 kD and a haemolysin of 105 kD and/or macrophage toxin of 120 kD (Canadian Patent Application No. 2,040,544); (g) inactivated toxin of serotype 1 of *A. pleuropneumoniae* which is obtained from culture supernatant (EP-420743); (h) extracellular proteinaceous materials from the culture medium of strains of at least two different serotypes of *A. pleuropneumoniae*. (EP-420743); or, (i) hemolysin antigen produced by recombinant techniques. Many of the known vaccines have limited effectiveness particularly against infection by heterologous serotypes.

Conventional formalin-killed bacterins provide limited protection against challenge with homologous serotypes of *A. pleuropneumoniae* and poor protection against heterologous serotypes (Neilson, 1984). In contrast, convalescent pigs are completely protected from challenge with homologous serotypes and significantly protected from disease from heterologous serotypes (Neilson, 1984).

Many of the antigenic components of *A. pleuropneumoniae* which have been investigated as potential vaccine candidates all fall short of affording complete cross-protection. Devenish et al. (1990) demonstrated homologous protection from challenge when gel-purified ApxI and ApxII cytolysins were used as a vaccine. However, others have reported less than complete protection with partially purified toxin vaccines, although the protection afforded is increased when these vaccines are enriched with other cellular components such as outer membrane proteins (OMPs) (Van den Bosch et al., 1992).

Live attenuated vaccines made from strains of *A. pleuropneumoniae* lacking in capsule production have been reported to protect against homologous challenge (Rosendal et al., 1990; Inzana et al., 1988). Results have not been reported with heterologous challenge. Live strains deficient in RTX toxin production have been reported to afford no protection against disease (Inzana et al., 1991). Jansen (1994) has concluded that both opsonization of *A. pleuropneumoniae* to enhance phagocytosis and neutralization of the RTX toxins are necessary for immune protection against disease.

SUMMARY OF THE INVENTION

The present inventors observed significant quantities of cell-associated RTX toxins when strains of *A. pleuropneumoniae* that are capable of producing RTX toxins, are cultured under certain conditions. Further, the whole cell protein composition of the cultures was found to substantially correspond to the whole cell protein profiles obtained from in vivo cells recovered at necropsy from the pleural fluid of infected swine. Thus, the in vitro preparation obtained by the present inventors mimicked the profiles of organisms from the lungs of swine exhibiting cross-protective immunity.

Vaccination with a bacterin prepared from heat-inactivated cultures having significant quantities of cell-associated RTX toxins, and adjuvanted with a double adjuvant system, resulted in significant protection of swine against challenge with homologous strains. Lung scores were found to be similar to those of a low-dose challenge group that were fully protected from disease. In contrast, there was 100% mortality in swine vaccinated with a commercial bacterin.

Broadly stated the present invention relates to a bacterial preparation comprising one or more isolated and purified strain of a microorganism which produces one or more RTX toxins, and which strain has at least one RTX toxin which is substantially cell-associated. Preferably, the microorganism is a pathogenic gram negative bacteria, particularly from the family Pasteurellaceae or Enterobacteriaceae. Most preferably, the microorganism is *A. pleuropneumoniae, A. actinomycetemcomitans, A. suis, A. equuli, Pasteurella haemolytica, Escherichia coli, Proteus vulgaris, Proteus mirabilis, Morganella morganii,* or *Bordetella pertussis.*

In an embodiment of the invention, a bacterial preparation is provided comprising one or more isolated and purified strain of the same or different serotype of *A. pleuropneumoniae* which has one or more of ApxI, ApxII and ApxIII which are substantially cell-associated. In a preferred embodiment, the bacterial preparation comprises two or more isolated and purified strains of different serotypes of *A. pleuropneumoniae* which collectively have ApxI, ApxII and ApxIII which are substantially cell-associated.

The present invention also relates to methods for preparing the bacterial preparations of the invention. In one embodiment of the invention, a method is provided for preparing a bacterial preparation comprising selecting one or more strain of a microorganism which produces one or more RTX toxins; culturing the selected strain under suitable conditions so that the RTX toxin is substantially cell-associated.

In another embodiment of the invention, a bacterial preparation of the invention is prepared by selecting one or more strain of a microorganism which produces one or more RTX toxins, and treating the strain with a substance which interferes with the secretion of the RTX toxins.

The bacterial preparations of the invention may also be prepared by producing, using gene transfer techniques, a strain of a microorganism which has cell-associated RTX toxins.

The bacterial preparations of the invention may be used as vaccines for the prophylaxis and treatment of infectious diseases caused by strains of microorganisms which produce one or more RTX toxins. The bacterial preparations of the invention may also be used to prepare antibodies which may be used as a means of passive immunization.

The invention also relates to a method of preparing a vaccine against infectious diseases caused by a strain of a microorganism which produces one or more RTX toxins which comprises selecting a bacterial preparation which contains one or more of the strain of the microorganism, and which strain has at least one RTX toxin which is substantially cell-associated.

These and other aspects of the present invention will become evident upon reference to the following detailed description and attached drawings. In addition, reference is made herein to various publications, which are hereby incorporated by reference in their entirety. For ease of reference, a list of abbreviations, and the full citations of some of the publications cited and incorporated herein by reference, listed in alphabetical order by author, follow the Examples in the Detailed Description of the Invention.

DESCRIPTION OF THE DRAWINGS

The invention will be better understood with reference to the drawings in which:

FIG. 1 as depicted in FIGS. 1(*a*), 1(*b*), 1(*c*), 1(*d*) and 1(*e*), shows the nucleotide sequence of apxICA genes and the deduced amino acid sequences of ApxIC and ApxIA from GeEMBL Accession X73117;

FIG. 1B, as depicted in FIGS. 1B(*a*), 1B(*b*), 1B(*c*), 1B(*d*), 1B(*e*) and 1B(*f*), shows the nucleotide sequence of the apxIBD genes and the deduced amino acid sequences of ApxIB and ApxID from GenEMBL Accession X61112;

FIG. 2 as depicted in FIGS. 2(*a*), 2(*b*), 2(*c*), 2(*d*), 2(*e*) and 2(*f*), shows the nucleotide sequence of the apxIIA, apxIIB', and apxIIC genes and the deduced amino acid sequences of ApxIIA, ApxIIB, and ApxIIC from GenEMBL Accession X61111;

FIG. 2B as depicted in FIGS. 2B(*a*), 2B(*b*), 2B(*c*), 2B(*d*), 2B(*e*), 2B(*f*), 2B(*g*), 2B(*h*) and 2B(*i*), shows the nucleotide sequence of the apxIIIA, apxIIIB, apxIIIC, and apxIIID genes, and the deduced amino acid sequence of ApxIIIC; ApxIIIA, ApxIIIB, and ApxIIID from GenEMBL Accession L12145;

FIG. 5A shows Western blots of WC proteins of *A. pleuropneumoniae* serotype 1 grown in various media probed with sera from a pig exposed to low-dose challenge of *A. pleuropneumoniae* CM5;

FIG. 5B shows Western blots of WC proteins of *A. pleuropneumoniae* serotype 1 grown in various media probed with sera from a pig hyperimmunized with purified cytolysin from CM5;

FIG. 5C shows Western blots of WC proteins of *A. pleuropneumoniae* serotype 1 grown in various media probed with sera from a pig immunized with commercial bacterin;

FIG. 11A shows Western blots of WC proteins of *A. pleuropneumoniae* probed with serum from a pig hyperimmunized with gel-purified CYT;

FIG. 11B shows Western blots of WC proteins of *A. pleuropneumoniae* probed with serum from a pig exposed to low-dose challenge;

DETAILED DESCRIPTION OF THE INVENTION

I. Characterization of the Bacterial Preparations

The bacterial preparations of the invention comprise one or more isolated and purified strains of a microorganism which produces one or more RTX toxins, and which strains have at least one RTX toxin which is substantially cell-associated. The preparations may additionally contain one or more strains of a different microorganism which produces one or more RTX toxins.

The microorganisms used in the preparations of the invention are selected from pathogenic Gram negative bacteria, particularly from the family Pasteurellaceae, such as *A. pleuropneumoniae, P. haemolytica, Actinobacillus suis*, and *Actinobacillus actinomycetemcomitans*. Other microorganisms which may be used in the preparations of the invention include *Bordetella pertussis* and microorganisms from the family Enterobacteriaceae including *E. coli, Proteus mirabilis, Proteus vulgaris*, and *Morganella morganii*, (Chang et al, 1989; Devenish et al, 1989; Gygi et al, 1990; Frey et al, 1993; Smits et al, 1991; Jansen et al, 1992).

The strains of the microorganism present in the bacterial preparations of the invention may be reference strains which may be obtained from researchers working in the field or from public depositories such as the American Type Culture Collection, Bethesda, Md. Serotype reference strains of *A. pleuropneumoniae* are described below. The strains may also be obtained from animals suffering from naturally occurring infections, they may be naturally-occurring mutant strains, or strains produced using gene transfer techniques. It will be appreciated that attenuated strains may be selected or produced for use in the bacterial preparations. The microorganism may be classified into strains or particular serotypes using generally known methods. For example, the classification of strains of *A. pleuropneumoniae* into particular serotypes is provided in Veterinary Microbiology 13 (1987), pages 249–257).

"RTX toxins" used herein refers to toxins of the family of homologous cytotoxins and exoproteins of which *E. coli* hemolysin (HlyA) is the prototype. RTX toxins are characterized by their ability to lyse target cells. The lytic activity is $Ca^{2+}$ dependent and is caused by a colloid osmotic shock due to the formation of hydrophilic pores in the membranes of the target cells. The designation RTX for "repeats in toxin" is based on the presence in the cytolytic product of homologous glycine-rich repeat domains responsible for $Ca^{2+}$ dependent binding to target cells and expression of lytic activity.

Figure 3:
FIG. 3 shows the arrangement of the operon of the genes encoding the Apx toxins of the 12 reference serotypes of *A.pleuropneumoniae* from J. Frey et al., in Bacterial Protein Toxins, Zbl.Bakt. Suppl. 24, Freer et al. (Eds)., Gustav Fischer, Stuttgart, Jena, N.Y., 1994, FIG. 1.

RTX toxins are also generally characterized by the organization of their operon. The operon generally consists of the following four genes: an activator gene (designated "C"), a structural toxin gene (designated "A"), and two secretion genes (designated "BD"). The four genes are typically arranged in the order CABD. The genetic arrangement of the genes encoding the Apx toxins of the 12 reference serotypes of *A. pleuropneumoniae* is shown in FIG. 3B. The gene profile and distribution may differ in different strains and some strains may not contain certain of the genes, for example the secretion genes.

The RTX toxins may also be characterized on the basis that they are secreted as an active toxin by the proteins encoded by the hemolysin BD genes of *E. coli*. RTX toxins also include toxins which have substantial sequence homology to known RTX toxins, in particular homologs of *E. coli* hemolysin (HlyA).

The RTX toxins have different target-cell specificities (Welch, 1991). For example, *A. pleuropneumoniae* cytolysins ApxI and ApxII hemolyse erythrocytes from pig, sheep, bovine and human and are cytolytic to porcine and rabbit neutrophils and porcine alveolar macrophages. Whereas the leukotoxin from *P. haemolytica* is specific for ruminant leukocytes.

Examples of RTX toxins are the ApxI, ApxII, and ApxIII toxins of *A. pleuropneumoniae*. ApxI, also known as hemolysin I or cytolysin I is strongly hemolytic and has an apparent molecular mass of 105 kDa (J. Frey et al., 1994a). Serotypes 1, 5a, 5b, 9, 10 and 11 of *A. pleuropneumonia* produce ApxI (J. Frey et al., 1994a). The structural apxIA gene contains three strongly hydrophobic domains and a domain with 13 glycine rich repeat nonapeptides J. Frey et al., 1994a). ApxI shows strong similarities to the *Escherichia coli* hemolysin and to a lesser extent to the *Pasteurella haemolytica* leukotoxin (J. Frey et al., 1994a). apxI contains the activator gene apxIC and the structural gene apxIA (J. Frey et al., 1994a). FIG. 1 shows the nudeotide sequence of the apxICA genes and the deduced amino acid sequences of ApxIC and ApxIA. FIG. 1B shows the nucleotide sequence of the apxIBD genes and the deduced amino acid sequences of ApxIB and ApxID. The nucleotide sequence of the apxICA genes is also shown in the Sequence Listing as SEQ.

ID. NO. 3, and the deduced amino acid sequences of ApxIC and ApxIA are shown in the Sequence Listing as SEQ. ID. NOS. 1 and 2, respectively. The nudeotide sequence of the apxIB and apxID genes, and the deduced amino acid sequences of ApxIB and ApxID are shown in the Sequence Listing as SEQ. ID. NOS. 6, 4, and 5, respectively.

ApxII, also known as hemolysin II or cytolysin II, is a weakly hemolytic and weakly cytotoxic RTX-toxin which is produced by all serotypes of *A. pleuropneumoniae* except serotype 10 (J. Frey et al., 1994a). ApxII provides weak hemolytic character to serotypes which do not simultaneously produce ApxI (J. Frey et al., 1994a). ApxII has an apparent molecular weight by SDS gel electrophoresis of 103 kDa (J. Frey et al., 1994a). The structural gene for ApxII contains three strongly hydrophobic domains and a domain with 8 glycine rich repeated nonapeptides. ApxII is closely related to the *Pasteurella haemolytica* leukotoxin. FIG. 2 shows the nucleotide sequence of the apxIIA, apxIIB', and apxIIC genes and the deduced amino acid sequences of ApxIIA, ApxIIB, and ApxIIC. The nudeotide sequences of the apxIIA, apxIIB', and apxIIC genes, and the deduced amino acid sequences of ApxIIA, and ApxIIC, are also shown in the Sequence Listing as SEQ. ID. NOS. 9, 8, and 7, respectively.

ApxIII, also known as pleurotoxin or cytolysin III is non-hemolytic but strongly cytotoxic for alveolar macrophages and neutrophils (J. Frey et al., 1994a). ApxIII is produced by serotypes 2, 3, 4, 6, and 8. Its apparent molecular weight by SDS gel electrophoresis is 120 kDa (J. Frey et al., 1994a). The ApxIII gene contains three strongly hydrophilic domains and a region with 13 glycine rich repeat. The amino acid sequence of ApxIII deduced from the DNA sequence shows identity to APxI, ApxII, *E. coli* hemolysin and *P. haemolytica* leukotoxin (J. Frey et al., 1994a). FIG. 2B shows the nucleotide sequence of the apxIIIA, apxIIIB, apxIIIC, and apxIIID genes, and the deduced amino acid sequence of ApxIIIC, ApxIIIA, ApxIIIB, and ApxIIID. The nucleotide sequence of the apxIIIA, apxIIIB, apxIIIC, and apxIIID genes, and the deduced amino acid sequences of ApxIIIC, ApxIIIA, ApxIIIB, and ApxIIID, are also shown in the Sequence Listing as SEQ. ID. NOS. 14, 10, 11, 12, and 13, respectively.

Table 1 is a summary of the RTX toxin genes of *A. pleuropneumoniae* showing their designations and their synonyms. Table 2 shows the distribution of the RTX genes of the 12 serotype reference strains of *A. pleuropneumoniae*. The apx gene profile has been shown to be identical in serotype reference strains and field strains of *A. pleuropneumoniae*. The function of the four genes in the apx operon has also been demonstrated in trans-complementation experiments in *E. coli* and the helper genes for activation and secretion have been shown to be interchangeable functionally to some extent with the *E. coli* or *Proteus vulgaris* hlyC and hlyBD analogues.

Additional examples of RTX toxins are *Pasteurella haemolytica* leukotoxin, *E. coli* hemolysin, *Proteus vulgaris* hemolysin, *A. actinomycetemcomitans* leukotoxin, the RTX toxin encoded by the ash operon of *A suis, A. equuli* hemolysin, *Proteus mirabilis* hemolysin, *Morganella morganii* hemolysin, and *Bordetella pertussis* adenylate cyclase.

The RTX toxins are typically secreted into the culture medium and are recovered in culture supernatants. The ability of a strain of a microorganism to produce an RTX toxin(s) may be determined by assaying for RTX toxin(s) in the culture supernatant by measuring the ability to lyse erythrocytes from pig, sheep, bovine and human and/or kill lymphocytes, epithelial cells, T lymphocytes, and macrophages in vitro (Devenish et al, 1982 Infect. Immun. 60:2139–42), or by using polyclonal or monoclonal antibodies specific to an RTX toxin. For example, the presence of ApxI, ApxII, and/or ApxIII in culture supernatants may be assayed using a chemiluminescence assay as described in Dom, P. et al., Infect. Immunity 60:4328–434, 1992). Briefly, a preparation of porcine neutrophils is allowed to adhere to the walls of cuvettes such as abiolumcuvettes (Lumac, Landgraff, The Netherlands), a known concentration of a strain of the microorganism is added to the cuvettes, and the oxidative burst of the porcine neutrophils is measured as chemiluminescence. The chemiluminescence is typically measured for about 80 minutes using a luminometer (Lumicon, Hamilton, Bonaduz, Switzerland). Opsonized zymosan may be added after a first incubation and chemiluminescence is measured for about an additional 20 minutes. Failure of the zymosan to provoke chemiluminescence indicates that the neutrophils were killed.

In the bacterial preparations of the present invention the RTX toxins are substantially cell-associated. "Substantially cell-associated" used herein refers to the presence in the cell, or on the cell surface of the microorganism strain, of an amount of RTX toxin which is capable of inducing an immunogenic response. The cell association may involve transport across the cell membrane of the RTX toxin, or attachment of the RTX toxin molecule or precursors thereof to the cell membrane before secretion.

The presence of a RTX toxin on the cell surface may be determined for example, using the methods described herein by obtaining membrane enriched fractions of the bacterial preparation, and detecting the presence of the RTX toxins for example by Western Blotting using convalescent sera or polyclonal monospecific or monoclonal antibodies. Similarly, immunoblots of whole cell proteins extracted from the microorganism in the bacterial preparation may also be probed with convalescent sera or polyclonal monospecific or monoclonal antibodies.

In an embodiment of the invention a bacterial preparation is provided comprising one or more strains of different serotypes of *A. pleuropneumoniae* which have one or more of ApxI, ApxII and ApxIII which are substantially cell-associated. The serotype distribution of the RTX toxin genes of *A. pleuropneumonae* in serotypes 1 to 12 is shown in Table 2. Preferably, the preparation contains at least two different serotype strains which collectively have ApxI, ApxII, and ApxIII which are substantially cell-associated. Most preferably, the bacterial preparation contains two strains of serotypes 1 and 3 of *A. pleuropneumoniae* which have ApxI, ApxII and ApxIII substantially cell-associated.

Strains of *A. pleuropneumoniae* known from the literature such as ATCC 27088 (serotype 1), ATCC 27090, ATCC 33378 and ATCC 33377 (reference strains for serotypes 1–5), ATCC 33590 (reference strain for serotype 6), Shope 4071, S1536, S1421, M62, K17, Femo, WF83, 405, CVJ13261, 56153 (reference strains for serotypes 1 through 10), and 8329 (reference strain 12) may be used in this embodiment of the bacterial preparation of the invention. Serotype strains may also be field strains which are obtained from swine with naturally occurring pleuropneumonia (MacInnes et al. 1990) or they may be obtained from researchers working in the field such as researchers from the Dept. of Vet. Microbiology, University of Guelph, Guelph, Ontario, Canada. The strains may also be prepared using the gene transfer methods described herein.

Whole cell protein profiles of the bacterial preparations of the invention prepared using the methods described herein, show that the preparations are enriched in RTX toxins. For example, a 105 K cytolysin (ApxI) and/or a 103 K cytolysin (ApxII) are found in whole cell protein profiles from *A. pleuropneumoniae* preparations. The protein profiles also show that the preparations of the invention contain whole cell antigens substantially analogous to those found in vivo. The in vitro cultures which mimic the profiles of organisms recovered from natural infection should stimulate a protective immune response.

In another embodiment of the invention a bacterial preparation is provided comprising mutant strains prepared by gene transfer techniques which have one or more of ApxI, ApxII and ApxIII which are substantially cell associated. In a preferred embodiment, the bacterial preparation contains a *A. pleuropneumoniae* transposon mutant with an insertion in the apxIBD genes.

The microorganisms in the bacterial preparation which are prepared by gene transfer as described herein may additionally be modified to include other genes. For example, a gene encoding an immunogen or another toxin may be included rendering the preparation useful against additional immunogens/toxins.

II. Preparation of Bacterial Preparations

The present invention also relates to methods for preparing the bacterial preparations of the invention. In one embodiment of the invention, a method is provided for preparing a bacterial preparation comprising selecting one or more strains of a microorganism which produces one or more RTX toxins, and culturing the selected strain(s) under suitable conditions so that the RTX toxin is substantially cell-associated.

The microorganisms which are used to prepare the bacterial preparations of the invention are described above, and include without limitation, strains of *A. pleuropneumoniae, E. coli, P. haemolytica, Actinobacillus suis, Actinobacillus actinomycetem-comitans, Bordetella pertussis, Proteus mirabilis, Proteus vulgaris*, and *Morganella morganii*, which produce one or more RTX toxins. In a preferred embodiment, the microorganism is an *A. pleuropneumoniae* strain which produces one or more of ApxI, ApxII and ApxIII. The ability of the microorganism to produce an RTX toxin may be determined by assaying the culture media for the presence of the RTX toxin using known hemolytic and cytolytic tests some of which are described herein.

The strains are cultured in a medium which permits the RTX toxins to be cell-associated. In a preferred embodiment for preparing a bacterial preparation comprising *A. pleuropneumoniae*, the strains are cultured in a tryptone yeast extract medium. The medium generally has the following composition: 10 to 30 g of tryptone; 2.5 to 7.5 g of yeast extract, 2.5 to 9.0 g of NaCl, 0.4 to 1.15 g of KCl, 0.7 to 2.1 of $Na_2HPO_4$ (10 mM), 0.2 to 0.7 of ($KH_2PO_4$), 0.9 to 2.7 g of glucose, in $dH_2O$ (in a final volume of about 1000 ml). The medium also contains about 1 ml of 10% (wt/vol) NAD per liter. The composition of a preferred medium for preparing bacterial preparations containing *A. pleuropneumoniae* strains comprises 5 to 15 g of tryptone; 3 to 7 g of yeast extract, 3 to 7 g of NaCl, 0.5 to 1.0 g of KCl, 1 to 2 g of $Na_2HPO_4$*($KH_2PO_4$); 1.0 to 2.0 g of glucose, in one liter of $dH_2O$. The composition of a most preferred medium for preparing bacterial preparations containing *A. pleuropneumoniae* strains is set forth in Table 3 (3). Equivalent conditions may also be produced by adjusting the concentrations of the elements of the medium and/or substituting one or more of the elements of the medium.

The strains of the microorganism are cultured overnight, seeded into the medium using a 10% inoculum, and maintained in log phase. The concentration of cells seeded into the medium and the culture conditions will be selected having regard to the nature of the microorganism and other factors known to a skilled artisan. By way of example, $10^9$ to $10^{12}$ cells of an overnight culture may be seeded into 100 ml of liquid medium and incubated with shaking at 50–200 rpm at 37° C., for a period of 6 hours, for strains of *A. pleuropneumoniae*, This can be scaled up for industrial purposes using a 10% inoculum in a new medium. Scale-up is generally progressive for example, with 100 ml of inoculum seeded into 1 liter, 1 liter of inoculum seeded into 10 liters, etc. at 6 to 12 hour intervals. Following growth, cultures may be tested for purity, cell density, cell associated RTX toxin(s) and strain confirmation. The culture may optionally be inactivated as described below. Following inactivation, harvests may be tested for sterility, cell-associated RTX toxin(s), and density.

When the bacterial preparation contains more than one different strain of a microorganism, each strain may be individually cultured and optionally inactivated using the above described methods.

In another embodiment of the invention, the bacterial preparation is prepared by selecting one or more strains of a microorganism which produces one or more RTX toxins, and treating the strains with a substance which interferes with the secretion of the RTX toxins.

Substances which interfere with the secretion of an RTX toxin may be identified by treating a strain of a microorganism which produces one or more RTX toxins, with a substance which is suspected of interfering with the secretion of the RTX toxin, under conditions so that the RTX toxin(s) are capable of being secreted into the medium, and measuring the amount of RTX toxin in the medium or the amount of cell-associated RTX toxin. Microorganisms which may be used to identify interfering substances and methods for measuring the amount of RTX toxin in the medium or the amount of cell-associated RTX toxin are described herein.

An example of a substance which may interfere with the secretion of an RTX toxin is a nucleic acid sequence encoding the D and/or B transport genes inverted relative to their normal orientation for transcription i.e. antisense D and B nucleic acid molecules. Such antisense nucleic acid molecules may be chemically synthesized using naturally occurring nucleotides or variously modified nucleotides designed to increase the biological stability of the molecules or to increase the physical stability of the duplex formed with RTX toxin mRNA or the RTX toxin gene. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

A nucleic acid molecule containing the antisense sequences may be introduced into the microorganism using conventional techniques, such as transformation, transfection, infection, conjugation and physical techniques such as electroporation. Suitable vectors or cloning vehicles for transferring the nucleic acid molecules are known in the art. Examples of suitable vectors are set out in Table 4.

The bacterial preparations of the invention may also be prepared by producing, using gene transfer techniques, strains which have cell-associated RTX toxins. Gene transfer methods can be applied to microorganisms which produce RTX toxins as described herein. For example, *A.*

*pleuropneumoniae* strains which produce RTX toxins may be manipulated so that the RTX toxin(s) are cell-associated by targeted gene mutagenesis using allelic replacement, insertional inactivation, or deletion formation of the D and/or B transport genes, or other genes. En addition to the RTX genes, others genes may also be inserted into the bacterial preparation by gene transfer techniques. Other genes that may be added include genes encoding other antigens or other toxins to increase the immunogenicity of the bacterial preparation and/or to induce a response against other antigens.

Selection marker genes which may be used in insertional mutagenesis by transposition or by allelic replacement include antibiotic resistance genes. Examples of antibiotic resistance genes which may be used include: (a) the gene encoding aminoglycoside 3'phosphotransferase I activity from transposon Tn903 (Oka et al., J. Mol. Biol. 147:217–226, 1981) which confers kanamycin resistance in *A. pleuropneumoniae* (Tascon et al., J. Bacteriol. 175:5717–5722, 1993); (b) variants of transposon Tn5 confer high levels of resistance to kanamycin, bleomycin, and streptomycin to *A. pleuropneumoniae* (Willson, Can. J. Vet. Res. 54 Suppl. S73–S77, 1990); (c) the gene for gentamycin resistance ($Gm^r$) from the IncP plasmid, R1033 (Hirsch et al., Gene 48:203–209, 1986) which confers very high resistance to gentamycin (100 $\mu$g/ml) in *A. pleuropneumoniae*; (d) the $Gm^r$ gene from Tn1696 can also be expressed in *A. pleuropneumoniae* (West et al., 1995); (e) the chloramphenicol resistance gene from an *A. pleuropneumoniae* plasmid pYG10 (Lalonde and O''Hanley, Gene 85:243–246, 1989); (f) the type II $Cm^r$ gene from *Shigella flexneri* plasmid pS-a (Hedges and Datta, Nature 234:220–222, 1971) or Tn9 (West et al., 1995) which have been shown to confer chloramphenicol resistance to *A. pleuropneumoniae*; (g) ROB-1 beta-lactamase (bla) genes originating from *P. haemolytica* (Azad et al.,J Gen. Microbiol. 138:1185–1196, 1992; Craig et al., J. Gen. Microbiol. 135:2885–2890, 1989; and Livrelli et al, Antimicrob. Agents Chemother. 32:1282–1284, 1988) express ampicillin resistance in *A. pleuropneumoniae, P. haemolytica*, and *P. multocida* (West et al., 1995); (h) genes encoding dihydrophteroate synthase, which confers sulfonamide resistance to *A. pleuropneumoniae, P. haemolytica*, and *P. multocida*; (i) streptomycin kinase which confers streptomycin resistance to *A. pleuropneumoniae, P. haemolytica*, and *P. multocida* which are present on a *P. haemolytica* plasmid pYFC1 (Chang et al., Vet. Microbiol. 32:319–325, 1992); and (j) a $Tc^r$ gene originating from *Streptococcus agalactiae* which confers resistance to low concentrations of tetracycline (0.2 $\mu$g/ml) in *A. pleuropneumoniae* (Jansen et al., Infect. Immun., 1995).

If the bacterial preparations are used to prepare vaccines, it is desirable to eliminate the antibiotic resistance for example, using media (e.g. Boekner media) to select for mutants which do not carry the selection marker gene. In the alternative, heavy metal resistance (e.g. mercury) may be used as a selectable marker.

Plasmid vectors which may be used to manipulate genes in microorganisms which produce one or more RTX toxins, in particular of the family Pasteurellaceae, include endogenous plasmids of *A. pleuropneumoniae* and *P. haemolytica*. Examples of endogenous plasmids of *A. pleuropneumoniae* and *P. haemolytica* are pYG53, pYG54 (Lalonde and O'Hanley., supra, 1989); pLS88 which contains the selection marker genes $Sm^r$, $Su^r$, and $Km^r$, plasmid pYFC1 which contains the $Sm^r$ and $Su^r$ genes (Chang et al., Vet. Microbiol. 32:319–325, 1992); pJFF224-NX and PJFF224-XN (Frey et al, Res. Microbiol. 143:263–269, 1992); a native 4.3 kb *P. haemolytica* plasmid pPH33 (Azad et al., J. Gen. Microbiol. 138:1185–1196, 1992; Craig et al., J. Gen. Microbiol. 135:2885–2890, 1989); a 4.3 kb plasmid pPH843 from *P. haemolytica* and a derivative of it pAKA which has been constructed as a mobilizable suicide vector for gene replacements in *P. haemolytica* and *P. multocida* (Azad et al., Gene 145:81–85, 1994); pGZRS-18/19 (West et al., 1995); and, the cosmid plasmid pSW206 which is a derivative of the broad host range plasmid RK2 and contains the $Km^r$ gene from Tn903 for selection. The properties of some plasmids are summarized in Table 4.

Transposon inactivation by transposon mutagenesis is a useful tool for the genetic manipulation of microorgamsms and it may be used to produce a microorganism with cell-associated RTX toxins. A transposon mutagenesis procedure involving the use of a mobilizable suicide plasmid pLOF Km carrying a mini Tn10 transposon carrying the $Km^r$ gene from Tn903, and an IPTG inducible transposase located outside the mobile element (Herrero et al., J. Bacteriol. 172:6557–6567, 1990) provide transposon frequencies of approximately $10^{-5}$ in *A. pleuropneumoniae* (Tascon et al., J. Bacteriol. 175:5717–5722, 1993). Single, stable, and random insertions into the chromosome of *A. pleuropneumonia* serotypes 1 to 11 can be made with this system. This system has been used to isolate insertions in apxIA or apxIB of the *A. pleuropneumoniae* serotype 1 strain 4074 (Tascon et al., J. Bacteriol. 175:5717–5722, 1993; Tascon et al., Mol. Microbiol. 14:207–216, 1994).

The present inventors have prepared transposon mutants of *A. pleuropneumoniae* CM5 with insertions in the apxIBD genes (see Example 5). A suicide conjugative plasmid, pLOFKm, carrying a mini-Tn10 was used for the transposon mutagenesis as described by Tascon et al, Bacteriol. 175:5717–5722 (1993). The plasmid was mobilized from *E. coli* to *A. pleuropneumoniae* by biparental mating. Transconjugants were screened on blood agar plates, and non-haemolytic mutants were selected. The transposon insertion in the BD region in the mutants was found to interfere with the export of the ApxI toxin into the culture medium.

Allelic gene exchange using non-replicating or conditionally-replicating plasmids has been used widely for the mutagenesis of both procaryotes and eukaryotes. Allelic exchange can be used to create deletions of specific genes (e.g., the B and D genes), or parts of genes. Gene replacement systems are available for *A. pleuropneumoniae* and *P. haemolytica*. For example, an efficient system for targeted mutagenesis of *A. pleuropneumoniae* has been described by Jansen et al., Infect. Immun., 1995. The system is based on a conditionally-replicating thermosensitive, broad-host-range plasmid, pVE6063 (Maguin et al., J. Bacteriol. 174:5633–5638, 1992). The pVE6063 plasmid does not replicate in *A. pleuropneumoniae* and insertional mutagenesis occurs by homologous recombination. The apxBD genes inserted in pVE6063, may thus be deleted by replacement with either $Cm^r$ genes from *S. aureus* or by $Tc^r$ genes from *S. agalactiae*. The constructs may subsequently be introduced in *A. pleuropneumoniae* serotype 1 by electroporation.

Gene replacement in *P. haemolytica* may also be carried out using the system described by Tatum et al. (Appl. Environ. Microbiol. 60:2011–2016, 1994). In the system a cloned aroA gene is inactivated with a fragment containing *P. haemolytica* ampicillin resistance gene. The plasmid carrying the disrupted fragment is methylated using cloned PhaI and introduced into *P. haemolytica* by electroporation.

Mutants with the disrupted aroA gene integrated into the chromosome may be obtained after repeated passage.

Plasmids may be transferred to species of the family Pasteurellaceae using electroporation and conjugation. Conditions for the electroporation can be established for each strain of microorganism. Conjugative mobilization of plasmids generally provides higher transfer rates than electroporation (Lalonde and O'Hanley. Gene 85:243246, 1989; Azad et al., Gene 145:81–85, 1994). The recipient strain needs to be modified so that the donor (usually *E. coli*) can be counterselected. This is generally done by screening for spontaneous nalidixic, rifampicin, or streptomycin resistant mutants or by introduction of an antibiotic resistance gene on a compatible plasmid to the recipient strain (Lalonde and O'Hanley, 1989, supra; Azad et al., 1994, supra). Virulent *E.coli* bacteriophages such as T4 and T7 may also be used for counterselection of the donor strains.

It will also be appreciated that the bacterial preparations of the invention may also be prepared using a strain which naturally has cell associated RTX toxin(s). For example, serotype 3 strains of *A. pleuropneumoniae* which do not contain the apxIB and D genes which are necessary for ApxII secretion, may be used to prepare *A. pleuropneumoniae* bacterial preparations.

Existing strains may be modified using the methods described above and conventional recombinant techniques known in the art, to produce a strain which has cell-associated RTX toxin(s). For example, a serotype 3 strain of *A. pleuropneumoniae* may be modified so that it does not secret ApxIII using the gene transfer techniques discussed above; and the strain may be modified to express ApxI by introducing the apxIC and apxB genes into the strain using conventional recombinant techniques. Thus, the resulting modified strain produces cell-associated ApxI, ApxII, and ApxIII. A modified serotype 1 strain which produces ApxI, ApxII, and ApxIII may also be constructed by modiying a serotype 1 strain using the gene transfer techniques discussed above so that it does not secret ApxI, and the apxIIIA and apxIIIC genes may be introduced into the strain using conventional recombinant techniques, so that the strain expresses ApxIII.

The composition of the bacterial preparations prepared by the above methods may be confirmed for example for *A. pleuropneumoniae* preparations by assaying for cell-associated ApxI, ApxII, and ApxIII as described herein. The whole cell protein profile of the bacterial preparation may also be determined by the methods described herein (See for example Examples 1 and 2). The bacterial preparations of the invention have a whole cell protein profile that substantially mimics the whole cell protein profile of in vivo cultures of *A. pleuropneumoniae* recovered from natural infection (See FIG. 9).

III. Utility of the Bacterial Preparations

The bacterial preparations may be used as vaccines for the prophylaxis and treatment of infectious diseases caused by microorganisms which produce RTX toxins. Infectious diseases caused by microorganisms which produce RTX toxins include swine pleuropneumonia caused by *A. pleuropneumoniae*; shipping fever in cattle caused by *P. haemolytica*; whooping cough caused by *B. pertussis*; in foals sleepy foal disease or joint ill (purulent nephritis, arthritis), in adult horses abortion, septicemia, nephritis, and endocarditis, arthritis in piglets and abortion and endocarditis in swine caused by *A. equuli*; septicemia in swine and horses, pneumonia, nephritis, and arthritis in swine, polyarthritis in horses and abortion in cattle caused by *A. suis*; urinary infections, peritonitis, meningitis, and septicemia caused by virulent strains of *E. coli*.; (acute juvenile) periodontitis caused by *Actinobacillus acinetomycetemcomitans*; and gastroenteritis caused by *P. mirabilis* or *M. morganii*. Thus, the vaccines can be intended for administration to humans and various other mammals, including bovines, equines, and swine.

Prior to formulating into a vaccine the strains of the microorganism in the preparation may be inactivated. The strains of the microorganism may be inactivated using heat (e.g. treatment for two hours at 60° C.) or chemical agents, typically those commonly used for commercial vaccine preparations, following standard procedures known to persons skilled in the art. Chemical agents suitable for inactivating the bacterial preparations of the invention include β-propiolactone (β-Prone, Grand Laboratories Inc., Larchwood, Iowa.) or 0.1 M binary-ethyleneinine (BEI). Inactivation of the cultures may be confirmed for example, by plating multiple samples onto a medium such as CBA-NAD, and incubating the plates for 48 h at 37° C. with 5% $CO_2$.

It will also be appreciated that inactivation will not be necessary when the strains used in the bacterial preparation are attenuated.

The vaccine of the invention contains an immunologically effective amount of a bacterial preparation of the invention, for example between $5\times10^9$ to $5\times10^{10}$, preferably $1\times10^{10}$ to $2\times10^{10}$ cells per dosage unit. A dosage unit is typically 0.5 to 2 ml. The optimum amounts of the bacterial preparation depend on the nature of the infection against which protection is required, the characteristics of the mammals to be protected, and other factors known to persons skilled in the art.

In an embodiment of the invention, the vaccine contains a bacterial preparation comprising at least one *A. pleuropneumoniae* strain which produces an RTX toxin which is substantially cell-associated. The strains used in the bacterial preparation in the vaccines are selected based on the toxins produced by the different serotypes as shown in Table 2. A vaccine containing an *A. pleuropneumoniae* strain of serotypes 7 or 12 which has been treated so that the ApxII toxin is substantially cell-associated will provide protective immunity against infections by serotypes 7 or 12. A vaccine containing *A. pleuropneumoniae* strain serotype 10 which has been treated so that the ApxI toxin is cell-associated will provide protective immunity against infections by serotype 10. Similarly, a vaccine containing strains of serotypes 1, 5, 7, 10, 11, and 12 which have been treated so that the ApxI and ApxII toxins are cell-associated will provide protection against infection by serotypes 1, 5, 7, 10, 11, and 12. A vaccine containing serotypes 2, 3, 4, 6, 7, 8, and 12 which have been treated so that the ApxII and ApxIII toxins are cell-associated will provide protection against infection by serotypes 2, 3, 4, 6, 7, 8, and 12. A preferred vaccine of the invention contains strains which are capable of collectively producing ApxI, ApxII, and ApxIII. For example, the vaccine may contain strains of serotypes 1 and 3. This preferred vaccine should be effective against all pathogenic strains of *A. pleuropneumoniae* including the known serotypes set out in Table 2 as well as any still unknown serotypes, strains or mutants. If new strains produce different toxins a comparable approach may be employed. The vaccine may also contain strain(s) with cell-associated RTX toxins which have been prepared using the gene transfer and recombinant methods described herein.

In addition to the bacterial preparation, the vaccine may comprise an immunologically acceptable carrier such as aqueous diluents, suspending aids, buffers, excipients, and one or more adjuvants known in the art. Suitable adjuvants include aluminum hydroxide, Freunds adjuvant (complete or incomplete), bacteria such as *Bordetella pertussis* or *E. coli* or bacterium derived matter, immune stimulating complex (iscom), oil, saponin, oligopeptide, emulsified paraffin-Emulsigen™ (MVP Labs, Ralston, Nebr.), L80 adjuvant containing AL(OH)$_3$ (Reheis, N.J.), Quil A (Superphos), or other adjuvants known to the skilled artisan. Preferably, the adjuvant is L80 adjuvant containing AL(OH)$_3$ (Reheis, N.J.) and Quil A (Superphos). The vaccine may also contain preservatives such as sodium azide, thimersol, gentamicin, neomycin, and polymyxin.

The vaccine may be a multivalent vaccine and additionally contain other immunogens related to other diseases in a prophylactically or therapeutically effective manner. For example, a vaccine containing a bacterial preparation comprising *A. pleuropneumoniae* strains of serotypes producing RTX toxins which are substantially cell associated, may also contain inactivated cultures of one or more of *Haemophilus parasuis* which causes polyserositis; *Pasteurella multocida* which contributes to the severity of *A. pleuropneumoniae* respiratory clinical signs and pathology; *Bordetella bronchiseptica* which causes atrophic rhinitis; and *Erysipelothrix rhusiopathiae* which causes erysipelas. Additional immunogens may also be added to the vaccine in a number of ways. In one example, the DNA encoding the immunogen may be incorporated into strains in the bacterial preparation using gene transfer techniques. In another example, the immunogen may be added in an immunologically effective amount directly to the preparation.

The vaccines of the invention may be administered in a convenient manner, such as intravenously, intramuscularly, subcutaneously, intraperitoneally, intranatally or orally. Preferably the vaccine is administered intramuscularly or subcutaneously. The vaccine may be administered in a liposome delivery system to allow for the slow sustained release of the immunogens.

The dosage will depend on the nature of the infection, on the desired effect and on the chosen route of administration, and other factors known to persons skilled in the art. For example, in respect of a vaccine containing an *A. pleuropneumoniae* strain which produces an RTX toxin which is substantially cell-associated, about 1 to 5 ml may be administered intramuscularly or subcutaneously to pigs 30 lbs. or over, and 0.5 to 1 ml for pigs under 30 lbs. A second vaccination is generally recommended two to three weeks later. Breeding females are generally given two doses. The initial dose may be administered about five weeks prior to farrowing, and the second dose 2 weeks to three weeks prior to farrowing. Revaccinations are generally given annually.

The bacterial preparations of the invention are also useful for preparing antibodies which may be used as a means of passive immunization. Within the context of the present invention, antibodies are understood to include monoclonal antibodies, polyclonal antibodies, antibody fragments (e.g., Fab, and F(ab')$_2$ and recombinantly produced binding partners. Antibodies may be prepared using conventional methods.

For example, polyclonal antibodies may be readily generated by one of ordinary skill in the art from a variety of warm-blooded animals such as horses, cows, various fowl, rabbits, mice, or rats. Briefly, the bacterial preparation is utilized to immunize the animal through intraperitoneal, intramuscular, intraocular, or subcutaneous injections, in conjunction with an adjuvant such as Freund complete or incomplete adjuvant. Following several booster immunizations, samples of serum are collected and tested for reactivity to the bacterial preparations. Particularly preferred polyclonal antisera will give a signal on one of these assays that is at least three times greater than background. Once the titer of the animal has reached a plateau in terms of its reactivity, larger quantities of antisera may be readily obtained either by weekly bleedings, or by exsanguinating the animal.

The following non-limiting examples are illustrative of the present invention:

EXAMPLES

The following materials and methods were utilized in the investigations outlined in the examples:

Bacterial Strains and Growth Conditions

*Actinobacillus pleuropneumoniae* CM5, a serotype 1 strain, was isolated from a pig with naturally occurring pleuropneumonia (Rosendal et al., 1981) and stored at −70° C. in pleural fluid. *A. pleuropneumoniae* BC181, a serotype 3 strain, was isolated from a case of porcine pleuropneumonia in British Columbia, and stored frozen at −70° C. in skim milk with 20% glycerol (Rosendal et al., 1981). Serotype 1 strain VSB68, was provided as a lyophilized culture by Langford/Cyanamid, Guelph, Ont. For use, cultures were streaked onto trypticase soy agar supplemented with 5% (vol/vol) heated sheep blood (chocolate agar) and 0.01% (wt/vol) nicotinamide adenine dinucleotide (CBA-NAD) and incubated for 24 h at 37° C. with 5% $CO_2$.

Cultures used in preparation of antigens for polyacrylamide gel electrophoresis (PAGE) and Western blotting (WB) experiments were grown in several different media under different conditions. A well defined commercial medium, RPMI (Table 3) supplemented with 10% fetal calf serum (FCS) was used. Tryptone yeast extract broth (TYE) (Table 3; O'Reilly, and Niven, 1985) was used to provide enriched growth conditions.

To provide oxygen-limited conditions, screw-capped 500 ml glass bottles (Corning) were filled to the top with medium prior to autoclaving and the caps tightened to limit dissolved oxygen after autoclaving. Cultures were incubated without agitation. Aerobic conditions were achieved by incubating cultures in 500 ml bottles partially filled with medium at 200 rpm on a rotary shaker.

Strains of *A. pleuropneumoniae* serotypes 1, 2, 5, 7, and 9 from a commercial bacterin were provided as individual, formalin-inactivated suspensions by Langford/Cyanamid.

Inactivation

Cultures were inactivated using one of three techniques. Six h cultures were heated to 6° C. for 2 h and then cooled to 4° C. or β-propiolactone (β-Prone, Grand Laboratories Inc., Larchwood, Iowa.) was added at the rate of 1 ml/1000 ml and the cultures incubated at 37° C. and 100 rpm overnight. Alternatively, 0.1 M binary-ethylenimine (BEI) was added at the rate of 100 ml/1000 ml, and the cultures incubated at 37° C., and 100 rpm overnight. The BEI was neutralized using 100 ml of 1 M sodium thiosulfate. Inactivation of the cultures was confirmed by plating multiple 1 ml samples onto CBA-NAD, and incubating the plates for 48 h at 37° C. with 5% $CO_2$. From each inactivated culture, 500 ml was stored at 4 to 7° C. The remaining 500 ml from each culture was centrifuged at 15,000×g for 15 min at 4° C. The supernatant was recovered and stored at 4° C. The cell pellet was washed once in PBS. The cells were resuspended in 10 ml of PBS and stored frozen at −20° C.

Pig Sera

Sera from pigs naturally infected with *A. pleuropneumoniae* serotypes 1, 5, and 7 were supplied by B. J. Fenwick, Manhattan, Kans. Serum from a pig immunized with gel-purified haemolysin/cytolysin from *A. pleuropneumoniae* serotype 1 was provided by J. Devenish (1989). Because ApxI and ApxII have very similar molecular weights, this antisera recognizes both ApxI and ApxII. Sera from pigs vaccinated with commercial bacterin, experimental bacterins, adjuvant, PBS, or low-dose challenged with *A. pleuropneumoniae* CM5, were obtained in the study described herein. Pigs which were low-dose challenged were exposed to $1 \times 10^6$ cells on two separate occasions and treated with penicillin at the first sign of respiratory distress. These pigs were solidly immune to subsequent challenge.

Collection and Processing of Blood Samples

Blood was collected from the orbital sinus using 20 gauge needles. Alternately, blood was obtained from the anterior vena cava using 10 ml Vacutainer tubes and 20 gauge needles. The blood was allowed to clot at room temperature and the serum separated by centrifugation at 2000 rpm for 10 min in a Sorvall GLC-1 centrifuge (DuPont Ltd., Mississauga, Ont.). The serum was dispensed into plastic vials and stored at $-20°$ C. prior to use.

Preparation of Antigens

Outer membrane proteins (OMPs) were prepared by the method of Deneer and Potter (1989). Cells grown overnight on CBA-NAD were washed from plates and suspended in 1 ml sterile PBS. Approximately 100 µl were then used to inoculate 10 ml of growth medium. The culture was incubated for 2 h and used to inoculate 1 liter of the same liquid medium. This culture was incubated overnight under appropriate conditions. Bacteria were harvested by centrifugation in 500 ml bottles at 7000 rpm for 20 min at $4°$ C. in a Sorval RC5B centrifuge with a GS3 rotor (DuPont). The resulting pellets were washed by repeat centrifugation with PBS, pooled, and frozen at $-20°$ C. for overnight storage. The next day, the pellets were thawed, resuspended in 10 mM HEPES, pH 7.4 (at a rate of approximately 1 g wet weight cells to 18 ml), and sonicated until the solution cleared (about 10 min). Aggregates and unbroken cells were removed by centrifugation at 10,000 rpm for 4 to 5 min at $4°$ C. in a SS34/SA600 rotor. The supernatants were incubated for 10 min at room temperature with 2% (vol/vol) Sarcosyl in 10 mM HEPES, and then centrifuged at 100,000×g for 60 min at $4°$ C. in a Beckman XL-90 ultracentrifuge using an SW41 rotor. The supernatants were discarded and the pellets resuspended in 6.5 ml of 10 mM HEPES. An equal volume of 2% sarcosyl in 10 mM HEPES was added and the preparation covered with Parafilm and incubated at room temperature for 30 min with shaking. The preparations were then centrifuged at 100,000×g for 60 min at $4°$ C. Pellets were resuspended in approximately 200 µl pyrogen free water and stored at $-20°$ C. The protein content was determined using the Bio-Rad protein microassay kit (Bio-Rad, Richmond, Calif.). For electrophoresis, the preparations were diluted to 1 µg/µl in Laemmli's sample buffer and boiled for 5 min.

In vivo antigen was recovered from pleural fluid obtained at necropsy from pigs experimentally infected with *A. pluroptneumoniae* CM5. Fluid was centrifuged at 60×g for 20 min at $4°$ C. The supernatant was centrifuged three more times as before. The resulting supernatant was centrifuged at $4°$ C. to pellet the bacteria. Due to the amount of fibrin in the material, the quantity of cells recovered was very low. The purity of the washed pellet was determined by plating on CBA-NAD.

Polyacrylamide Gel Electrophoresis (PAGE)

A modification of the discontinuous buffer system of Laenli as described by Rodriquez and Tait (1983) was employed using the Bio-Rad Miniprotean II electrophoresis apparatus. The stacking gel contained 4% (wt/vol) acrylamide/0.1% (wt/vol) bis-acrylamide and the resolving gel contained 12% (wt/vol) acrylamide/0.4% (wt/vol) bis-acrylamide. Prior to electrophoresis, samples were solubilized by boiling for 5 min in SDS-PAGE sample buffer containing 20% (vol/vol) glycerol, 10% (vol/vol) 2-mercaptoethanol, 6% (wt/vol) sodium dodecyl sulfate (SDS), 0.125 M Tris (pH 6.8) and 0.1% (wt/vol) bromophenol blue. Electrophoresis was carried out for 45 min at 195 V with cooling. The gels were then used for immunoblotting, stained with Coomassie Brilliant Blue G250 (Bio-Rad) or silver stained using the Bio-Rad silver staining kit (Bio-Rad). High molecular weight, low molecular weight, or pre-stained molecular weight standards (Bio-Rad) were included in the gels as needed.

Immunoblotting

Proteins separated by SDS-PAGE were transferred to nitrocellulose (NC; Schleicher & Schuell, Inc., Keene, N.H.) or nylon (Biotrans; ICN Pharmaceuticals Inc., Irvine, Calif.) membranes using the Bio-Rad Mini Trans Blot blotting apparatus. Transfers were performed at 100 V for 1 h. After transfer, the membranes were blocked overnight in skim milk solution (BLOTTO-Table 3). Following two 15 min washes in Tween-Tris buffered saline (TTBS-Table 3) the membranes were incubated for 2 to 24 h at room temperature with various swine antisera diluted 1:100 in antibody buffer (Table 3). Various sera were compared on the same blot using a 16 channel slit-blotter (Miniblotter-16, Immunetics, Cambridge, Mass.). Following two washes in TTBS the blots were incubated for 1 h at room temperature with 1:1000 goat anti-swine-IgG (H&L)-alkaline phosphatase (Kirkegaard and Perry Laboratories Inc., Gaithersburg, Md.). Following two 5 min washes in Tris buffered saline (TBS), blots were developed using 5-bromo-4-chloro-3-indoyl phosphate and nitroblue tetrazolium colour development substrate (BCIP/NBT, Bio-Rad). Development was stopped by rinsing the blots in distilled water.

Experimental Bacterin Preparations

Growth Conditions—Trial 1

Lyophilized cultures of *A. pleuropneumoniae* CM5 (serotype 1), and BC181 (serotype 3) were plated onto 5% sheep blood agar with 0.01% (wt/vol) NAD (SBA-NAD) and incubated overnight at $37°$ C. with 5% $CO_2$. Isolated colonies of each strain were selected and seeded into separate 100 ml volumes of TYE with 0.01% NAD (TYE-NAD) pre-warmed to $37°$ C. These were incubated overnight with shaking (100 rpm) at $37°$ C. These seed cultures were inoculated into 1 liter volumes of TYE-NAD at $37°$ C., and incubated for 6 h at 100 rpm. After incubation, cultures were plated for purity and heat-inactivated for 2 h at $60°$ C. These cultures were used to make experimental bacterin A.

Growth Conditions—Trial 2

*A. pleuropneumoniae* VSB68, serotype 1 (Langford/Cyanamid) was used to prepare the experimental bacterins for this trial. Cultures were grown by two different methods. The first culture was grown according to the production methodology used to produce the commercial multi-strain bacterin. Overnight cultures of A. pleuropneumoniae from CBA-NAD plates were seeded into 100 ml of Tryptic Soy Broth (TSB) with 0.1% NAD (TSB-NAD) at 37° C., and incubated with shaking at 100 rpm for 24 h. These overnight cultures were then seeded into 1 litre of TSB-NAD at 37° C. and incubated as before for 24 h. Following incubation, the cultures were heat-inactivated for 2 h at 60° C. Alternately, 24 h cultures from CBA-NAD plates were seeded into 100 ml of TYE-NAD broth and incubated for 24 h at 37° C. with shaking at 100 rpm. This culture was then used to seed 1 litre of TYE-NAD at 37° C. which was further incubated for 6 h at 37° C. with shaking at 100 rpm. Following incubation the culture was heat-inactivated for 2 h at 60° C. These cultures were used to make experimental bacterins B, C, D, and E.

Bacterin Composition—Trial 1

The antigens for bacterin A were blended to a final density of $1 \times 10^{10}/2$ ml dose of each strain. The bacterin was adjuvanted with L80 adjuvant (Langford/Cyanamid), containing $Al(OH)_3$ (Reheis), and Quil A (Superphos, Denrmark).

The composition of bacterin A is summarized in Table 5.

Bacterin Composition—Trial 2

Experimental bacterins B, C, D, and E were prepared from the heat-inactivated cultures of A. pleuropneumoniae VSB68. The culture from each medium (TYE or TSB) was used to prepare two bacterins at $6 \times 10^9$ or $2 \times 10^{10}/2$ ml dose respectively. All bacterins were adjuvanted with AlOH, and Quil A. The composition of bacterins B, C, D, and E are summarized in Table 6.

Vaccination and Challenge with Bactrin Compositions

For each experiment, pigs were vaccinated intramuscularly with two 2 ml doses of vaccine or placebo, 21 days apart. Low-dose vaccination was performed by exposing the pigs to an aerosol of a culture containing approximately $10^6$ organisms/ml of A. pleuropneumoniae CM5A. Aerosol challenge was performed 14 days following the second vaccination using the following steps:

1. Challenge organism is obtained from pleural fluid of an experimentally infected pig, stored at −70° C. (Serotype 1, strain CM5)
2. Subculture the organism overnight on chocolate blood agar with 0.1% NAD to determine purity.
3. Resuspend the growth in sterile PBS and adjust the $OD_{625}=0.2$
4. For challenge this suspension is further diluted 1/10–1/500 in PBS depending on the age and type of pig (CDCD vs SPF). (CFU=approx. $10^6$/ml)
5. Place 75 ml of diluted suspension into the DeVilbiss nebulizer which is connected to the aerosol chamber containing the pigs.
6. Run the nebulizer for 10 minutes to fill the chamber. With the nebulizer off, allow a further 10 minutes for the pigs to inhale the aerosol.

Trial 1—Bacterin A

The pigs used in this experiment were from a litter of Caesarian-derived, colostrum-deprived (CDCD) piglets of a sow from the Arkell Research Station, University of Guelph. The piglets were hand reared in isolation, and fed Launch, a liquid milk replacement (Shur-Gain, Canada Packers Inc.), and Vital, a bovine colostrum supplement (Shur-Gain, Canada Packers Inc.), until they were able to eat solid swine rations. This litter was one of nine similar litters involved in a larger study examining humoral and cell-mediated immunity to A. pleuropneumoniae.

Pigs were assigned ad hoc to groups as follows: improved bacterin (5), commnercial bacterin (2), low-dose exposed (3), adjuvant controls (4), PBS controls (6). Starting at day 35, piglets in each treatment group were either low-dose exposed or injected IM with the bacterins, adjuvant or PBS. This was repeated 21 days later. Two weeks after the second treatment, all the piglets were challenged with an aerosol of A. pleuropneumoniae CM5 as described above. Blood samples were taken just prior to the first vaccination, the second vaccination, challenge, and euthanasia.

Trial 2—Bacterins B, C, D, and E

The pigs used in the second vaccination trial were derived from an SPF herd and obtained through Dr. C. Templeton (Orange Hill Farms, Ontario, Canada). Representative pigs from the herd were determined to be free of antibodies to A. pleuropneumoniae toxins by ELISA and susceptible to challenge with A. pleuropneumoniae CM5 in a preliminary challenge experiment.

Thirty pigs were placed ad hoc into three isolation rooms, and were then randomly assigned a treatment by drawing ear tags pre-labelled with a treatment group from a bag. Each group was vaccinated IM with 2 doses of vaccine or placebo, 21 days apart. Pigs were challenged with an aerosol of A. pleuropneumoniae CM5 two weeks after the second dose. Blood samples were taken immediately prior to the first and second vaccinations, prior to challenge, and at euthanasia. The pigs were weighed at first vaccination and those surviving to day 5 post-challenge were weighed again prior to euthanasia and necropsy.

All procedures involving animals were carried out in accordance with the guidelines outlined in the Canadian Council On Animal Care's "Guide to the Care and Use of Experimental Animals".

ELISA

Serum antibody titres to lipopolysaccharide (LPS), capsular polysaccharide (CPS), and haemolysin/cytolysin (CYT) were measured by ELISA according to the method of Bossé et al. (1992). Antigens were prepared as described previously (Bossé et al., 1992). To coat ELISA plates (Microwell 2-69620, Nunc), CPS was diluted to 0.125 $\mu$g/ml and LPS was diluted to 0.625 $\mu$g/ml in carbonate coating buffer. Plates were incubated at 4° C. overnight with 100 $\mu$l of diluted antigen per well. Flat bottom microtitre plates (Immulon II, Dynatech Laboratories) were coated with 100 $\mu$l/well of a 1:2000 dilution of rabbit anti-CM5 CYT overnight at 4° C. Wells were blocked with 5% normal rabbit serum in PBS-T for 1 h. Using rabbit anticytolysin antibody (Devenish et al., 1989), CYT was captured out of crude supernatant containing 800 hemolytic unit/ml by incubation with 100 $\mu$l/well overnight at 4° C. Plates were washed 3 times with 250 $\mu$l PBS-T between each step.

Serum samples were diluted 1:50, 1:200, 1:800, and 1:3200 in TTBS. For the CYT ELISA, 5% normal rabbit serum was added to the diluent. Samples were tested in duplicate on opposing quadrants of each plate. Positive and negative control sera were included on all plates. Positive serum was obtained from a pig exposed to a low-dose challenge with A. pleuropneumoniae CM5.

Plates were incubated with serum dilutions (100 $\mu$l per well) for 2 h at room temperature. After washing, plates were incubated for 2 h at room temperature with biotin-labelled mouse anti-swine IgG (H+L) (Zymed Laboratories, South San Francisco, Calif.), and then for 30 min with 50 $\mu$l/well of 1:8000 stepavidin-peroxidase (Zymed Laboratories, South San Francisco, Calif.).

The hydrolysis of $H_2O_2$ by bound peroxidase was determined in the presence of ABTS (Boehringer Mannheim Biochemical, Indianapolis, Ind.) at a wavelength of 405 nm with a microplate reader (Bio-Tek Instruments, Winooski, Vt.). The absorbance of the 1:200 dilution of the positive control serum was monitored until the OD reached 1.000 at which time the plates were read.

The mean OD of duplicate wells for each serum dilution were calculated and these data were used to calculate least squares mean OD for each treatment group (General linear models procedure, the SAS system, Kelwig and Council, 1979).

Example 1
Variation of Cellular Antigens as a Function of Growth Conditions

The expression of WC and outer-membrane protein antigens of A. pleuropneumoniae CM5 grown under different conditions in different media was examined. Cells were grown under aerobic or anoxic conditions. In vivo antigen, recovered from the lungs of infected pigs, was compared. Coomassie blue-stained polyacrylamide gels of WC and outer membrane protein enriched fractions are shown in FIG. 4A and FIG. 4B.

Figure 4:
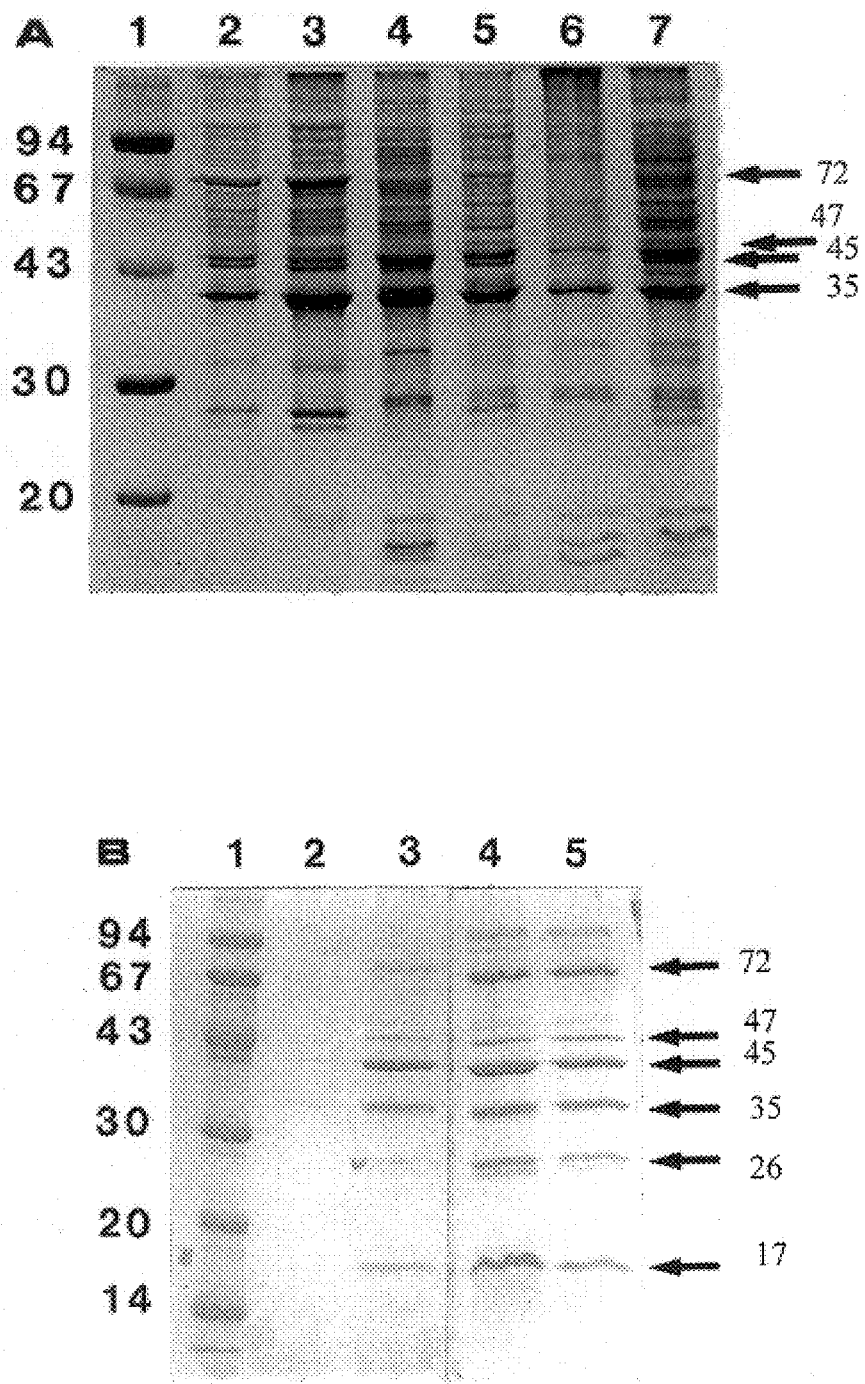
FIG. 4A shows Coomassie-blue stained SDS-PAGE profiles of WC proteins of *A. pleuropneumoniae* serotype 1 grown in different media under various conditions.
FIG. 4B shows Coomassie-blue stained SDS-PAGE profiles of outer-membrane enriched fractions (B) of *A. pleuropneumoniae* serotype 1 grown in different media under various conditions.

The following should be noted in FIGS. 4A and 4B: Molecular weight markers (lane 1), WC proteins of strain CM5 grown under anoxic conditions in RPMI (lane 2), CM5, RPMI, aerobic (lane 3), CM5, TYE, anoxic (lane 4), CM5, TYE, aerobic (lane 5), strain VSB68, TSB, aerobic (lane 6), CM5 in vivo (lane 7). The positions of the 35, 45, 47, and 72K bands are indicated with arrows. The sizes of the molecular weight markers (in K) are indicated on the left; (B) Molecular weight markers (lane 1), Outer-membrane protein-enriched fractions of strain VSB68, TSB, aerobic (lane 2), CM5, TYE, aerobic (lane 3), CM5, RPMI, anoxic (lane 4), CM5, RPMI, aerobic (lane 5). The positions of the 17, 26, 32, 40, 42 and 72K bands are indicated with arrows. The sizes of the molecular weight markers (in K) are indicated on the left.

In FIG. 4A, the PAGE profiles of WC preparations derived from RPMI (aerobic and anoxic) (lanes 2 and 3), TYE (aerobic and anoxic) (lanes 4 and 5), TSB (bacterin) (lane 6) and in vivo cultures (lane 7) are shown. There were major protein bands at 47K, 45K, and 37K. An additional major protein band was seen at 72K in WC samples from the RPMI-grown cultures (lanes 2 and 3). This band was not as evident in the WC samples grown in the other media. The TSB WC gel profile (lane 6) showed significant smearing of bands in the high molecular weight range and individual bands were difficult to discern.

In FIG. 4B, PAGE profiles of TSB (bacterin) (lane 2), TYE (lane 3), and RPMI (lane 4 and 5) derived OMP samples are shown. Major OMPs were detected at 17K, 26K, 32K, 40K, 42K and 72K in the RPMI and TYE grown samples (lanes 3, 4, and 5). Unfortunately, the OMP yields from bacterin and in vivo cultures were too low to make definitive comparisons possible.

In order to determine whether there were other differences in antigen expression of A. pleuropneumoniae due to medium and growth conditions, the protein profiles were investigated by immunoblotting. Sera collected from swine which had been vaccinated with a commercial bacterin, low-dose challenged, or mock-vaccinated, were used (Table 7). The sera were used to probe Western blots of WC fractions of A. pleuropneumoniae serotype 1 from TSB, TYE, RPMI and in vivo cultures (FIGS. 5A to 5C).

Figure 5:
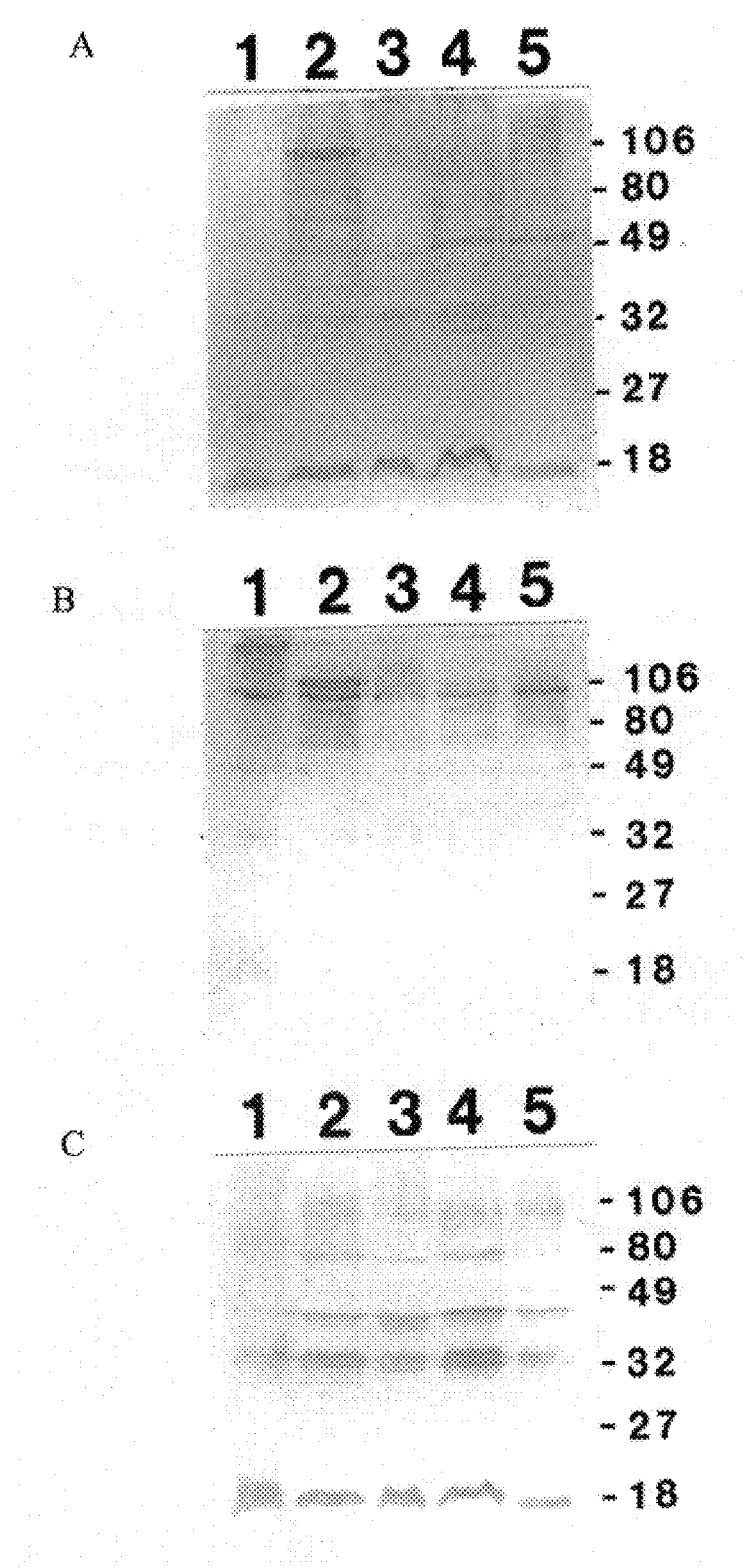

FIGS. 5A to 5C show Western blots of WC proteins of A. pleuropneumoniae serotype 1 grown in various media probed with sera from a pig exposed to low-dose challenge of A. pleuropneumoniae CM5 (A), or sera from a pig hyperimmunized with purified cytolysin from CM5 (B) (Devenish and Rosendal, 1989), or sera from a pig immunized with commercial bacterin (C). Note the following in the Figures: WC proteins of strain VSB68 grown in TSB aerobically (lane 1), strain CM5 grown in TYE, aerobic (lane 2), CM5, TYE, anoxic (lane 3), CM5, RPMI (lane 4), in vivo (lane 5). The positions and sizes of the molecular weight markers (in K) are indicated on the right.

FIG. 5A shows a Western blot of WC preparations probed with sera from low-dose challenged pigs. An antigen of an approximate molecular weight of 105K, which appeared as a doublet, was detected in cells grown in TYE (lane 2) but, not in the other media (lanes 3 and 4), nor in in vivo grown cells (lane 5). When hyperinmmune pig serum raised against gel-purified CM5 cytolysin was used to probe an identical blot, a similar band was seen in the TYE grown WC preparation but not in the other samples (FIG. 5B). Serum from a pig vaccinated with a commercial A. pleuropneumoniae bacterin failed to recognize this antigen, but did detect antigens of approximate molecular weights of 17K, 32K, 34K, and 40K in all the preparations (FIG. 5C).

A similar result was seen when immunoblots of WC proteins of A. pleuropneumoniae strain BC181, serotype 3, grown in TYE broth were probed with the same sera. The sera from low-dose exposed pigs recognized a unique band at 105K as well as an additional band at approximately 120K. These bands were not recognized by the sera from bacterin vaccinates or controls (Data not shown).

Figure 6:
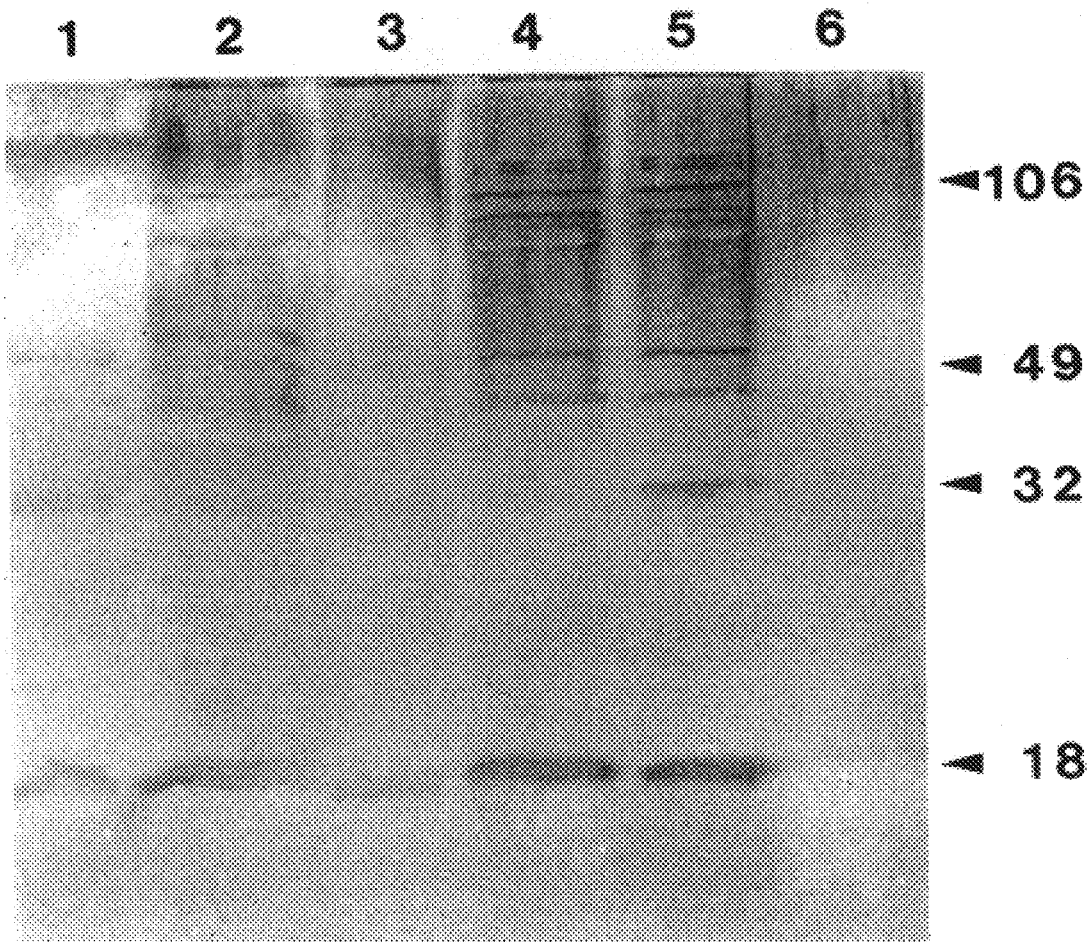
FIG. 6 shows a Western blot of OMPs of *A. pleuropneumoniae* serotype 1 grown in various media probed with sera from a pig exposed to low-dose challenge of *A. pleuropneumoniae* CM5.

FIG. 6 shows a Western blot of OMPs of A. pleuropneumoniae serotype 1 grown in various media probed with sera from a pig exposed to low-dose challenge of A. pleuropneumoniae CM5. Note the following in the Figure: OMPs of strain VSB68 grown in TSB aerobically (lane 1), strain CM5, TYE, aerobic (lane 2), CM5, TYE, anoxic (lane 3), CM5, RPMI, aerobic (lane 4), CM5, RPMI anoxic (lane 5), in vivo (lane 6). The positions and sizes of the molecular weight markers (in K) are indicated on the right.

In FIG. 6, sera from low-dose challenged pigs was used to probe blots of OMPs derived from cultures grown in the various media. No major differences in reactivity patterns were seen between OMP profiles from cells grown in TYE or RPMI. As mentioned above, it was not possible to adequately compare blotting profiles from bacterin and in vivo preparations due to the poor recovery of OMPs from the available material.

These experiments confirm that the expression of protein antigens of A. pleuropneumoniae can be altered by changing growth conditions (Deneer and Potter, 1989; Niven et al., 1989; O'Reilly et al., 1991).

In these experiments, in vivo cells recovered at necropsy from the pleural fluid of infected pigs were used as a standard for comparison of WC protein profiles of cells grown in vitro. Of the cultures studied, TYE grown cells had a WC protein profile most similar to that of the cells grown in vivo. On the other hand, RPMI and TSB WC profiles were quantitatively different from the in vivo standard. There were only minor quantitative differences in patterns from anoxic or aerobic paired samples grown in the same medium.

It was not possible to recover sufficient quantities of OMP-enriched fractions of in vivo and bacterin-derived cells to make a definitive comparison. Although there appeared to be minor quantitative differences in expression of major OMPs, no major differences in OMP pattern was seen between samples derived from different medium or growth conditions.

Of particular significance in this study was the finding that 103K and 105K proteins that were cell-associated could be detected in cells harvested from log-phase TYE broth culture. This confirms the work of Fedorka-Cray and others (1989) who determined that hemolysin and/or cytolysin is not only secreted into the culture medium but is also cell-associated. The nature of this association is not known, possibly involving transport across the cell membrane or attachment of the toxin molecule or precursor proteins before secretion.

This study indicates that the quantities of cell-associated cytolysin produced in culture are affected by the growth medium. Immunoblotting showed that cells from RPMI or TSB (bacterin) cultures were deficient in cell-associated cytolysin as compared to TYE cultures. Also, the expression of other cellular antigens was influenced by the growth medium. WC protein profiles of organisms grown in TYE broth were nearly identical to the in vivo standard. Therefore, TYE would be a preferred growth medium to produce a conventional WC bacterin which is enriched in cytolysin protein and contains WC antigens analogous to those found in vivo.

Example 2
Identification of Major Cellular Antigens Recognized by Immune and Control Sera To correlate the expression of key antigens in vitro to the recognition of those antigens by protected or susceptible animals, WC antigens, OMPs (outer membrane proteins) and partially purified cytolysins from *A. pleuropneumoniae* serotype 1 were separated by polyacrylamide gel electrophoresis and were examined by immunoblotting using sera from swine naturally exposed to *A. pleuropneumoniae* serotypes 1, 5, and 7. The sera used are listed in Table 8.

As well, these antigens were probed with sera from swine exposed to low-dose challenge, vaccinated with a commercial bacterin or control groups vaccinated with adjuvant or PBS placebo vaccines (Table 9).

Naturally Infected Animals

Figure 7:
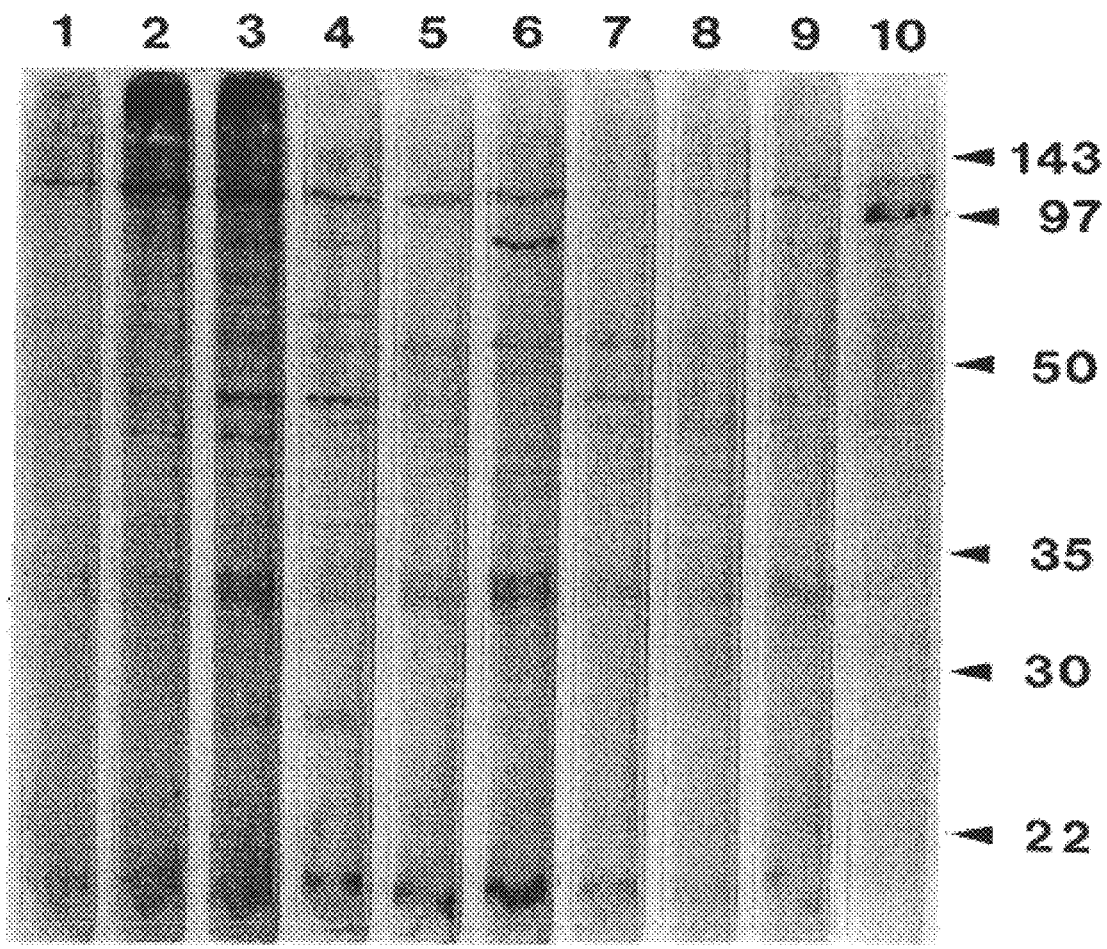
FIG. 7 shows a Western blot of WC proteins of *A. pleuropneumoniae* CM5 probed with sera from naturally-infected swine.

FIG. 7 shows Western blots of WC antigen preparations from *A. pleuropneumoniae* strain CM5 grown in TYE probed with sera from animals naturally infected with serotypes 1, 5, and 7. Note in FIG. 7, Serotype 1: serum #1438, #1458, and #1467 (lanes 1 to 3); Serotype 5: serum #5777, #5781, and #5682 (lanes 4 to 6); Serotype 7: serum #5816, #5818, and #5819 (lanes 7 to 9); Serum from a pig hyperimmunized with gel-purified cytolysin from CM5 (lane 10). The positions and sizes of the molecular weight markers (in K) are indicated on the right.

As shown in FIG. 7, all the sera recognized a predominant reactive band at 105K. However, the band which was apparent with serotype 1 and 5 antisera appeared as a distinct doublet (lanes 1 to 6), while the band recognized by serotype 7 antisera was a single line (lanes 7 to 9).

Figure 8:
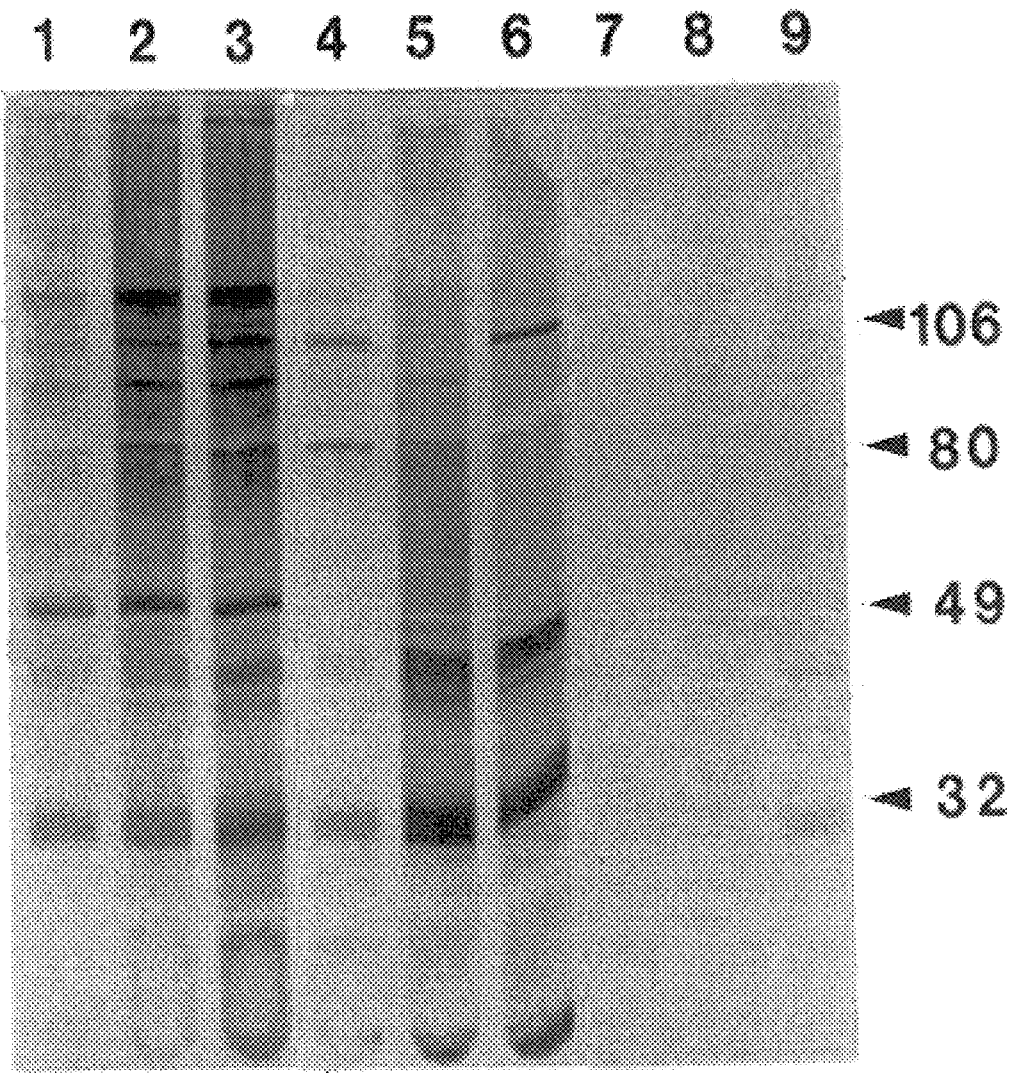
FIG. 8 shows a Western blot of OMPs of *Actinobacillus pleuropneumoniae* CM5 probed with sera from naturally-infected swine.

When the same sera were used to probe blots of OMPs of CM5, distinct differences were seen. FIG. 8 shows a Western blot of OMPs of *Actinobacillus pleuropneumoniae* CM5 probed with sera from swine naturally infected with serotype 1, serum #1438, #1458 and #1467 (lanes 1 to 3); serotype 5, serum #5777, #5781 and #5782 (lanes 4 to 6); serotype 7, serum #5816, #5818, and #5819 (lanes 7 to 9); Serum from a pig hyperimmunized with gel-purified cytolysin from CM5 (lane 10). The positions and sizes (in K) of the molecular weight markers is shown on the right.

FIG. 8 shows that sera from the homologous serotype, 1, recognized the majority of OMP bands (anes 1 to 3). Sera from serotype 5 recognized fewer bands at 72K and 106K (lanes 4 to 6), while sera from serotype 7 did not seem to recognize any of the OMPs of serotype 1 Lanes 7 to 9).

Vaccinated Animals

Figure 9A:
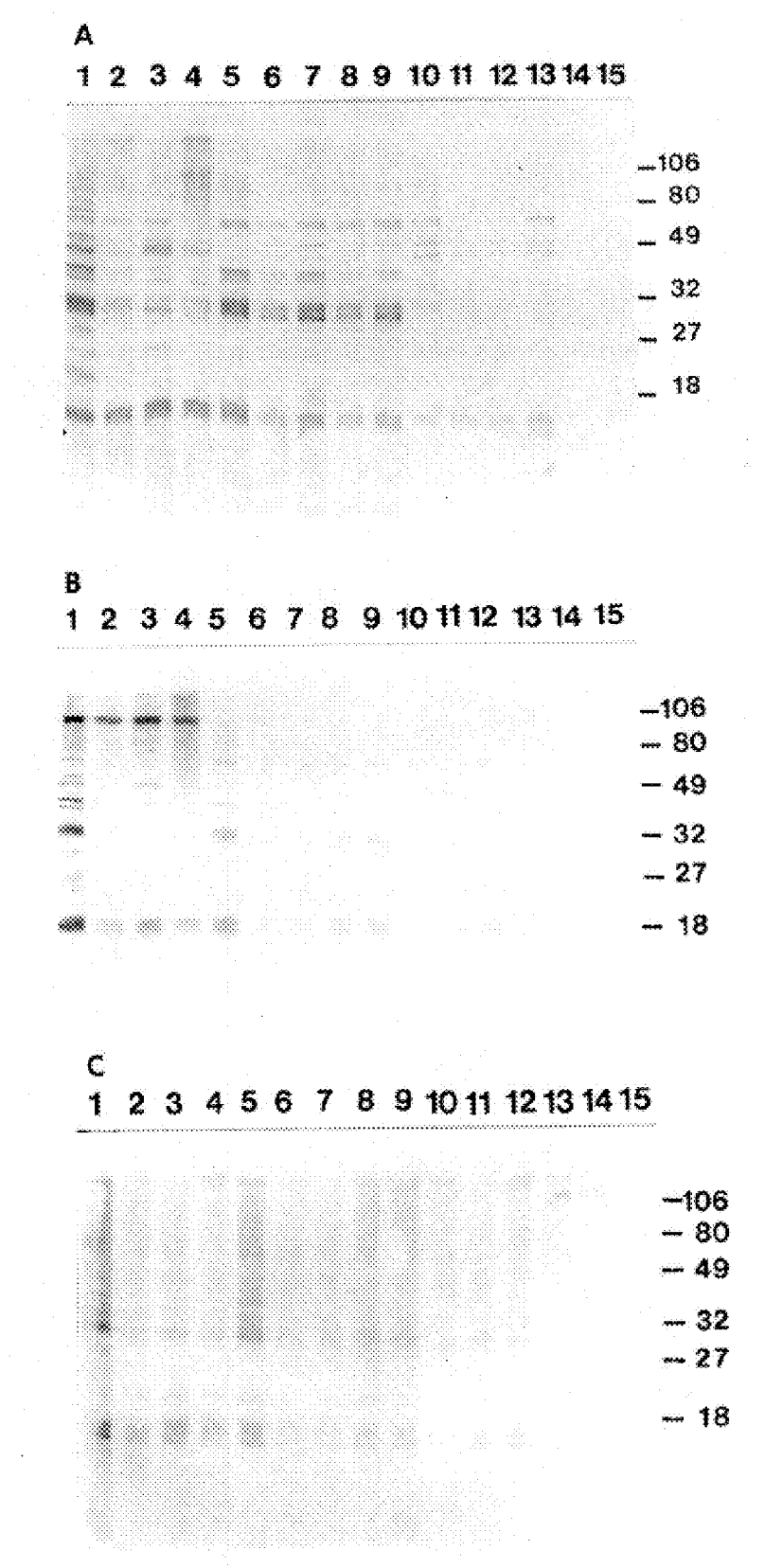
Figure 9B:
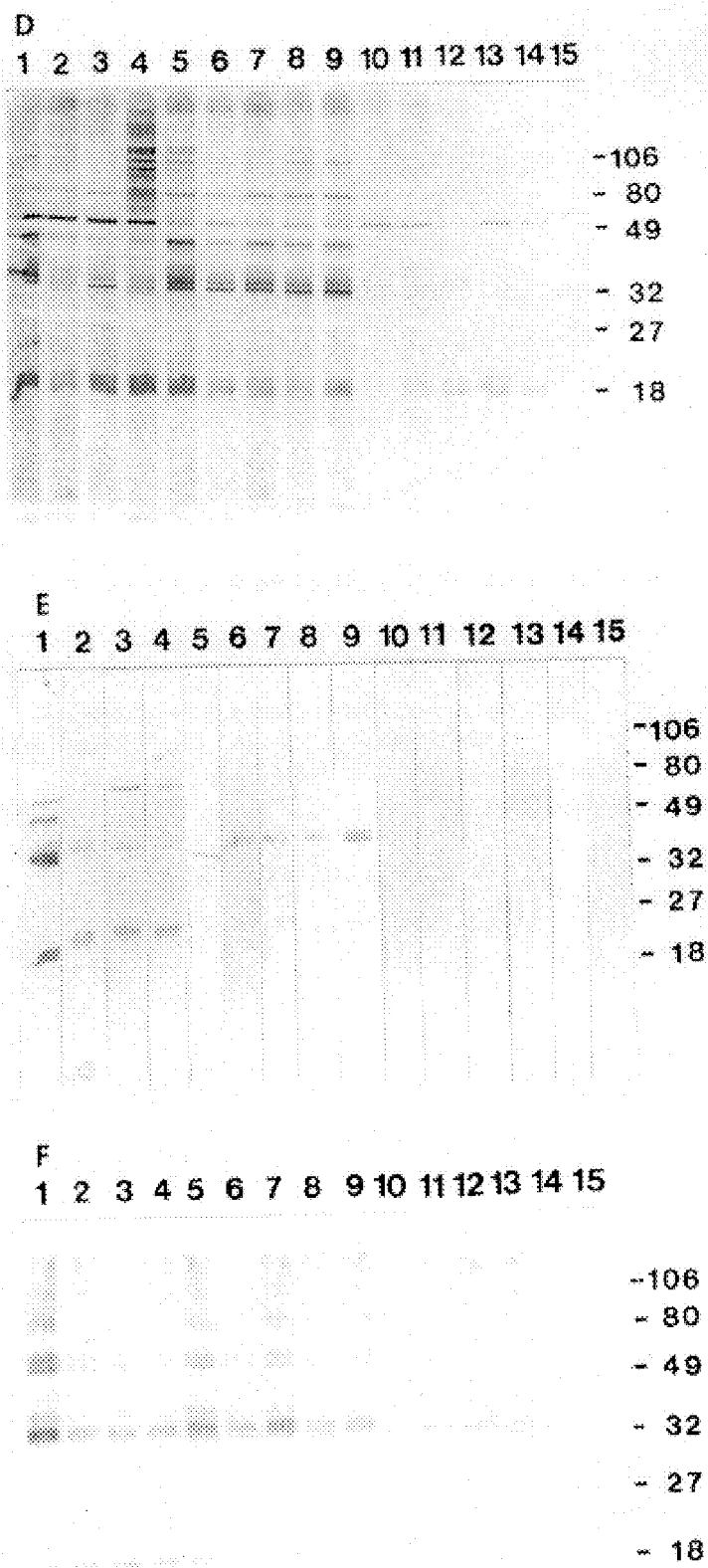
FIG. 9 as depicted in FIGS. 9a and 9b, shows Western blots of WC proteins of *A. pleuropneumoniae* serotype 1 strain CM5 grown in RPMI (A); and in TYE (B); and WC proteins of *A. pleuropneumoniae* serotype 1 strain VSB68 in TSB (C); Western blots of outer-membrane proteins *A. pleuropneumoniae* serotype 1 strain CM5 grown in RPMI (D); in TYE (E); and Western blots of outer-membrane proteins *A. pleuropneumoniae* serotype 1 strain VSB68 grown in TSB (F)

FIG. 9, Panels A to F show Western blots of WC proteins of *A. pleuropneumoniae* serotype 1 strain CM5 grown in RPMI (A), CM5, TYE, (B), VSB68, TSB (C), and outer-membrane proteins from CM5 grown in RPMI (D), CM5, TYE (E), VSB68, TSB (F). The blots were probed with swine sera from low-dose vaccinated animals #A4-3, #A9-3, #B14-3, and #B15-3 (lanes 1 to 4), commercial bacterin vaccinated animals #A3-3, #A11-3, #B19-3, #B20-3, and #B21-3 (lanes 5 to 9), PBS control animals #A10-3, and #B16-3 (lanes 10 to 11), adjuvant control animals #A6-3, #A8-3, #B8-3, and #B22-3 (lanes 12 to 15). The positions and sizes (in K) of the molecular weight markers are shown on the right.

FIG. 9, Panel A, lanes 1 to 4, 5 to 9, 10 to 11, and 12 to 15, respectively show the results of the studies where sera from pigs exposed to a low-dose challenge, vaccinated with a commercial *A. pleuropneumoniae* bacterin, or PBS, or adjuvant, were used to probe WCs proteins from strain CM5 grown in RPMI. Aside from minor variations between individual pigs, the sera from the bacterin and low-dose vaccinates recognized the same pattern of WC proteins, while control sera from PBS and adjuvant treated animals reacted only weakly. However, when the same sera were used to probe WC proteins from cells grown in TYE medium, a significant difference in the antigen recognition pattern was evident (FIG. 9, Panel B). An intensely stained doublet at approximately 105K was recognized by the low-dose sera (FIG. 9, Panel B, lanes 1 to 4) but not by any other sera. Immunoblots of WC proteins from VSB68 grown in TSB (bacterin) were poorly reactive when probed with the same sera (FIG. 9, Panel C). No apparent differences in reactivity were detected with any of the sera.

Sera from low-dose (lanes 1 to 4) and bacterin (lanes 5 to 9) vaccinated animals reacted similarly in blots of OMPs from CM5 grown in RPMI (FIG. 9, Panel D). Wide, densely stained bands were seen at 17K and 32K, as well as bands at 40–42K, 72K and 106K. All the sera, including control sera, reacted with a band at approximately 55K. In contrast, when Western blots of OMPs from CM5 grown in TYE were probed with sera from low-dose, commercial bacterin vaccinates and controls, some differences were seen (FIG. 9, Panel E). Sera from low-dose vaccinates recognized 4 or more OMPs at 72K, 42K, 40K and 26K (lanes 1 to 4), while sera from bacterin vaccinates recognized only lower molecular weight OMPs at 40K and 26K (lanes 5 to 9). Control sera were non-reactive. None of the sera reacted well with OMPs from VSB68 grown in TSB (bacterin) (FIG. 9, Panel F). Except for weak reactions with the 32K OMP band shown by sera from low-dose (lanes 1 to 4) and bacterin (lanes 5 to 9) vaccinates, the sera were non-reactive.

Figure 10:
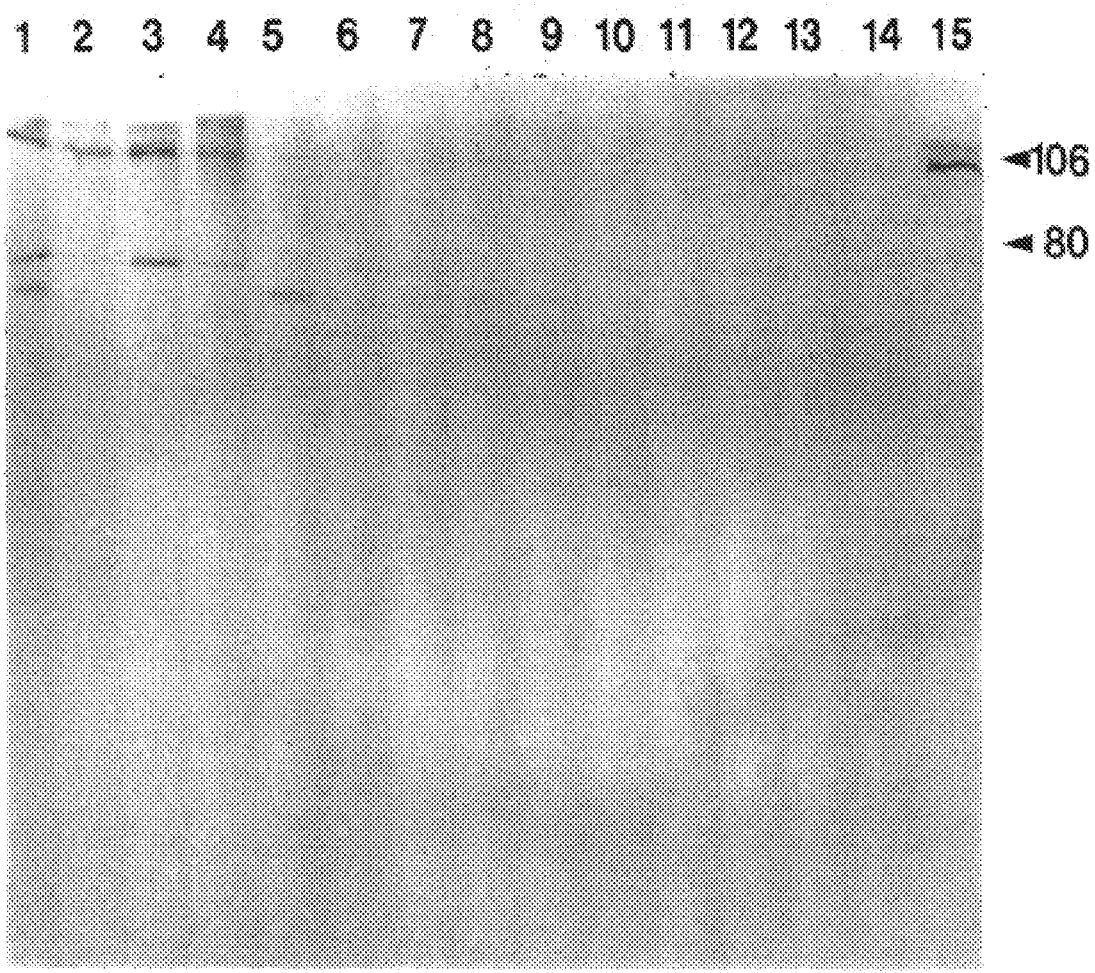
FIG. 10 shows a Western blot of CYT from CM5 probed with sera from CDCD pigs.

In order to confirm the identity of the 105K bands seen in the blots of the TYE grown cells, the same sera were used to probe a partially purified cytolysin preparation from CM5. FIG. 10 shows a Western blot of CYT from CM5 probed with sera from CDCD pigs exposed to low-dose challenge of *A. pleuropneumoniae* CM5 (lanes 1 to 4), vaccinated with a commercial bacterin (lanes 5 to 9), vaccinated with PBS (lanes 10 and 11), vaccinated with adjuvant (lanes 12 to 14), CYT positive control sera (lane 15). The positions and sizes (in K) of the molecular weight markers is shown on the right. As shown in FIG. 10, similar 105K bands were recognized by the sera from the low-dose vaccinates (lanes 1 to 4), but not with the sera from commercial bacterin (lanes 5 to 9), PBS (lanes 10 and 11), or adjuvant vaccinated animals (lanes 12 to 14).

Inactivation

The effect of the inactivation procedure on the reactivity of WC antigens from serotype 1 and serotype 3 grown in TYE was compared by immunoblotting. FIG. 11A and FIG. 11B show Western blots of WC proteins of A. pleuropneumoniae probed with serum from a pig hyperimmunized with gel-purified CYT (FIG. 11A), or serum from a pig exposed to low-dose challenge (FIG. 11B). Note the following in the Figures: Strain BC181 serotype 3 (lanes 1 to 4), strain CM5 serotype 1 (lanes 5 to 8). Formalin inactivated (lane 1 and 5), beta-propiolactone inactivated (lanes 2 and 6), binary-ethyleneimine inactivated (lanes 3 and 7), heat-inactivated (lanes 4 and 8). The positions and sizes (in K) of the molecular weight markers is shown on the right.

As shown in FIG. 11, only minor variations in the reactivity of the major 105K band were seen when cells inactivated with the chemical agents formaldehyde, BPL and BEI (lanes 1 to 3 and 5 to 7) were compared to heat-inactivated preparations (lanes 4 and 8).

In North America, the three serotypes of A. pleuropneumoniae most commonly causing disease are 1, 5, and 7. Kamp et al., (1991) confirmed that these three serotypes produce a 103K cytolysin, ApxII, and that serotypes 1 and 5 produce a 105K cytolysin, ApxI. Sera from pigs naturally exposed to the individual serotypes were used to identify the key antigens in these serotypes. Immunoblotting experiments confirmed that IgG antibodies to the ApxI and ApxII cytolysins of A. pleuropneumoniae serotype 1 were common and conspicuous in these sera.

There was less consistency in the antigens recognized in OMP-enriched preparations. Homologous sera reacted well, however sera from serotype 5 infected animals detected fewer OMP antigens of serotype 1, while sera from serotype 7 infected animals were non-reactive. This is in contrast to cross-reactivity seen with serotype 1 to 8 hyperimmune rabbit sera (MacInnes and Rosendal, 1987). It may be that less virulent serotypes such as serotype 7 do not stimulate as strong an immune response as the more virulent serotypes.

There are consistant differences in the reactivity of sera from low-dose infected animals as compared to bacterin vaccinates. The sera from animals vaccinated with the commercial bacterin lacked the antibodies to the ApxI and ApxII cytolysins whereas sera from animals that had recovered from infection had high levels of anti-cytolysin antibodies. Also, the response to commercial vaccine appeared to favour production of antibodies to lower molecular weight antigens as seen in the immunoblots (FIG. 7C, lanes 1 to 5).

In general, the quality of the commercial antigen was poor. In the blotting experiments, protein bands were consistantly diffuse and fuzzy, independent of the antibody used to probe the blots. This could be the result of the use of formalin as an inactivating agent. The chemical cross-linking of proteins likely interferes with electrophoresis, transfer, and antibody binding.

These experiments highlight a consistent difference in antibody response between animals infected with A. pleuropneumoniae and animals vaccinated with a commercial inactivated-WC bacterin. The response of infected animals to the cytolysins of A. pleuropneumoniae is likely a marker for protective immunity, in contrast to the lack of response to these proteins by vaccinated animals.

Therefore, the protective efficacy of a WC bacterin may be improved if the level of immunogenic cytolysin could be increased. The evaluation of experimental bacterins based on TYE grown cell is described below.

Example 3

Vaccination of Pigs with Experimental Bacterins

One of the objectives of the investigations described herein was to improve the protection afforded by a conventional WC A. pleuropneumoniae bacterin. By evaluating the expression of cellular antigens in various media under different growth conditions and comparing the response patterns of protected and susceptible pigs, a method of culturing and inactivating A. pleuropneumoniae to produce and conserve important antigens was developed. Experimental bacterins were prepared (as described above) and used to vaccinate CDCD and conventional pigs in two separate challenge experiments. The protection afforded by the vaccines was evaluated by measuring clinical signs, gross pathological examination, bacteriological culture, and by serological evaluation of blood samples collected throughout the trials.

Trial One—Caesarian Derived, Colostrum Deprived Pigs

All of the piglets receiving adjuvant placebo treatment and four of the five pigs given PBS were euthanized with severe clinical signs within 24 h after challenge. The remaining PBS-treated pig was euthanized at day 10. The group receiving the conventional bacterin were all euthanized within 24 h of challenge. One of the pigs exposed to a low-dose of A. pleuropneumoniae developed severe clinical disease and had to be euthanized prior to challenge. This pig was excluded from the study. The remaining low-dose piglets and the piglets receiving Bacterin A all survived challenge.

Figure 12:
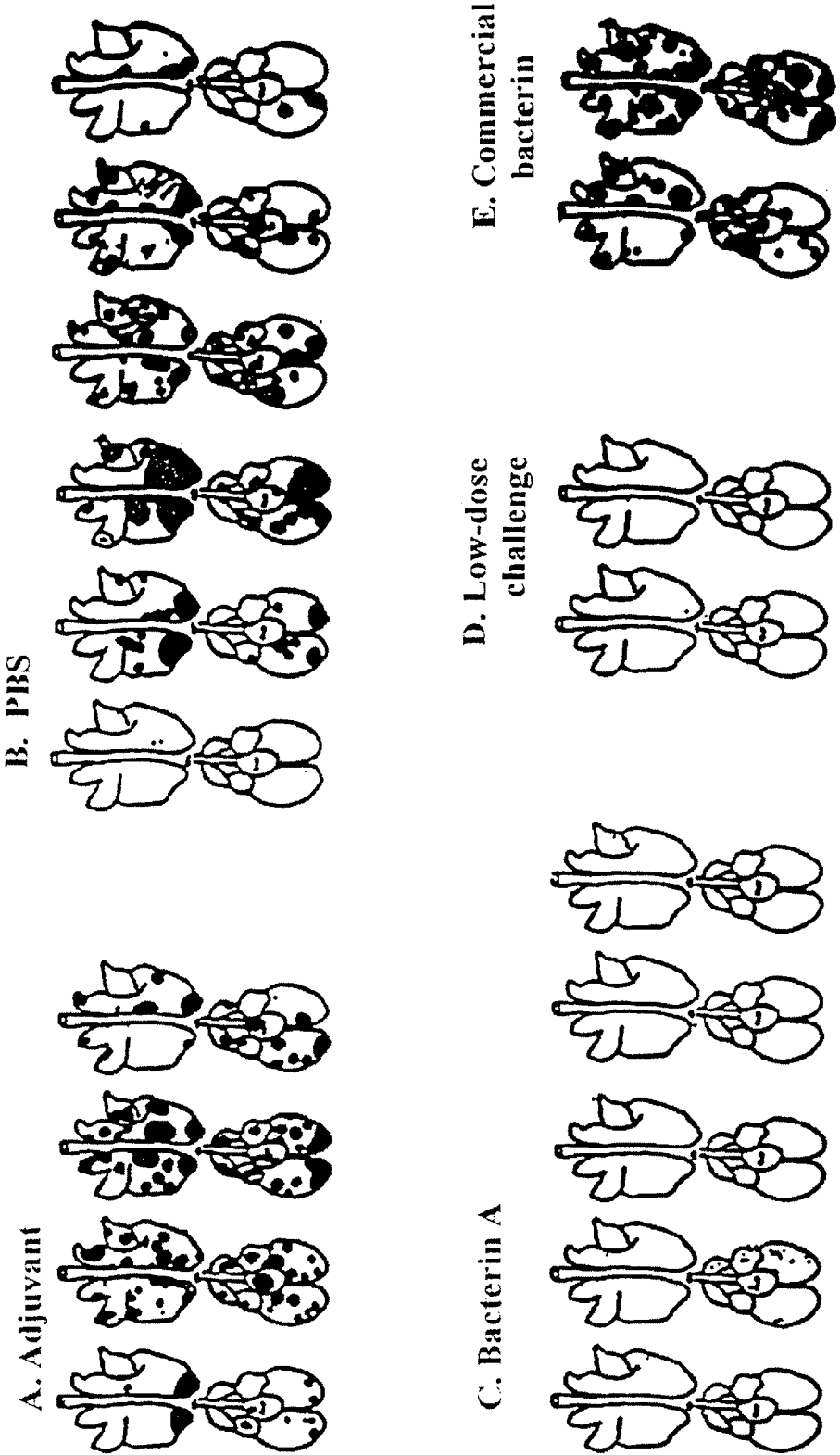
FIG. 12 shows the distribution of lung lesions of the CDCD pigs at necropsy.

The lung scores of the pigs at necropsy are presented in Table 10 and the lung lesions are depicted in FIG. 12. In FIG. 12, the treatment groups are as follows (A) adjuvant, (B) PBS, (C) bacterin A, (D) low-dose challenge, (E) commercial bacterin. The low-dose and experimental vaccine groups had similar, very low lung lesion scores with means of 0.5 and 0.4 respectively. In contrast, the pigs vaccinated with the commercial bacterin had lesions similar to those of PBS or adjuvant control groups. The means for these groups were 5.5, 4.0, and 6.0 respectively.

Statistically there was no significant difference between the mean lesion scores of the low-dose and bacterin A treatment groups (p=0.5). Also, the mean lesion score for the commercial bacterin group was significantly different from those of the low-dose and bacterin A treatment groups, but was not significantly different from adjuvant and PBS control groups.

Figure 13:
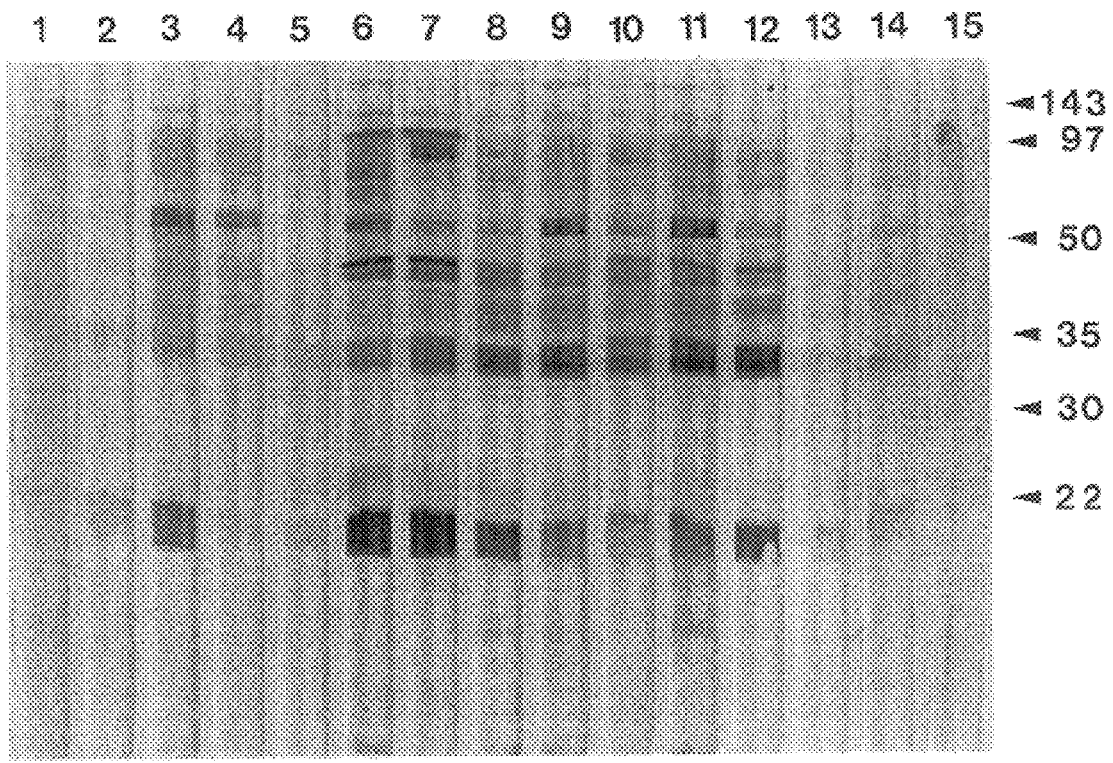
FIG. 13 shows a Western blot of WC proteins of *A. pleuropneumoniae* probed with sera from CDCD pigs.

Western blot analysis of WC proteins from A. pleuropneumoniae CM5 probed with the sera from the various treatment groups is presented in FIG. 13. In particular, FIG. 13 shows a Western blot of WC proteins of A. pleuropneumoniae probed with sera from CDCD pigs vaccinated with adjuvant (lanes 1 to 4), PBS (lane 5), low-dose challenge (lanes 6 and 7), Bacterin A (lanes 8 to 12), commercial bacterin (lanes 13 and 14), and CYT positive control serum (lane 15). The positions and sizes (in K) of the molecular weight markers are shown on the right.

As shown in FIG. 13, the sera from two low-dose vaccinates recognized prominant bands at 105K, 72K, 45K, 32K and 17K (lanes 6 and 7). The sera from the experimental bacterin-treated pigs had nearly identical profiles to those of the low-dose sera except there was a less intense reaction at 105K (lanes 8 to 12). The antigen recognition of the sera from pigs vaccinated with commercial bacterin was extremely poor (lanes 13 and 14), and not very different to that seen with the sera from the PBS (lane 5) and adjuvant treated (lanes 1 to 4) control animals.

Figure 14:
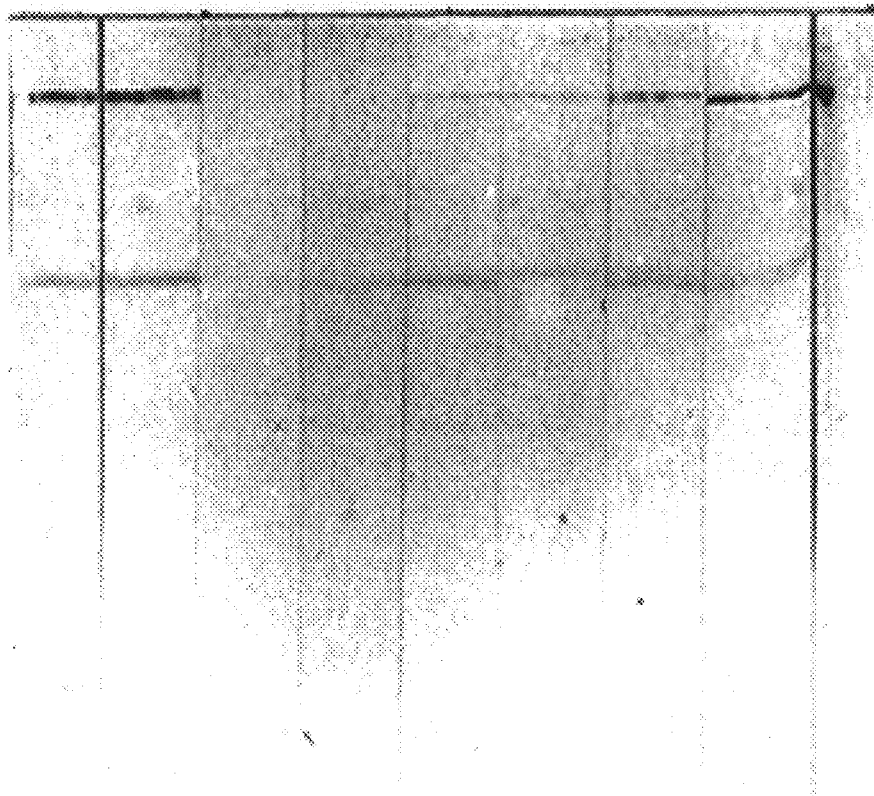
FIG. 14 shows a Western blot of CYT probed with sera from vaccinated pigs.

An immunoblot of purified CM5 CYT probed with sera from the vaccinated pigs in Trial 1 is shown in FIG. 14. The low-dose pig sera recognized the 105K and 103K antigen band (lanes 1 and 2), as did the sera from the pigs given experimental bacterin A (lanes 5 to 8). In contrast, sera from pigs given the commercial bacterin did not react with the CYT from CM5 (lanes 3 and 4). The haemolysin control is shown in lane 9. The positions and sizes (in K) of the molecular weight markers are shown on the right in FIG. 14.

ELISA titres of the sera are presented in Table 12. The low-dose group had a significant response to CYT (0.800), as did the Bacterin A pigs (0.264). The response of the pigs vaccinated with commercial bacterin (0.069) was not significantly different from that of the PBS or adjuvant control groups. Except for the Bacterin A pigs, the response to LPS and CPS was not signifcant.

Trial Two—SPF Pigs

Figure 15:
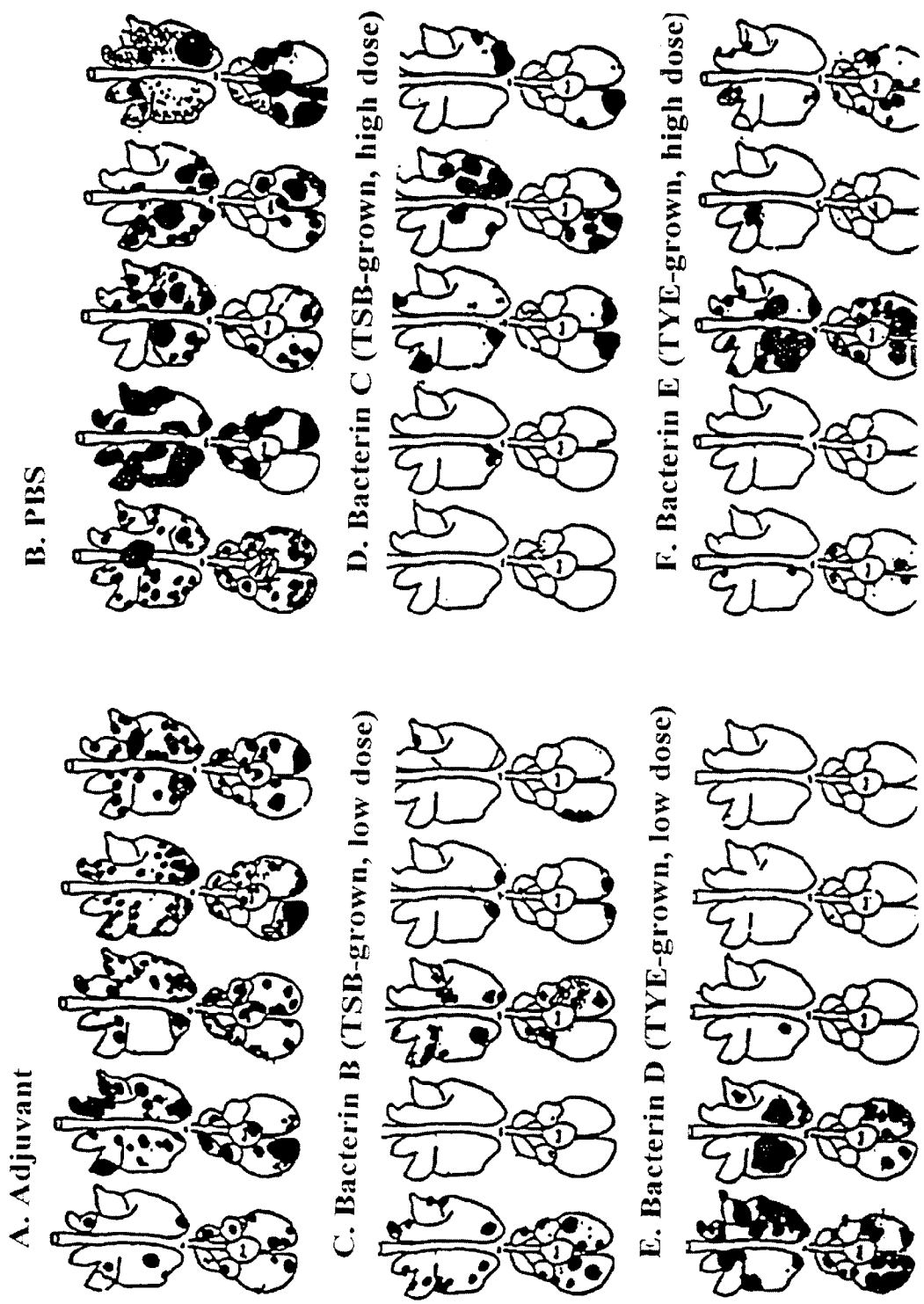
FIG. 15 shows the distribution of lung lesions of the SPF pigs at necropsy.

In a second trial, commercially-reared SPF pigs, 4 weeks of age were vaccinated with experimental bacterin preparations B, C, D, and E. Table 13 summarizes lung scores, lung/heart weight ratios, lung culture results, and weight gain or loss for the animals surviving to day 5. The distribution of lung lesions is pictured in FIG. 15. (In FIG. 15, the treatment groups shown are as follows (A) adjuvant, (B) PBS, (C) bacterin B, (D) bacterin C, (E) bacterin D, (F) bacterin E.) All 5 pigs that received adjuvant showed severe clinical signs within 24 h post-challenge and were euthanized. Three of five PBS vaccinated animals also showed severe clinical signs within 24 h post-challenge and were euthanized. The remaining two PBS-treated animals developed severe respiratory distress at day 2 and day 4 respectively and were euthanized.

Of the four vaccine treatment groups, all five pigs in groups B and C survived and were euthanized 5 days post-challenge. One animal in group D developed significant respiratory symptoms at day 1 and was euthanized. However, at post-mortem lung lesions were less remarkable than those of the control animals. The four remaining animals in group D survived to day 5. In group A, three of five animals developed disease and were euthanized between days 1 and 3. The remaining two pigs survived to day 5.

Statistical analysis of mean lung scores and lung/heart weight ratio showed similar results. There was a significant difference between mean scores for the adjuvant and PBS treatment groups compared to all four bacterin treatment groups. There was no significant difference in mean lung lesion or lung/heart ratio scores of any of the bacterin treatment groups. The control groups were not significantly different from each other.

Table 14 summarizes the serological ELISA results for CYT, LPS and CPS. In contrast to the results of trial 1, all of the animals receiving bacterin treatments responded significantly to LPS and CPS, in addition to CYT, as compared to the PBS and adjuvant treatment groups.

There was no difference in response to LPS between bacterin groups B, C, and E. Bacterin D induced an LPS response that was statistically significantly better than that of bacterin C, but not significantly different from that of bacterins B and E. Exactly the same pattern of significance was seen when response to CPS was compared.

Statistical analysis of CYT responses showed a slightly different response. The CYT titre to bacterin D was significantly higher than that of bacterins B, C and E. The response to bacterin E was better than the response to bacterin C, but not significantly different than the response to bacterin B. There was no difference in the CYT responses to bacterins B and C.

Figure 16A:
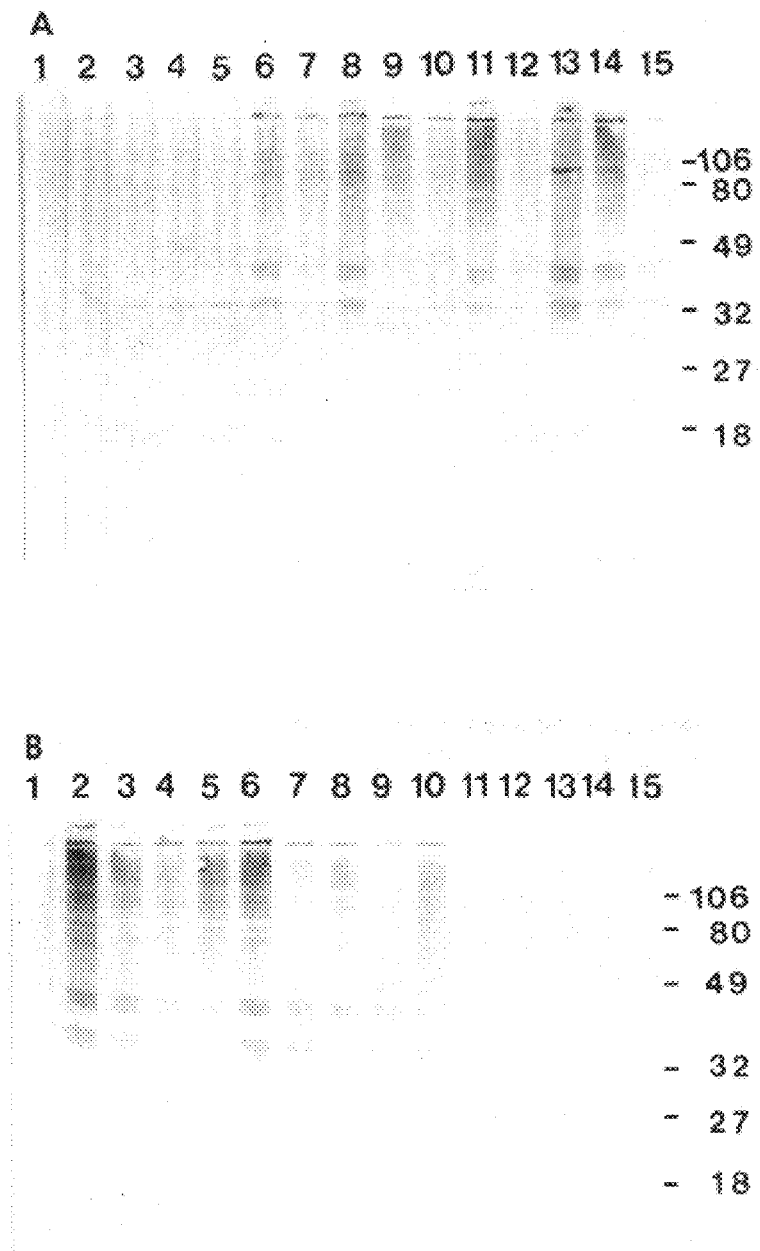
FIG. 16 as depicted in FIGS. 16a and 16b, shows Western blots of WC proteins (A and B) and CYT (C and D) probed with sera from vaccinated SPF pigs.
Figure 16B:
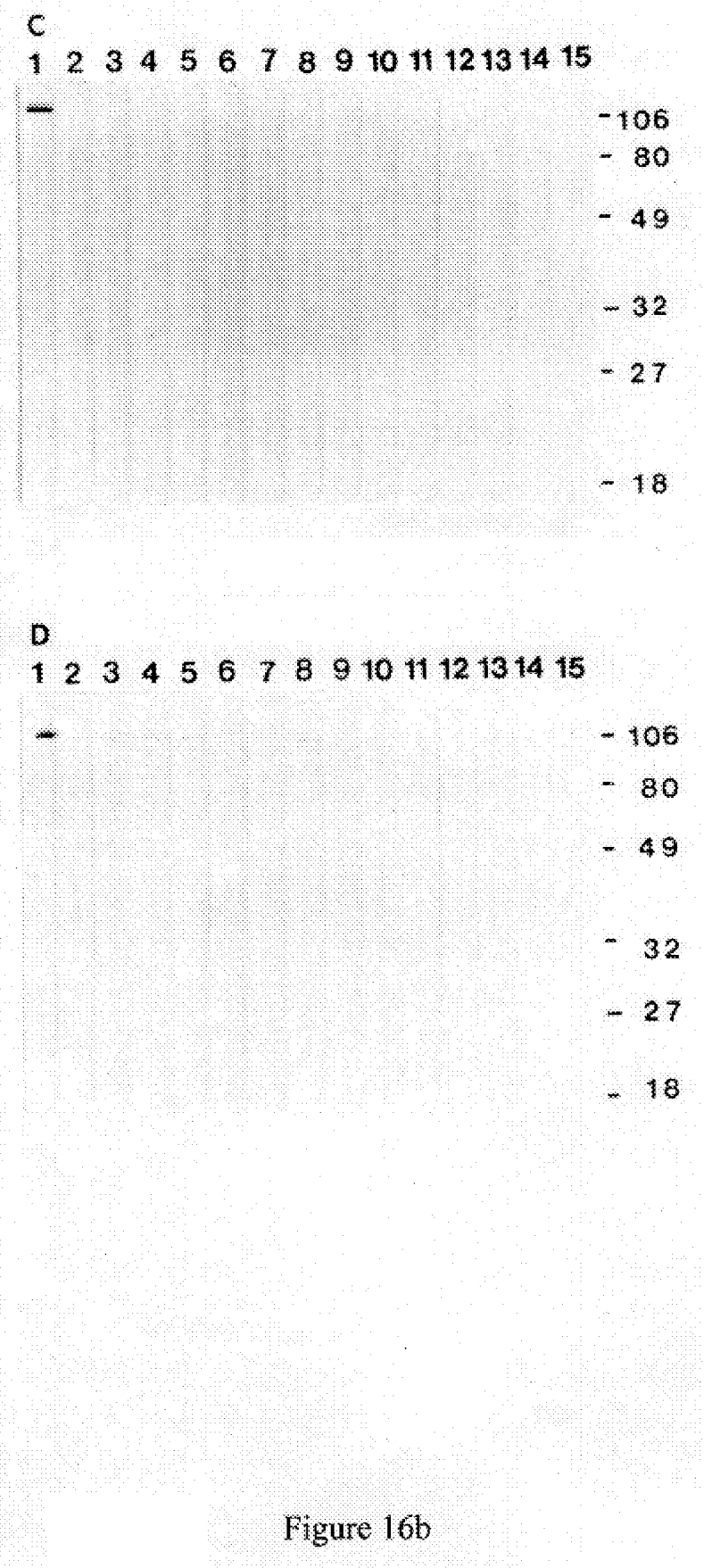
Figure 17:
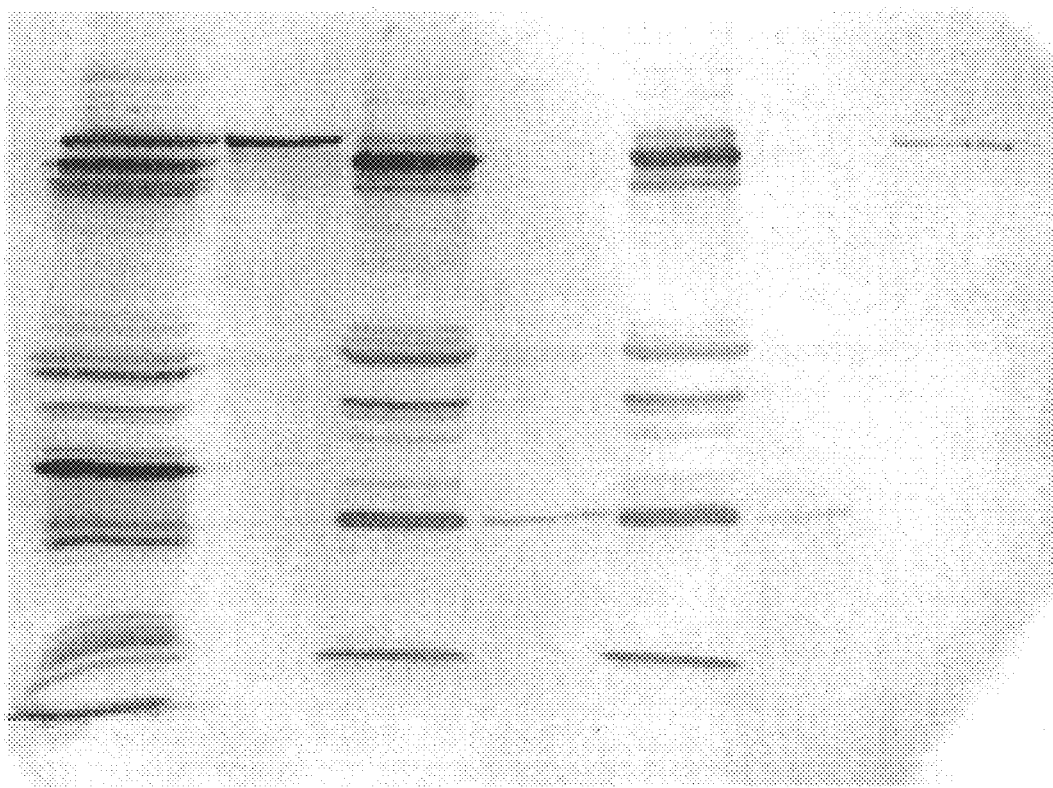
FIG. 17 shows Western Blots of WC proteins of CM5 (lane 1), transposon mutant #17 (lane 3), and transposon mutant #18 (lane 5), the corresponding culture supernatants (lanes 2, 4, and 6), and purified CYT (lane 7)
Figure 18:
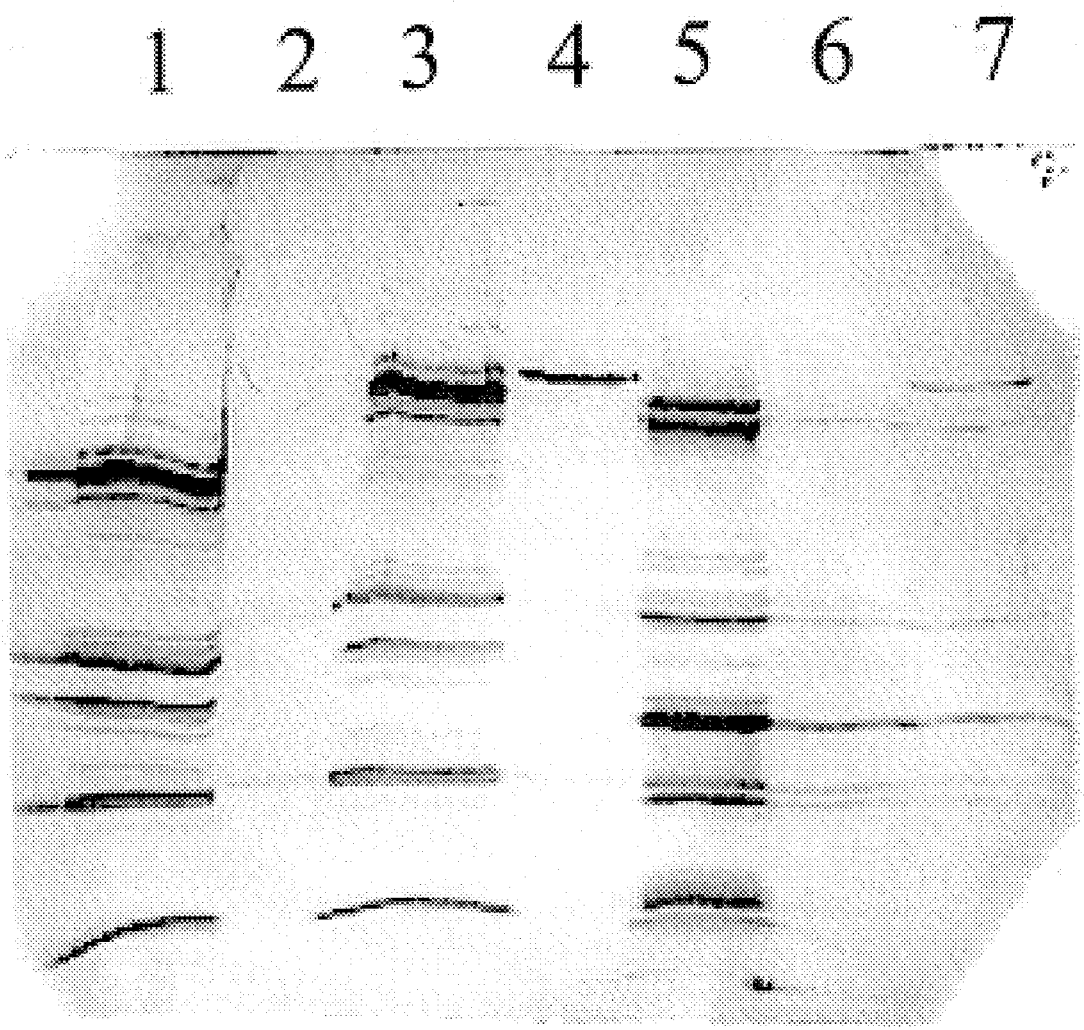
FIG. 18 shows WC preparations of transposon mutant #19 (lane 1), control transposon mutant #20 (i.e., not a BD mutant) (lane 3), serotype 3 strain BC181 (lane 5), the corresponding culture supernatants (lanes 2, 4 and 6), and purified CYT (lane 7)
Figure 19:
FIG. 19 shows WC preparations of CM5-JB, a low passage variant (lane 1), transposon mutant #17 (lane 3), and transposon mutant #18 (lane 5), the corresponding culture supernatants (lanes 2, 4, and 6), and purified CYT (lane 7).

Western blots of WC and column-purified cytolysins probed with post vaccination sera from these pigs are presented in FIG. 16. In particular, FIG. 16 shows Western blots of WC proteins (A and B) and CYT (C and D) probed with sera from vaccinated SPF pigs. Note the following in the Figure: WC proteins probed with sera from pigs vaccinated with adjuvant (A, lanes 1 to 5), bacterin B (A, lanes 6 to 10) bacterin C (A, lanes 11 to 15), bacterin D(B, lanes 1 to 5), bacterin E (B, lanes 6 to 10), PBS (B lanes 11 to 15). CYT probed with sera from pigs vaccinated with CYT positive control (C and D, lane 1) adjuvant (C, lanes 2 to 5), bacterin B (C, lanes 6 to 10), bacterin C (C, lanes 11 to 15), bacterin D (D, lanes 2 to 6), bacterin E (D, lanes 7 to 11), PBS (C, lanes 12 to 15).

As expected, sera from pigs vaccinated with PBS (Panel B, lanes 11 to 15; Panel D, lanes 12 to 15) or adjuvant (Panel A, lanes 1 to 5; Panel B, lanes 2 to 5) gave almost no reaction with WC or CYT blots. Sera from pigs vaccinated with the experimental bacterins, B (Panel A, lanes 6 to 10), C (Panel A, lanes 11 to 15), D (Panel B, lanes 1 to 5), and E (Panel B, lanes 6 to 10), gave similar reactions with blots of WC protein. Differences were most obvious in the blots of CYT probed with these sera. In these blots, sera from bacterin D (Panel D, lanes 2 to 6) recognized the 105K bands that correspond to the cytolysins of CM5. Also, the sera from animals vaccinated with bacterin E (Panel D, lanes 7 to 11), also recognized these 105K bands, although more weakly.

For many years it has been reported in the literature that, at best, commerdal WC bacterins provide only partial, serotype-specific protection against morbidity and mortality in swine following infection with A. pleuropneumoniae (Neilson, 1984; Fedorka-Cray et al., 1990). In contrast, animals that recover from natural infection have solid cross-protective immunity.

In vaccine trial 1, experimental bacterin A containing heat-killed, TYE-grown cells and the proprietary adjuvant L80, was effective in providing protection against experimental challenge with the homologous strain. The mean lung score for the bacterin A group was not statistically different from that of the low-dose challenge group in which clinical disease was not observed. In comparison, the commercial bacterin was completely ineffective in providing protection against disease. The mean lung score for the commercial bacterin group was not statistically different from those of the PBS or adjuvant treated groups. This result is consistent with previous experimental results obtained with the commercial bacterin in five separate litters of CDCD pigs tested in separate experiments (Furesz, S. and B. Mallard, University of Guelph, unpublished data).

ELISA titres of sera from protected animals showed that bacterin A induced a marked anti-cytolysin response in vaccinated animals, but no titres to LPS or CPS. Immunoblots confirmed that sera from the protected animals recognized the 103K and 105K cytolysins and that these cytolysins were not recognized by sera from control animals or pigs that received the commercial vaccine. The association of anti-CYT response with protection is similar to the findings in previous studies showing that IgG response to CYT is necessary for protection (Rycroft et al., 1991; Bhatia et al., 1991; Inzana et al., 1991; Fedorka-Cray et al., 1990).

In addition to the changes of growth medium and inactivation methodology, the experimental bacterin used in the first trial differed from the commercial bacterin in several other ways. There were only two serotypes of A. pleuropneumoniae in the experimental vaccine, compared with four serotypes in the commercial product. The cell concentration in the experimental vaccine was higher than that of the commercial preparation, and the experimental vaccine contained an adjuvant which differed from the one in the commercial bacterin. Some, or all of these additional factors may have been important in the increased efficacy of the experimental vaccine over the commercial product.

The rationale for including both serotype 1 and 3 strains in bacterin A was the fact that these serotypes together produce all 3 *A. pleuropneumoniae* RTX toxins. Recent work by Frey et al. (1994, submitted for publication) showed that serotype 3 strains of *A. pleuropneumoniae* do not contain the apxIB and D genes which encode proteins that are responsible for ApxII secretion in other serotypes.

The second trial was designed to limit the number of variables between vaccines by eliminating serotype, antigen concentration, inactivation and adjuvant variables in the hopes of identifying which factor(s) were most important in improving bacterin performance. In vaccine trial 2, SPF pigs, determined to be susceptible to challenge with *A. pleuropneumoniae*, were used to compare monovalent experimental bacterins prepared from the serotype 1 strain of *A. pleuropneumoniae* used in the commercial bacterin. Low and high antigen content bacterins were prepared using either the TSB-grown, heat-killed cells prepared using production methodology for the commercial bacterin, or TYE-grown, heat-killed cells prepared using the production methodology described for bacterin A.

Compared to controls, all four vaccines provided significant protection against aerosol challenge with a different serotype 1 isolate. In contrast to the findings of trial 1, serum ELISA titres to the four experimental preparations showed significant responses to LPS and CPS in addition to CYT. Since the SPF animals used in this experiment were conventionally-reared pigs, it is possible that they had some previous exposure to organisms with cross-reacting antigens that allowed them to produce an anamnestic response to LPS and CPS. In contrast to the commercial bacterin-treated group, all of the animals in the four experimental vaccine groups had a significant immunity to challenge. This is perhaps accounted for by the use of a more effective adjuvant in this group of vaccines as compared to the commercial bacterin. As shown by the ELISA data, all animals had IgG antibody responses to LPS, CPS, and CYT. The response to CYT was significantly better in the TYE bacterin groups than in the TSB bacterin groups, while the responses to LPS and CPS were only significantly different between high dose TSB and low-dose TYE groups.

Antibody responses to high and low-doses of antigen were not significantly different for LPS and CPS within bacterin types. However, antibody response to CYT was significantly better in the lower dose TYE bacterin group compared to the high dose TYE bacterin group. This suggests that there may be an optimum dose of CYT which is titratable or alternately that antigen/adjuvant ratios were not optimum in the higher dose antigen vaccines.

Example 4
PROTOCOL RE HETEROLOGOUS CHALLENGE

The test animals which will be used in this study are conventionally raised specific pathogen free swine from a high health status herd, 4–5 weeks of age, and free of antibody to *A. pleuropneumoniae*. Three or more groups of 10–15 animals will be used in the study. The animals ar identified by numbered ear tags. The animals are fed conventional swine ration without antibiotics. The swine will be given 2 doses of each test preparation (*A. pleuropneumoniae* experimental bacterin, adjuvant placebo, and PBS) administered intramuscularly 3–4 weeks apart. The animals will be weighed at second vaccination and at post mortem. At post mortem heart and lung weights are recorded for lung/body weight ratios. Blood samples are taken prior to the start of vaccinations at each vaccination, prior to challenge and at post mortem for serological analysis. Animals are observed several times daily prior to vaccination. Animals are also observed closely for several hours post-vaccination for adverse reactions such as anaphylaxis, vomiting, anorexia, diarrhea, lameness, fever, or malaise. Post challenge animals are observed at least every 3 hours for signs of disease. At post mortem, lung lesions are recorded and scored according to a standardized scoring system. The “least squared means” analysis statistical method will be employed to analyze serological scores and clinical scores.

Example 5

Creation of BD Mutants

A suicide conjugative plasmid, pLOFKm, carrying a mini-Tn10 was used for transposon mutagenesis of *A. pleuropneumoniae* CM5 as described by Tascon et al, Bacteriol. 175:5717–5722 (1993). The plasmid was mobilized from *E. coli* to *A. pleuropneumoniae* by biparental mating. Transconjugants were screened on blood agar plates, and non-hemolytic mutants were selected. Four non-hemolytic mutants were selected for further analysis.

Southern Blot Analysis of Non-hemolytic Mutants

Chromosomal DNA was extracted from the transposon mutants, digested with restriction enzymes, separated by electrophoresis on 0.7% agarose gels, and transferred to nylon membranes using conventional procedures (Sambrook et al. Molecular doning—A Laboratory Manual 2nd edition. Cold Spring Harbor Laboratory Press, Cold Spring Harbor, (1989)). The membranes were probed with a PCR-generated 1.4 kb fragment which included part of the BD gene region, and with the mini-Tn10. The probes were labelled using the non-radioactive DNA detection kit from Boehringer Mannheim. Hybridisations were performed under stringent conditions (Sambrook et al. supra).

Southern blots of chromosomal DNA from the parent strain and the mutants digested with BglII, EcoRI, and XhoI, and probed with the BD region probe, demonstrated transposon insertion in the BD region. This was indicated by an increase in size of the probe-reactive fragments in the mutants, when compared to the corresponding fragments in the parent strain. The presence of a single copy of the transposon in the mutants was confirmed by probing XhoI digests of chromosomal DNA with the mini-Tn10.

Western Blots

Transposon mutants with insertions in the apxIBD genes export little or no CYT and contain 105K cell-associated CYT. Western blots of WC, culture supernatant, and column-purified hemolysin probed with antibodies made to gel-purified CYT from strain CM5 are presented in FIGS. 17 to 19. The cultures were grown in TYE.

FIG. 17 shows WC proteins of CM5 (lane 1), transposon mutant #17 (lane 3), and transposon mutant #18 (lane 5), the corresponding culture supernatants (lanes 2, 4, and 6), and purified CYT (lane 7); FIG. 18 shows WC preparations of transposon mutant #19 (lane 1), control transposon mutant #20 (i.e., not a BD mutant) (lane 3), serotype 3 strain BC181 (lane 5), the corresponding culture supernatants (lanes 2, 4 and 6), and purified CYT (lane 7); FIG. 19 shows WC preparations of CM5-JB, a naladixic acid resistant variant used to make the transposon (lane 1), transposon mutant #17 (lane 3), and transposon mutant #18 (lane 5), the corresponding culture supernatants (lanes 2, 4, and 6), and purified CYT (lane 7). The transposon insertion in the BD region interferes with the export of the toxin into the culture medium as evidenced in little or no toxin detected in the culture supernatants from the mutants.

Having illustrated and described the principles of the invention in a preferred embodiment, it should be appreciated to those skilled in the art that the invention can be modified in arrangement and detail without departure from such principles. We claim all modifications coming within the scope of the following claims.

TABLE 1

RTX toxins of A. pleuropneumoniae.

| Toxin | Molecular Weight | Synonyms | Activities |
|---|---|---|---|
| ApxI | 105K | HlyI, ClyI | Strongly haemolytic Strongly cytotoxic |
| ApxII | 103K | HlyII, ClyII, App, Cyt | Weakly haemolytic Moderately cytotoxic |
| ApxIII | 120K | Ptx, ClyIII, Mat | Strongly cytotoxic |

TABLE 2

Distribution of the RTX toxin genes of A. pleuropneumoniae in serotypes 1 to 12.

| Genes | Serotype | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| apxICA | + | − | − | − | + | − | − | − | + | + | + | − |
| apxIBD | + | + | − | + | + | + | + | + | + | + | + | + |
| apxIICA | + | + | + | + | + | + | + | + | + | − | + | + |
| apxIIICA | − | + | + | + | − | + | − | + | − | − | − | − |
| apxIIIBD | − | + | + | + | − | + | − | + | − | − | − | − |

TABLE 3

Media

| | | | |
|---|---|---|---|
| 1) | Trypticase Soy Broth | | |
| | pancreatic digest of casein | 17 | g |
| | NaCl | 5.0 | g |
| | papaic digest of soybean meal | 3.0 | g |
| | K$_2$HPO$_4$ | | |
| | glucose | 2.5 | g |
| | dH$_2$O | qs 1 | l |
| | mix and dispense | | |
| | autoclave | | |
| 2) | RPMI | | |
| | NaCl | 6.0 | g |
| | NaHCO$_3$ | 2.0 | g |
| | D-Glucose | 2.0 | g |
| | Na$_2$HPO$_4$.7H$_2$O | 1.5 | g |
| | KCL | 0.4 | g |
| | L-Glutamine | 0.3 | g |
| | L-Arginine | 0.2 | g |
| | Ca(NO$_3$)$_2$.4H$_2$O | 0.1 | g |
| | MgSO$_4$.7H$_2$O | 0.1 | g |
| | L-Asparagine | 0.05 | g |
| | L-Cystine | 0.05 | g |
| | L-Isoleucine | 0.05 | g |
| | L-Leucine | 0.05 | g |
| | L-Lysine-HCl | 0.04 | g |
| | i-Inositol | 0.035 | g |
| | L-Serine | 0.03 | g |
| | L-Aspartic acid | 0.02 | g |
| | L-Glutamic acid | 0.02 | g |
| | L-Hydroxyproline | 0.02 | g |
| | L-Proline | 0.02 | g |
| | L-Threonine | 0.02 | g |
| | L-Tyrosine | 0.02 | g |
| | L-Valine | 0.02 | g |
| | L-Histidine | 0.015 | g |
| | L-Methionine | 0.015 | g |
| | L-Phenylalanine | 0.015 | g |
| | Gycine | 0.01 | g |
| | L-Tryptophan | 5.0 | mg |
| | Phenol Red | 5.0 | mg |
| | Choline Chloride | 3.0 | mg |
| | Glutathione | 1.0 | mg |
| | p-Aminobenzoic acid | 1.0 | mg |
| | Folic acid | 1.0 | mg |
| | Nicotinamide | 1.0 | mg |
| | Pyridoxine.HCl | 1.0 | mg |
| | Thiamine.HCl | 1.0 | mg |
| | D-Calcium pantothenate | 0.25 | mg |
| | Biotin | 0.20 | mg |
| | Riboflavin | 0.20 | mg |
| | Vitamine B$_{12}$ | 5.0 | ug |
| 3) | TYE | | |
| | Reference Niven and O'Reilly - M$^c$Gill | | |
| | Tryptone (Difco) | 20 | g |
| | Yeast extract (Difco) | 5 | g |
| | NaCl (10 mM) | 5.84 | g |
| | KCl (10 mM) | 0.75 | g |
| | Na$_2$HPO$_4$ (10 mM) | 1.42 | g |
| | *(KH$_2$PO$_4$) | 0.46 | g |
| | Glucose (10 mM) | 1.80 | g |
| | dH$_2$O | 950 | ml |
| | to pH 7.4 with KOH (not NaOH) | | |
| | dH$_2$O | QS. 1000 | ml |
| | autoclave | | |
| | add 1 ml of 10% (wt/vol) NAD per liter | | |
| 4) | 5% Sheep Blood Agar with NAD | | |
| | Columbia agar base (Difco) | 44 | g |
| | ddH2O | qs 1 | l |
| | autoclave | | |
| | cool to 45° C. | | |
| | add defibrinated sheep blood | 50 | ml |
| | add 10% NAD | 10 | ml |
| | aseptically pour into petri plates | | |
| 5) | CBA with NAD | | |
| | Columbia agar base (Difco) | 44 | g |
| | ddH2O | qs 1 | l |
| | autoclave | | |
| | cool to 55° C. | | |
| | add defibrinated sheep blood | 50 | ml |
| | heat to 65° C. for 30 min | | |
| | cool to 45° C. | | |
| | add 10% NAD | 10 | ml |
| | aseptically pour into petri plates | | |
| 6) | BLOTTO | | |
| | non-fat dry milk powder (Carnation) | 25 | g |
| | antifoam A | 0.05 | ml |
| | thimerosal | 50 | mg |
| | PBS | QS 500 | ml |
| 7) | TBS | | |
| | Trizma base | 4.84 | g |
| | NaCl | 58.48 | g |
| | dH$_2$O | 1.5 | L |
| | pH to 7.5 with 1M HCl | | |
| | dH$_2$O | QS to 2 | L |
| 8) | TTBS | | |
| | add 0.5 ml Tween-20 to 1 liter TBS | | |
| 9) | Antibody Buffer | | |
| | add 2 g gelatin to 200 ml TTBS | | |
| 10) | Western Blot Transfer Buffer pH 8.3 | | |
| | Trizma base | 3.03 | g |
| | glycine | 14.4 | g |
| | dH$_2$O | 500 | ml |
| | methanol | 200 | ml |
| | dH$_2$O | QS to 1 | L |

TABLE 4

| Cloning Vectors and Plasmids | Properties and Origin | Type and Source of Antibiotic Resistance |
|---|---|---|
| pAKA16 | Mobilizable shuttle vector from 4.3 kb P. Haemolytica plasmid | Ap$^r$ (pHP834) |

TABLE 4-continued

| Cloning Vectors and Plasmids | Properties and Origin | Type and Source of Antibiotic Resistance |
|---|---|---|
| pAKA19 | pIIP843, with MCS and lacZ' Mobilizable suicide vector from pAKA16, with oriV of pBR322 | Ap$^r$ (pHP834) |
| pAKA22 | Mobilizable suicide vector from pAKA16, with oriV of R6K (λ pir dependent) | Ap$^r$ (pHP834) |
| pGZRS-1 | Endogenous 4.3 kb plasmid from *A. pleuropneumoniae* | Sm$^r$ |
| pGZRS-18/19 | Shuttle vector from pGZRS-1, with MCS and lacZ' | Ap$^r$ (Tn3)[1)] |
| pGZRS-38/39 | Shuttle vector from pGZRS-1, with MCS and lacZ' | Km$^r$ (Tn903) |
| pJFF224-NX/XN | Mobilizable broad host range expression shuttle vectors, based on RSF1010 replicon, with MCS and promoter cassette (phage T4 gene 32) | Qn$^r$ p$^{S-a}$ |
| pLOF/Km | Mobilizable transposon delivery plasmid carrying mini-Tn10/Km with inducible transposase (oriV of R6K, λ pir dependent) | Km$^r$ (Tn903) |
| pLS88 | Endogenous *H. ducrei* plasmid, used for various Pasteurellacea as shuttle plasmid | Sm$^r$ Su$^r$ Km$^r$ All are from pLS88 |
| pVE6063 | Thermosenstitive replicon in *E. coli* and in other bacteria, but does not replicate in *A. pleuropneumoniae*. Creates double recombination events. Can be used for targeted insertional mutagenesis. | Dependent upon insert resistance used for creation of knockout mutations |
| pYG53 | (Mobilizable?) Shuttle vector with MCS, based on *A. pleuropneumoniae* plasmid pYG10 | Cm$^r$ (pYG10) |
| pYG54 | Mobilizable shuttle vector from pYG53, containing oriT of RK2 | Cm$^r$ (pYG10) |

Cloning vectors and plasmids for transposon and gene replacement delivery systems for HAP bacteria.
MCS: multiple cloning site
[1)]: with *A. pleuropneumoniae* promoter

TABLE 5

Composition of Bacterin A, Trial 1.

| Component | Volume |
|---|---|
| Strain CM5 heat inactivated 1.2 × 10$^{10}$/ml | 208 ml |
| Strain BC181 heat inactivated 2.15 × 10$^{10}$/ml | 116 ml |
| CM5 supernatant | 63.5 ml |
| L80 adjuvant | 110 ml |
| thimerosal 2% | 2.5 ml |

TABLE 6

Composition of Bacterins B, C, D, and E, Trial 2.

| Component | Experimental Bacterin | | | |
| | B | C | D | E |
|---|---|---|---|---|
| Strain VSB68 TSB (24 h) 1.86 × 10$^{10}$/ml | 32 ml | 108 ml | | |
| Strain VSB68 TYE (6 h) 2.44 × 10$^{10}$/ml | | | 28 ml | 93 ml |
| PBS | 113 ml | 37 ml | 117 ml | 52 ml |
| L80 adjuvant | 54 ml | 54 ml | 54 ml | 54 ml |
| thimerosol 2% | 1 ml | 1 ml | 1 ml | 1 ml |

TABLE 7

Swine sera used in comparative blotting experiments to examine antigen expression and recognition.

| Serum (pig) # | Litter | Treatment Group |
|---|---|---|
| 4 | A | low-dose |
| 9 | A | low-dose |
| 14 | B | low-dose |
| 15 | B | low-dose |
| 3 | A | bacterin |
| 11 | A | bacterin |
| 19 | B | bacterin |
| 20 | B | bacterin |
| 21 | B | bacterin |
| 10 | A | PBS |
| 16 | B | PBS |
| 6 | A | adjuvant |
| 8 | A | adjuvant |
| 18 | B | adjuvant |
| 22 | B | adjuvant | low dose = low dose challenge with strain CM5
bacterin = vaccinated with a commercial bacterin
PBS = mock-vaccinated with PBS
adjuvant = mock-vaccinated with TSB + AlOH placebo vaccine

TABLE 8

Sera of swine exposed to *A. pleuropneumoniae* serotypes 1, 5, and 7.

| Serum # | Serotype | Source |
|---|---|---|
| 1438 | 1 | B. J. Fenwick, Manhattan, Kansas |
| 1458 | 1 | B. J. Fenwick, Manhattan, Kansas |
| 1467 | 1 | B. J. Fenwick, Manhattan, Kansas |
| 5777 | 5 | B. J. Fenwick, Manhattan, Kansas |
| 5781 | 5 | B. J. Fenwick, Manhattan, Kansas |
| 5782 | 5 | B. J. Fenwick, Manhattan, Kansas |
| 5816 | 7 | B. J. Fenwick, Manhattan, Kansas |
| 5818 | 7 | B. J. Fenwick, Manhattan, Kansas |
| 5819 | 7 | B. J. Fenwick, Manhattan, Kansas |

TABLE 9

Sera of CDCD swine exposed to low-dose challenge or vaccinated with a commercial bacterin, PBS, or adjuvant.

| Serum # | Treatment Group |
|---|---|
| A4-3 | low dose |
| A4-3 | low-dose |
| A9-3 | low-dose |
| B14-3 | low-dose |
| B15-3 | bacterin |
| A3-3 | bacterin |
| A11-3 | bacterin |
| B19-3 | bacterin |
| B20-3 | bacterin |
| B21-3 | PBS |
| A10-3 | PBS |
| B16-3 | adjuvant |
| A6-3 | adjuvant |
| A8-3 | adjuvant |
| B8-3 | adjuvant | low dose = low dose challenge with strain CM5
bacterin = vaccinated with a commercial bacterin
PBS = mock-vaccinated with PBS
adjuvant = mock-vaccinated with TSB + AlOH placebo vaccine

TABLE 10

Lung Score System

| Lesion Distribution | Score |
|---|---|
| No visible lesions | 0 |
| Minimal focal lesions | 1 |
| Consolidation/hemorrhage/adhesions: 0–25% of lung | 2 |
| 25–50% of lung | 3 |
| 50–75% of lung | 4 |
| 75–100% of lung | 5 |
| pleural effusion | 1 |
| fibrin adhesions | 1 |
| tracheal froth | 1 |
| pericarditis | 1 |
| Total score | 9 |

Coding of lesions on the affected lung:
1 = haemorrhage
2 = consolidation
3 = nodules
4 = fibrin tags

TABLE 11

Summary of lung scores of Caesarean derived-colostrum deprived pigs at necropsy.

| Pig # | Treatment | Removal Day Post-challenge | Lung Score | Mean Lung Score |
|---|---|---|---|---|
| 126 | adjuvant | D1 | 8 | |
| 110 | adjuvant | D1 | 4 | |
| 116 | adjuvant | D1 | 8 | |
| 104 | adjuvant | D1 | 4 | 6.0 |
| 112 | bacterin | D1 | 5 | |
| 106 | bacterin | D1 | 6 | 5.5 |
| 127 | expt. bacterin A | D22 | 0 | |
| 128 | expt. bacterin A | D3# | 1 | |
| 119 | expt. bacterin A | D22 | 0 | |
| 118 | expt. bacterin A | D3# | 0 | |
| 117 | expt. bacterin A | D22 | 1 | 0.4 |
| 105 | low-dose | D22 | 1 | |
| 113 | low-dose | D22 | 0 | 0.5 |
| 130 | PBS | D10 | 1 | |
| 115 | PBS | D1 | 5 | |
| 135 | PBS | D1 | 5 | |
| 111 | PBS | D1 | 5 | |
| 114 | PBS | D1 | 6 | |
| 129 | PBS | D1 | 2 | 4.0 |

*lung score out of 9
sacrificed early for lung-lavage experiment
PBS = phosphate buffered saline
bacterin = commercial product

TABLE 12

Mean antibody responses ($OD_{405}$) of the CDCD pigs to CYT, LPS, and CPS prior to challenge.

| | CYT | | LPS | | CPS | |
|---|---|---|---|---|---|---|
| Treatment group | PRE | POST | PRE | POST | PRE | POST |
| Bacterin A | 0.045 | 0.264 | 0.002 | 0.190 | 0.001 | 0.017 |
| Commercial Bacterin | 0.040 | 0.069 | 0.0 | 0.007 | 0.0 | 0.000 |
| Low-dose | 0.057 | 0.800 | 0.005 | 0.008 | 0.0 | 0.008 |
| PBS | 0.020 | 0.077 | 0.002 | 0.014 | 0.0 | 0.009 |
| Adjuvant | 0.084 | 0.052 | 0.0 | 0.015 | 0.0 | 0.018 |

PRE = prevaccination bleed
POST = immediately prior to challenge

TABLE 13

Summary of outcome of challenge of SPF pigs with *A. pleuropneumoniae* serotype 1 strain, CM5.

| Pig # | Treatment Group | Weight Gain (Loss) | Lung Score | Mean Lung | Removal Day | Lung/Heat Ratio | Culture Result |
|---|---|---|---|---|---|---|---|
| 36 | adjuvant | ND | 4 | | D1 | 3.0 | + |
| 37 | adjuvant | ND | 9 | | D1 | 4.3 | + |
| 38 | adjuvant | ND | 9 | | D1 | 5.1 | + |
| 39 | adjuvant | ND | 9 | | D1 | 4.6 | + |
| 40 | adjuvant | ND | 9 | 8.0 | D1 | 5.2 | + |
| 101 | bacterin B | ND | 5 | | D1 | 1.3 | + |
| 102 | bacterin B | 0 | 0 | | D5 | 1.6 | − |
| 103 | bacterin B | ND | 5 | | D2 | 3.8 | + |
| 104 | bacterin B | (9) | 2 | | D5 | 1.4 | − |
| 105 | bacterin B | ND | 4 | 3.2 | D3 | 1.2 | + |
| 106 | bacterin C | 2 | 0 | | D5 | 1.5 | − |
| 107 | bacterin C | 0 | 1 | | D5 | 1.4 | − |
| 108 | bacterin C | (2) | 3 | | D5 | 1.4 | + |
| 109 | bacterin C | (1) | 3 | | D5 | 1.3 | + |
| 110 | bacterin C | 0 | 3 | 2.0 | D5 | 1.5 | − |
| 111 | bacterin D | (12) | 4 | | D5 | 1.2 | ND |
| 112 | bacterin D | (13) | 4 | | D5 | 1.2 | + |
| 113 | bacterin D | (2) | 0 | | D5 | 1.5 | − |
| 114 | bacterin D | (1) | 0 | | D5 | 1.5 | + |
| 115 | bacterin D | 6 | 0 | 1.8 | D5 | 1.6 | − |
| 116 | bacterin E | 2 | 2 | | D5 | 1.4 | + |
| 117 | bacterin E | 6 | 0 | | D5 | 1.5 | − |
| 118 | bacterin E | (4) | 4 | | D5 | 1.3 | + |
| 119 | bacterin E | (5) | 4 | | D5 | 1.2 | + |
| 120 | bacterin E | ND | 5 | 3.0 | D1 | 2.2 | + |
| 121 | PBS | ND | 9 | | D1 | 2.9 | + |
| 122 | PBS | ND | 9 | | D2 | 6.2 | + |
| 123 | PBS | ND | 9 | | D1 | 4.7 | + |

TABLE 13-continued

Summary of outcome of challenge of SPF pigs with A. pleuropneumoniae serotype 1 strain, CM5.

| Pig # | Treatment Group | Weight Gain (Loss) | Lung Score | Mean Lung | Removal Day Score | Lung/Heat Ratio | Culture Result |
|---|---|---|---|---|---|---|---|
| 124 | PBS | ND | 6 |     | D1 | 1.7 | + |
| 125 | PBS | ND | 9 | 8.4 | D4 | 1.1 | + |

ND = not done
+ = A. pleuropneumoniae cultured
B = TSB low antigen
C = TSB high antigen
D = TYE low antigen
E = TYE high antigen

TABLE 14

Least-squared mean antibody responses ($OD_{405}$) of the SPF pigs to CYT, LPS and CPS.

| Treatment group | CYT | | LPS | | CPS | |
|---|---|---|---|---|---|---|
|  | Pre | Post | Pre | Post | Pre | Post |
| Bacterin B | 0.116 | 0.371 | 0.003 | 0.814 | 0.005 | 0.788 |
| Bacterin C | 0.154 | 0.321 | 0.007 | 0.559 | 0.008 | 0.617 |
| Bacterin D | 0.109 | 0.567 | 0.006 | 0.962 | 0.003 | 0.956 |
| Bacterin E | 0.126 | 0.445 | 0.007 | 0.744 | 0.006 | 0.818 |
| PBS | 0.083 | 0.057 | 0.003 | -0.003 | 0.004 | -0.001 |
| Adjuvant | 0.129 | 0.145 | 0.001 | 0.003 | 0.002 | 0.001 |

Bacterin B = TSB-grown, low antigen concentration
Bacterin C = TSB-grown, high antigen concentration
Bacterin D = TYE-grown, low antigen concentration
Bacterin E = TYE-grown, high antigen concentration
Pre = prevaccination bleed
Post = immediately prior to challenge

REFERENCES

Anderson, C., A. A. Potter, G. F. Gerlach. 1991. Isolation and molecular characterization of spontaneously occuring cytolysin-negative mutants of *Actinobacillus pleuraopneumoniae* serotype 7. Infect. Immun. 59:4110–4116.

Belanger, M., D. Dubreuil, J. Harel, C. Girard, M. Jaques. 1990. Role of lipopolysaccharides in adherence of *Actinobacillus pleuropneumoniae* to porcine tracheal rings. Infect. Immun. 58:3523–3530.

Bendixen, P. A., P. Shewen, S. Rosendal, B. N. Wilkie. 1981. Toxicity of *Haemophilus pleuropneumoniae* for porcine lung macrophages, peripheral blood monocytes, and testicular cells. Infect. Immun. 33:673–676.

Bertram, T. A. 1988. Pathobiology of acute pulmonary lesions in swine infected with *Haemophilus* (*Actinobacillus*) *pleuropneumoniae*. Can. Vet. J. 29:574–577.

Bertschinger, H. U. and P. Seifert. 1978. Isolation of a Pasteurella Haemolytica-like organism from porcine necrotic pleuropneumonia. Proc. 5th Int. Congr. Pig Vet. Soc. Zagreb, Yugoslavia, Abstr. M19.

Betsou, F., P. Sebo and N. Guisu. 1993. CyaC-Mediated Activation Is Important Not Only For Toxic but Also For Protective Activities Of *Bordetella pertussis* Adenylate Cyclase-Hemolysin. Infection and Immunity. Vol.61:3583–3589.

Bossé, J. T., R. P. Johnson, S. Rosendal. 1990. Capsular polysaccharide antigens for the detection of serotype-specific antibodies to *Actinobacillus pleuropneumoniae*. Can. J. Vet. Res. 54:320–325.

Bossé, J. T., R. P. Johnson, M. Nemec, S. Rosendal. 1992. Protective local and systemic antibody responses of swine to an aerosol of *Actinobacillus pleuropneumoniae* serotype 1. Infect. Immun. 60–479–484.

Borr, J. D., D. A. J. Ryan and J. I. MacInnes. 1991. Analysis of *Actinobacillus pleuropneumoniae* and related organisms by DNA-Dna hybridization and restriction endonuclease fingerprinting. Int. J. Syst. Bacteriol. 41:121–129.

Bourne F. J. 1969. IgA immunoglobulin from porcine serum. Biophys. Res. Commun. 36:138–145.

Bradley, P. A., F. J. Bourne, P. J. Brown. 1976. The respiratory tract immune system in the pig. I. The distribution of immunoglobulin containing cells in the respiratory tract mucosa. Vet. Path. 13:81–89.

Braun, V., T. Focareta. 1991. Pore-forming bacterial protein haemolysins (cytolysins). Critic. Rev. Microbiol. 18:115–158.

Charley, B., G. Corthier. 1977. Local immunity in the pig respiratory tract. II. relationship of serum and local antibodies. Ann. Microbiol. 128:109–119.

Chang Y., R. Y. Young, D. K. Struck. 1991. The *Actinobacillus pleuropneumoniae* hemolysin determinant: unlinked appCA and appBD loci flanked by pseudogenes. J. Bacteriol. 173:5151–5158.

Chang, Y., R. Y. Young, D. K. Struck. 1989. Cloning and characterization of a haemolysin gene from *Actinobacillus* (*Haemophilus*) *pleuropneumoniae*. DNA 8:635–647.

Chang-Jo Lian, S. Rosendal, J. I. MacInnes. 1989. Molecular cloning and characterization of a haemolysin gene from *Actinobacillus* (*Haemophilus*) *pleuropneumoniae* Infect. Immun.57:3377–3382.

Chiang, W., T. F. Young, V. J. Rapp-Gabrielson, R. F. Ross. 1991. Improved protection of swine from pleuropneumonia by vaccination with proteinase K-treated outer membrane of *Actinobacillus* (*Haemophilus*) *pleuropneumoniae*. Vet. Microbiol. 27:49–62.

Conlon, J. A., P. E. Shewen, R. Y. C. Lo. 1991. Efficacy of a recombinant leukotoxin in protection against pneumonic challenge with live *Pasteurella haemolytica* A1. Infect. Immun. 59:587–591.

Corbeil, L. B., S. A. Kania, R. P. Gogolewski. 1991. Characterization of the immunodominant surface antigens of *Haemophilus somnus*. Infect. Immun. 59:4295–4301.

Corbeil, L. B., J. E. Arthur, P. R. Widders, J. W. Smith, A. F. Barbet. 1987. Antigenic specificity of convalescent serum from cattle with *Haemophilus somnus* induced experimental abortion. Infect. Immun. 55:1381–1386.

Curtis J., F. J. Bourne. 1971. Immunoglobulin quantification in sow serum, colostrum and milk and the serum of young pigs. Biochim. Biophys. Acta. 236:319–332.

Deneer, H. G., A. A. Potter. 1989. Effect of iron restriction on the outer membrane proteins of *Actinobacillus* (*Haemophilus*) *pleuropneumoniae*. Infect. Immun. 57:798–804.

Devenish, J., S. Rosendal, J. T. Bossé. 1990. Humoral antibody response and protective immunity in swine following immunization with the 104-kilodalton haemolysin of *Actinobacillus pleuropneumoniae*. Infect. Immun. 58:3829–3832.

Devenish, J., S. Rosendal. 1989. Identification of the heat-labile haemolysin of *Actinobacillus pleuropneumoniae* serotype 1. Can. J. Vet. Res. 53:251–254.

Devenish, J., S. Rosendal, R. Johnson, S. Hubler. 1989. Immunoserological comparison of 104-kilodalton proteins associated with hemolysis and cytolysis in *Actinobacillus pleuropneumoniae, Actinobacillus suis, Pasteurella haemolytica,* and *Eschereschia coli.* Infect. Immun. 57:3210–3213.

Fedorka-Cray, P. J., 1989. *Actinobacillus (Haemophilous) pleuropneumoniae* virulence factors: Partial characterization and efficacy studies in swine. University of Nebraska, Ph.D. Thesis.

Fedorka-Cray, P. J., M. J. Heuther, D. L. Stine, G. A. Anderson. 1990. Efficacy of a cell extract from *Actinobacillus (Haemophilus) pleuropneumoniae* serotype 1 against disease in swine. Infect. Immun. 58:358–365.

Fenwick, B. W., J. S. Cullor, B. I. Osburn, H. J. Olander. 1986. Mechanisms involved in protection provided by immunization against core lipopolysaccharides of *Escherichia coli* J5 from lethal *Haemophilus pleuropneumoniae* infections in swine. Infect. Immun. 53:298–304.

Fenwick, B. J., B. I. Osburn. 1986. Vaccine potential of *Haemophilus pleuropneumoniae* oligosaccharide-tetanus toxoid conjugates. Infect. Immun. 54:583–586.

Fenwick, B. W., B. I. Osburn, H. J. Olander. 1986. Isolation and biochemical characterization of two lipopolysaccharides and a capsular-enriched polysaccharide preparation from *Haemophilus pleuropneumoniae.* Am. J. Vet. Res. 47:1433–1441.

Fenwick, B. W., B. I. Osburn. 1986. Immune responses to the lipopolysaccharides and capsular polysaccharides of *Haemophilus pleuropneumoniae* in convalescent and immunized pigs. Infect. Immun. 54:575–582.

Frey, J., J. Nicolet. 1988. Purification and partial characterization of a haemolysin produced by *Actinobacillus pleuropneumoniae* type strain 4074. FEMS Microbiol. Lett. 55:41–46.

Frey, J., J. Nicolet. 1988. Regulation of hemolysin expression in *Actinobacillus pleuropneumoniae* serotype 1 by $Ca^{2+}$. Infect. Immun. 56:2570–2575.

Frey J., J. Perrin, J. Nicolet. 1989. Cloning and expresion of a cohemolysin, the CAMP factor of *Actinobacillus pleuropneumoniae.* Infect. Immun. 57:2050–2056.

Frey, J., J. Nicolet. 1990. Haemolysin patterns of *Actinobacillus pleuropneumoniae.* J. Clin. Microbiol. 28:232–236.

Frey, J., J. T. Bossé, Y. F. Chang, J. M. Cullen, B. Fenwick, G. F. Gerlach, D. Gygi, F. Haesebrouck, T. J. Inzana, R. Jansen, E. M. Kamp, J. Macdonald, J. I. MacInnes, K. R. Mittal, J. Nicolet, A. N. Rycroft, R. P. A. M. Segers, M. A. Smits, E. Stenbaek, D. K. Struck, J. F. van den Bosch, P. J. Willson. 1993. *Actinobacillus pleuropneumoniae* RTX toxins: uniform designation of haemolysins, cytolysins, pleurotoxin and their genes. J. Gen. Microbiol. 139:1723–1728.

Frey, J. T., M. Beck, J. van den Bosch, R. P. A. M. Segers, J. Nicolet. 1995. Development of an efficient PCR method for toxin typing of *Actinobacillus pleuropneumoniae* strains. Mol. Cell. Probes. 9:xxx-xxx.

Frey, J. T., R. Kuhn, J. Nicolet. 1994. Association of the CAMP phenomenon in *Actinobacillus pleuropneumoniae* with the RTX toxins ApxI, ApxII and ApxIII. FEMS Microbiol. Let. 124:245–252.

Gentry, M. J., A. W. Confer, R. J. Panciera. 1985. Serum neutralization of cytotoxin from *Pasteurella haemolytica* serotype 1 and resistance of experimental bovine pneumonic pasteurellosis. Vet. Immunol. Immunopath. 9:239–250.

Gerlach, G. F, C. Anderson, A. A. Potter, S. Klashinsky, P. J. Willson. 1992. Cloning and expression of a transferring-binding protein from *Actinobacillus pleuropneumoniae.* Infect. Immun. 60:892–898.

Glisson, J. R., I. H. N. Chen. 1991. In vivo antigen expression by *Pasteurella multocida.* Avian Dis. 35:392–396.

Gogolewski, R. P., L. B. Corbeil. 1987. Protective ability and specificity of convalescent serum from calves with *Haemophilus somnus* pneumonia. Infect. Immun. 55:1403–1411.

Gonzalez, G. C., D. L. Caamano, A. B. Shryvers. 1990. Identification and characterization of a porcine-specific transferring receptor in *Actinobacillus pleuropneumoniae.* Mol. Microbiol. 4:1173–1179.

Goyette, G., S. Lariviere, K. R. Mittal, R. Higgins, G. P. Martineau. 1986. Comparison of CFT, ELISA, and tube agglutination test with 2-ME in pigs with or without *Haemophilus pleuropneumoniae* infection. Proc. Int. Pig Vet. Soc. Cong. 9:258.

Groom, S. C., P. B. Little. 1988. Effects of vaccination of calves against induced *Haemophilus somnus* pneumonia. Am. J. Vet. Res. 49:793–800.

Gunnarsson A., E. L. Biberstein, B. Hurvell. 1977. Serologic studies on porcine strains of *Haemophilus parahaemolyticus (pleuropneumoniae)*: agglutination reactions. J. Amer. Vet. Res. 38:1111–1114.

Gygi, D., J. Nicolet, J. Frey, M. Cross, V. Koronakis, C. Hughes. 1990. Isolation of the *Actinobacillus pleuropneumoniae* haemolysin gene and the activation and secretion of the prohaemolysin by the HlyC, HlyB and HlyD proteins of *Escherichia coli.* Mol. Microbiol. 4:123–128

Hancock, R. E. W. 1991. Bacterial outer membranes: evolving concepts. ASM News. 57:175–182.

Helwig, T. T. and K. A. Council. 1982. SAS users guide. SAS Institute. Raleigh, N.C.

Heuther, M. J., P. J. Fedorka-Cray, M. A. Pfannensteil, G. Anderson. 1987. Plasmid profiles and antibiotic susceptibility of *Haemophilus pleuropneumoniae* serotypes 1, 3, 5, and 7. FEMS Microbiol. Let. 48:179–182.

Holmgren, N. 1973. Immunoglobulins in normal porcine tracheobronchial secretions. Acta. Vet. Scand. 14:366–380.

Inzana, T. J., J. Ma, T. Workman, R. P. Gogolewski, P. Anderson. 1988. Virulence properties and protective efficacy of the capsular polymer of *Haemophilus (Actinobacillus) pleuropneumoniae* serotype 5. Infect. Immun. 56:1880–1889.

Inzana, T. J., 1987. Purification and partial characterization of the capsular polymer of *Haemophilus pleuropneumoniae* serotype 5. Infect. Immun. 55:1573–1579.

Inzana, T. J., J. Todd, J. MA, H. Veit. 1991. Characterization of a non-haemolytic mutant of *Actinobacillus pleuropneumoniae* serotype 5. Micro. Path. 10:281–296.

Inzana, T. J., 1991. Virulence properties of *Actinobacillus pleuropneumoniae.* Microb. Path. 11:305–316.

Inzana, T. J., B. Mathison. 1987. Serotype specificity and immunogenicity of the capsular polymer of *Haemophilus pleuropneumoniae* serotype 5. Infect. Immun. 55:1580–1587.

Jansen, R., J. Briare, E. M. Kamp, M. A. Smits. 1992. Comparison of the cytolysin II genetic determinants of *Actinobacillus pleuropneumoniae* serotypes. Infect. Immun. 60:630–636.

Jansen, R. 1994. The RTX toxins of *Actinobacillus pleuropneumoniae,* PhD. thesis. DLO-Central Veterinary Institute, Lelystad, The Netherlands.

Jansen, R. et al, 1995. Infect. Immun.

Jensen, A. E., T. A. Bertram. 1986. Morphological and biochemical comparison of virulent and avirulent isolates of *Haemophilus pleuropneumoniae* serotype 5. Infect. Immun. 51:419–424.

Jonsson, A., 1973. Transfer of immunoglobulins from mother to offspring in the pig. Acta. Vet. Scand. suppl. 43:1–64.

Kaltreider H. B., J. S. Johnson. 1972. Porcine immunoglobulins. I. Identification of classes and preparation of specific antisera. J. Immunol. 109:992–998.

Kamp, E. M., J. K. Popma, J. Anakota, M. Smits. 1991. Identification of haemolytic and cytotoxic proteins of *Actinobacillus pleuropneumoniae* by use of monoclonal antibodies. Infect. Immun. 59:3079–3085.

Kamp, E. M et al., 1987. Veterinary Microbiology 13:249–257

Killian, M. 1976. The haemolytic activity of Haemophilus species. Acta. Path. Microbiol. Scand. Sect. B. 84:339–341.

Koronakis, V., M. Cross, B. Senior, E. Koronakis, C. Hughes. 1987. The secreted haemolysins of *Proteus mirabilis, Proteus vulgaris*, and *Morganella morganii* are genetically related to each other and to the alpha-haemolysin of *Escherichia coli*. J. Bacteriol. 169:1509–1515.

Korvuo, A., L. Lindberg, J. Tuomi, J. Schroder. 1988. Use of monoclonal antibodies to serotype-specific antigens of *Haemophilus pleuropneumoniae* serotype 2 in passive immunization. Am. J. Vet. Res. 49:2072–2075.

Kume, K., T. Nakai. 1986. Species specificity of *Haemophilus pleuropneumoniae* hemolysin demonstrated in the cytocidal and anti-phagocytic effects. Jpn. J. Vet. Sci. 48:993–997.

Kume, K., T. Nakai, A. Sawata. 1986. Interaction between heat-stabile hemolytic substance from *Haemophilus pleuropneumoniae* and porcine pulmonary macrophages in vitro. Infect. Immun. 51:563–570.

Lallier, R., L. Le Blanc, F. Morrissette, R. Higgins. 1987. Detection of a permeability factor produced by *Haemophilus pleuropneumoniae*. Current Microbiol. 15:141–144.

Lombin, L., S. Rosendal and W. R. Mitchell. 1981. Evaluation of the complement fixation test for diagnosis of pleuropneumonia of swine caused by *Haemophilus pleuropneumoniae* Can. J, Comp. Med. 46:109–114.

Ma, J., T. J. Inzana, 1990. Indirect enzyme-linked immnunosorbent assay for the detection of antibody to a 110,000 molecular-weight haemolysin of *Actinobacillus pleuropneumoniae*. J. Clin. Microbiol. 28:1356–1361.

MacInnes, J. I., J. E. Kim, C. J. Lian, G. A. Soltes. 1990. *Actinobacillus pleuropneumoniae* hlyX gene homology with the fnr gene of *Escherichia coli*. J. Bacteriol. 172:4587–4592.

MacInnes, J. I., S. Rosendal. 1987. Analysis of major antigens of *Haemophilus* (*Actinobacillus*) *pleuropneumoniae* and related organisms. Infect. Immun. 55:1626–1634.

MacInnes, J. I., J. D. Borr, M. Massoudi, S. Rosendal. 1990. Analysis of Southern Ontario *Actinobacillus* (*Haemophilus*) *pleuropneumoniae* isolates by restriction endonuclease fingerprinting. Can. J. Vet. Res. 54:244–250.

Martin, S. W., K. G. Bateman, P. E. Shewen, S. Rosendal, J. G. Bohac. 1989. The frequency, distribution and effects of antibodies to seven putative respiratory pathogens on respiratory disease and weight gain in feedlot calves in Ontario. Can. J. Vet. Res. 51:83–88.

Martin, P. G., P. Lachance, D. F. Niven. 1985. Production of an RNA-dependent haemolysin by *Haemophilus pleuropneumoniae*. Can. J. Microbiol. 31:456–462.

Martin, P. et al.,1989. Can. J. Vet. Res. 51:83–88.

Maudsley, J. R., S. Kadis, W. R. Mayberry, 1986. Isolation, purification, and partial characterization of a lipopolysaccharide from *Haemophilus pleuropneumoniae*. Infect. Immun. 51:501–506

Maudsley, J. R., S. Kadis. 1986. Growth and hemolysin production by *Haemophilus pleuropneumoniae* cultivated in a chemically defined medium. Can. J. Microbiol. 32:801–805.

Mittal, K. R., S. Bourdon. 1991. Cross-reactivity and antigenic heterogeneity among *Actinobacillus pleuropneumoniae* strains of serotypes 4 and 7. J. Clin. Microbiol. 29:1344–1347.

Mittal, K. R., R. Higgins, S. Lariviere. 1982. Evaluation of slide agglutination and ring precipitation tests for capsular serotyping of *Haemophilus pleuropneumoniae*. J. Clin. Microbiol. 15:1019–1023.

Mittal, K. R., R. Higgins, S. Lariviere. 1983a Identification and serotyping of *Haemophilus pleuropneumoniae* by coagglutination test. J. Clin. Microbiol. 18:1351–1354.

Morgan K. L., A. M. Hussein, T. J. Newby, F. J. Bourne. 1980. Quantification and origin of the immunoglobulins in porcine respiratory tract secretions. Immunology. 41:729–736.

Mosier, D. A., K. R. Simmons, A. W. Confer, R. J. Panciera, K. D. Klinkenbeard. 1989. *Pasteurella haemolytica* antigens associated with resistance to pneumonic pasteurellosis. Infect. Immun. 57:711–716.

Nakai, T., A. Sawata, K. Kume. 1983. Characterization of the hemolysin produced by *Haemophilus pleuropneumoniae*. Am. J. Vet. Res. 44:344–347.

Neilson, R. 1984. *Haemophilus pleuropneumoniae* serotypes—cross protection experiments. Nord. Vet. Med. 36:221–234.

Neilson, R. 1986. Serological characterization of *Actinobacillus pleuropneumoniae* strains and proposal of a new serotype: serotype 12. Acta Vet. Scand. 27:453–455.

Nicolet, J. 1992. *Actinobacillus pleuropneumoniae*, In Diseases of swine. 7th Ed. Ed. A. D. Lehman, B. E. Straw, W. L. Mengeling, S. D'Allaire, and D. J. Taylor, pp 401–408. Ames: Iowa State University Press.

Nicolet, J., P. A. deMeuron, P. H. Bachman. 1971. IV. L'epreuve de fixation de complement, un test de depistage des infections a *Haemophilus parahaemolyticus*. Schweiz. Arch. Tierheilkd. 113:191–200.

Niven, D. F., M. Levesque, 1988. V-factor-dependent growth of *Actinobacillus pleuropneumoniae* biotype 2 (Bertschinger 2008/76). Int. J. Sys. Bacteriol. 38:319–320.

O'Reilly, T., D. F. Niven, M. R. W. Brown. 1991. Phenotypic variation in the outer membrane protein composition of *Actinobacillus* (*Haemophilus*) *pleuropneumoniae*: nonspecific effect of exogenous pyridine nucleotide supply. Vet. Microbiol. 29:159–172.

O'Reilly, T., D. F. Niven. 1986. Tryptone yeast extract broth as a culture medium for *Haemophilus pleuropneumonia* and *Haemophilus parasuis* to be used as challenge inocula. Can. J. Vet. Res. 50:441–443.

Pattison, I. H. D. G. Howell, J. Elliot. 1957. A Haemophilous-like organism isolated from pig lung and the associated pneumonic lesions. J. Comp. Pathol. 67:320–329.

Perry, M. B., E. Altman, J. R. Brisson, L. M. Beynon, J. C. Richards. 1990. Structural characteristics of the antigenic capsular polysaccharides and lipopolysaccharides involved in the serological classification of *Actinobacillus*

(*Haemophilus*) *pleuropneumoniae* strains. Serodiag. Immunother. Inf. Dis.4:299–308.

Piffer, I. A., G. R. Carter, A. A. F. Botovchenco. 1986. Identification of serotypes of *Haemophilus pleuropneumoniae* by counter immunoelectrophoresis. Vet. Rec. 118:292–294.

Pijoan, C. 1986. Effect of *Pasteurella multocida* and *Haemophilus pleuropneumoniae* toxins on swine alveolar macrophages. Vet. Immun. Immunopath. 13:141–149.

Pohl, S., H. U. Bertschinger, W. Frederiksen, W. Mannaheim. 1983. Transfer of *Haemophilus pleuropneumoniae* and the *Pasteurella haemolytica*-like organism causing porcine necrotic pleuropneumonia to the genus Actinobacillus (*Actinobacillus pleuropneumoniae* comb. nov.) on the basis of phenotypic and deoxyribonucleic acid relatedness. Int. J. System. Bacteriol. 33:510–514.

Rapp, V., R. F. Ross. 1986. Antibody response of swine to outer membrane components of *Haemophilus pleuropneumoniae* during infection. Infect. Imunun. 54:751–760.

Rapp. V., R. F. Ross. 1988. Immunogenicity of outer membrane components of *Haemophilus* (*Actinobacillus*) *pleuropneumoniae*. Can. Vet. J. 29:585–587.

Rodriguez R. L., and R. C. Tait. 1983. Recombinant DNA techniques: an introduction, p 197–199. Addison-Wesley Publishing Co., Don Mills, Ontario.

Rosendal, S. and D. Boyd. 1982. Serotyping of *Haemophilus pleuropneumoniae*. J. Clin. Micrbiol. 16:840–843.

Rosendal, S., D. S. Carpenter, W. R. Mitchell and M. R. Wilson. 1981. Vaccination against pleuropneumonia of pigs caused by *Haemophilus pleuropnumoniae*. Can Vet. J. 22:34–35.

Rosendal, S., J. I. MacInnes. 1990. Characterization of an attenuated strain of *Actinobacillus pleuropneumoniae* serotype 1. Am. J. Vet. Res. 51:711–717.

Rosendal, S., O. P. Miniats and P. Sinclair. 1986. Protective efficacy of capsule extracts of *Haemophilus pleuropneumoniae* in pigs and mice. Vet. Microbiol., 12:229–240.

Rosendal, S. and W. R. Mitchell. 1983. Epidemiology of *Haemophilus pleuropneumoniae* infection in pigs. A survey of Ontario pork producers, 1981. Can. J. Comp. Med. 47:1–5.

Rycroft, A. N., D. J. Taylor. 1987. Preparation and characterization of envelope proteins from *Haemophilus pleuropneumoniae*. Vet. Microbiol. 15:303–314.

Rycroft, A. N., D. Williams, J. M. Cullen, J. Macdonald. 1991. The cytotoxin of *Actinobacillus pleuropneumoniae* (pleurotoxin) is distinct from the haemolysin and is associated with a 120 kDa polypeptide. J. Gen. Microbiol. 137:561–568.

Sebunya, T. N. K., J. R. Saunders. 1983. *Haemophilus pleuropneumoniae* infection in swine. J. Am. Vet. Med. Assoc. 182:1331–1337.

Setcavage T. M., Y. B. Kim. 1976. Characterization of porcine immunoglobulins IgG, IgM, and IgA and the preparation of monospecific antichain sera. Immunochem. 13:643–652.

Shewen, P. E., A. Sharpe, B. N. Wilkie. 1988. Efficacy testing a *Pasteurella haemolytica* extract vaccine. Vet. Med. 10:1078–1083.

Shewen, P. E., B. N. Wilkie. 1987. Vaccination of calves with leukotoxic culture supernatant from *Pasteurella haemolytica*. Can. J. Vet. Res. 52:30–36.

Shope, R. E. 1964. Porcine contagious pleuropneumonia. I. Experimental transmission, etiology, and pathology. J. Exp. Med. 119:357–368.

Silva, P., P. B. Little. 1991. The protective effect of vaccination against experimental pneumonia in cattle with *Haemophilus somnus* outer membrane antigens and interference by lipopolysaccharide. Can. J. Vet. Res. 54:326–330.

Sirois, M., E. G. Lemire, R. C. Levesque. 1991. Construction of a DNA probe and detection of *Actinobacillus pleuropneumoniae* by using polymerase chain reaction. J. Clin. Microbiol. 29:1183–1187.

Smits, M. A., J. Briare, R. Jansen, H. E. Smith, E. M. Kamp, A. L. J. Gielkens. 1991. Cytolysins of *Actinobacillus pleuropneumoniae* serotype 9. Infect. Immun. 59:4497–450

Stine, D. L., M. J. Heuther, R. A. Moxley, S. Srikumaran. 1991. *Actinobacillus pleuropneumoniae*-induced thymic lesions in mice and pigs. Infect. Innmun. 59:2885–2891.

Strathdee, C. A., R. Y. C. Lo. 1989. Regulation of the expression of the *Pasteurella haemolytica* leukotoxin determinant. J. Bacteriol. 171:5955–5962.

Strathdee, C. A., R. Y. C. Lo. 1989. Cloning, nucleotide sequence, and characterization of genes encoding the secretion function of the *Pasteurella haemolytica* leukotoxin determinant. J. Bacteriol. 171:916–928.

Thwaits, R., S. Kadis. 1991. Immunogenicity of *Actinobacillus pleuropneumoniae* outer membrane proteins and enhancement of phagocytosis by antibodies to the proteins. Infect. Immun. 59:544–549.

Thompson S. A., L. W. Wang, A. West and P. F. Sparling. 1993. *Neisseria meningitidis* Produces Iron-Regulated Proteins Related to the RTX Family of Exoproteins. J. Bacteriol. 175:811–818.

Trottier, Y., P. W. Wright, S. Lariviere. 1992. Optimization and standardization of an enzyme-linked immunosorbent assay protocol for serodiagnosis of *Actinobacillus pleuropneumoniae* serotype 5. J. Clin. Microbiol. 30:46–53.

Van den Bosch, J. F., I. M. C. A. Jongenelen, A. N. B. Puben, F. G. A. van Vugt, R. P. A. M. Segers. 1992. Protection induced by a trivalent *Actinobacilius pleuropneumoniae* subunit vaccine. abst. 194. Proceedings of the 12th International Pig Veterinary Society. The Hague. The Netherlands.

van Leengoed, L. A. M., H. W. Dickerson. 1992. Influence of calcium on secretion and activity of the cytolysins of *Actinobacillus pleuropneumoniae*. Infect. Immun. 60:353–359.

Welch, R. A. 1991. Pore-forming cytolysins of gram-negative bacteria. Molec. Microbiol. 5:521–528.

Welch, R. A., S. Pellett. 1988. Transcriptional organization of the *Eschericia coli* hemolysin genes. J. Bacteriol. 170:1622–1630.

West, S. E. H., M. -J. M. Romero, L. B. Regassa, N. A. Zielinski, and R. A. Welch; 1995. Construction of an *Actinobacillus pleuropneumoniae-Escherichia coli* shuttle vectors: expression of antibiotic resistance genes. Gene (in press)

Willson, P. J., C. Shipper, E. D. Morgan. 1988. The use of an enzyme-linked immunosorbent assay for diagnosis of *Actinobacillus pleuropneumoniae* infection in pigs. Can Vet. J. 29:583–585.

ABBREVIATIONS $A_{405}$—absorbance at 405 nm
AlOH—aluminum hydroxide
BEI—binary-ethyleneimine
BPL—β-propiolactone
CBA—chocolate blood agar CBA-NAD—chocolate blood agar with 0.1% (wt/vol) NAD
CDCD—caesarean derived, colostrum deprived
CPS—capsular polysaccharide
CYT—cytolysin
°C—degrees Celsius
ddH$_2$O—double distilled water
FCS—fetal calf serum
g—grams
xg—times gravity
h—hours
IM—intramuscularly
LPS—lipopolysaccharide
M—molar
mg—milligram
min—minutes
ml—milliliter
mM—millimolar
NaCl—sodium chloride
NAD—nicotinamide adenine dinucleotide
ng—nanogram
OD—optical density
OMP—outer-membrane protein
PAGE—polyacrylamide gel electrophoresis
PBS—phosphate buffered saline
qs—quantum sufficit
rpm—revolutions per minute
SDS—sodium dodecyl sulfate
SPF—specific pathogen free
Tris—tris(hydroxymethyl)aminomethane
TBS—Tris buffered saline
TSB-NAD—trypficase soy broth with 0.01% (wt/vol) NAD
TTBS—Tween 20-Tris buffered saline
TYE-NAD—tryptone-yeast extract with 0.01% (wt/vol) NAD
μg—microgram
μl—microliter
V—volts
vol—volume
WC—whole cell
wt—weight

We claim:

1. A bacterial preparation comprising one or more isolated and purified strain(s) of a microorganism which produces one or more RTX toxins, wherein the strain is cultured in tryptone yeast extract (TYE) broth which strain(s) has at least one RTX toxin which is substantially cell-associated.

2. The bacterial preparation as claimed in claim 1, wherein said microorganism is a pathogenic gram negative bacteria.

3. The bacterial preparation as claimed in claim 2, wherein said microorganism is selected from the family group consisting of Pasteurellaceae and Enterobacteriaceae.

4. The bacterial preparation as claimed in claim 3, wherein said microorganism is selected from the group consisting of *A. Pleuropneumoniae, A. actinomycetemcomitans, A. suis, A. equuli, Pasteurella haemolytica, Escherichia coli, Proteus vulgaris, Proteus mirabilis, Morganella morganii,* and *Bordetella pertussis.*

5. A bacterial preparation comprising one or more isolated and purified strain(s) of *A. pleuropneumoniae* wherein said strains are produced by targeted mutagenesis of the D and B transport genes using a method selected from the group consisting of allelic replacement, insertional inactivation, and deletion formation, which strain has substantially cell-associated, one or more RTX toxins selected from the group consisting of ApxI, ApxII, ApxIII.

6. A bacterial preparation comprising two or more isolated and purified strains of *A. pleuropneumoniae* which collectively have ApxI, ApxII and ApxIII which are substantially cell-associated.

7. A method for preparing a bacterial preparation as claimed in claim 1 comprising selecting one or more strains of a microorganism which produces one or more RTX toxins, and culturing the selected strains in a tryptone yeast extract (TYE) medium under suitable conditions so that the RTX toxin is substantially cell-associated.

8. A method as claimed in claim 7 wherein said selected strain is cultured and maintained in log phase.

9. A method for preparing a bacterial preparation as claimed in claim 1 comprising selecting one or more strain of a microorganism which produces one or more RTX toxins, and treating the strain with a substance which interferes with the secretion of the RTX toxins, and isolating and purifying the selected one or more strains.

10. A method as claimed in claim 9 wherein said substance is a nucleic acid sequence encoding the D and B transport genes inverted relative to their normal orientation for transcription.

11. A method for preparing a bacterial preparation as claimed in claim 1 comprising producing the strain using gene transfer techniques and isolating and purifying the strain.

12. A method as claimed in claim 10, wherein said strain is produced by targeted mutagenesis of the D and B transport genes using a method selected from the group consisting of allelic replacement, insertional inactivation, and deletion formation.

13. A method as claimed in claim 11, wherein said strain is produced by transposon mutagenesis.

14. A method as claimed in claim 12, wherein said strain is a transposon mutant of *A. pleuropneumoniae.*

15. A method as claimed in claim 10, wherein said strain is produced by targeted mutagenesis of the D transport gene using a method selected from the group consisting of allelic replacement, insertional inactivation and deletion formation.

16. A method as claimed in claim 10, wherein said strain is produced by targeted mutagenesis of the B transport gene using a method selected from the group consisting of allelic replacement, insertional inactivation and deletion formation.

17. A method as claimed in claim 9, wherein said substance is a nucleic acid sequence encoding the D transport gene inverted relative to its normal orientation for transcription.

18. A method as claimed in claim 9, wherein said substance is a nucleic acid sequence encoding the B transport gene inverted relative to its normal orientation for transcription.

19. A method as claimed in claim 19, wherein said strain is a transposan mutant of *A. pleuropneumoniae.*

20. A method as claimed in claim 20, wherein said strain is a transposan mutant of *A. pleuropneumoniae.*

21. A bacterial preparation as claimed in claim 2, wherein said microorganism expresses one or more RTX toxins.

22. A bacterial preparation comprising one or more isolated purified strains of microorganisms which produces one or more RTX toxins, wherein said strains are produced by targeted mutagenesis of the D and B transport genes using a method seletected from the group consisting of allelic replacement, insertional inactivation, and deletion formation.

23. A bacterial preparation comprising one or more isolated purified strains of microorganisms which produces one or more RTX toxins, wherein said strains are cultured in TYE medium and is produced by targeted mutagenesis of the D and B transport genes using a method seletected from the group consisting of allelic replacement, insertional inactivation, and deletion formation.

* * * * *

```
                        SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 172 amino acids
        (B) TYPE: amino acid
        (C) STRANDEDNESS: single
        (D) TOPOLOGY: circular (ii) MOLECULE TYPE: protein (vi) ORIGINAL SOURCE:
         (A) ORGANISM: Actinobacillus pleuropneumoniae (xi) SEQUENCE DESCRIPTION: SEQ ID NO:1:

Met Ser Lys Lys Ile Asn Gly Phe Glu Val Leu Gly Glu Val Ala Trp
1               5                   10                  15

Leu Trp Ala Ser Ser Pro Leu His Arg Lys Trp Pro Leu Ser Leu Leu
                20                  25                  30

Ala Ile Asn Val Leu Pro Ala Ile Glu Ser Asn Gln Tyr Val Leu Leu
            35                  40                  45

Lys Arg Asp Gly Phe Pro Ile Ala Phe Cys Ser Trp Ala Asn Leu Asn
50                  55                  60

Leu Glu Asn Glu Ile Lys Tyr Leu Asp Asp Val Ala Ser Leu Val Ala
65                  70                  75                  80

Asp Asp Trp Thr Ser Gly Asp Arg Arg Trp Phe Ile Asp Trp Ile Ala
                85                  90                  95

Pro Phe Gly Asp Ser Ala Ala Leu Tyr Lys His Met Arg Asp Asn Phe
            100                 105                 110

Pro Asn Glu Leu Phe Arg Ala Ile Arg Val Asp Pro Asp Ser Arg Val
        115                 120                 125

Gly Lys Ile Ser Glu Phe His Gly Gly Lys Ile Asp Lys Lys Leu Ala
    130                 135                 140

Ser Lys Ile Phe Gln Gln Tyr His Phe Glu Leu Met Ser Glu Leu Lys
145                 150                 155                 160

Asn Lys Gln Asn Phe Lys Phe Ser Leu Val Asn Ser
```

(2) INFORMATION FOR SEQ ID NO:2:

(i) SEQUENCE CHARACTERISTICS:
        (A) LENGTH: 1022 amino acids
        (B) TYPE: amino acid
        (C) STRANDEDNESS: single
        (D) TOPOLOGY: circular (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:2:

```
Met Ala Asn Ser Gln Leu Asp Arg Val Lys Gly Leu Ile Asp Ser Leu
 1               5                  10                  15

Asn Gln His Thr Lys Ser Ala Ala Lys Ser Gly Ala Gly Ala Leu Lys
            20                  25                  30

Asn Gly Leu Gly Gln Val Lys Gln Ala Gly Gln Lys Leu Ile Leu Tyr
        35                  40                  45

Ile Pro Lys Asp Tyr Gln Ala Ser Thr Gly Ser Ser Leu Asn Asp Leu
50                  55                  60

Val Lys Ala Ala Glu Ala Leu Gly Ile Glu Val His Arg Ser Glu Lys
65                  70                  75                  80

Asn Gly Thr Ala Leu Ala Lys Glu Leu Phe Gly Thr Thr Glu Lys Leu
                85                  90                  95

Leu Gly Phe Ser Glu Arg Gly Ile Ala Leu Phe Ala Pro Gln Phe Asp
            100                 105                 110

Lys Leu Leu Asn Lys Asn Gln Lys Leu Ser Lys Ser Leu Gly Gly Ser
        115                 120                 125

Ser Glu Ala Leu Gly Gln Arg Leu Asn Lys Thr Gln Thr Ala Leu Ser
    130                 135                 140

Ala Leu Gln Ser Phe Leu Gly Thr Ala Ile Ala Gly Met Asp Leu Asp
145                 150                 155                 160

Ser Leu Leu Arg Arg Arg Asn Gly Glu Asp Val Ser Gly Ser Glu
                165                 170                 175

Leu Ala Lys Ala Gly Val Asp Leu Ala Ala Gln Leu Val Asp Asn Ile
            180                 185                 190

Ala Ser Ala Thr Gly Thr Val Asp Ala Phe Ala Glu Gln Leu Gly Lys
        195                 200                 205

Leu Gly Asn Ala Leu Ser Asn Thr Arg Leu Ser Gly Leu Ala Ser Lys
    210                 215                 220

Leu Asn Asn Leu Pro Asp Leu Ser Leu Ala Gly Pro Gly Phe Asp Ala
225                 230                 235                 240

Val Ser Gly Ile Leu Ser Val Val Ser Ala Ser Phe Ile Leu Ser Asn
                245                 250                 255

Lys Asp Ala Asp Ala Gly Thr Lys Ala Ala Ala Gly Ile Glu Ile Ser
            260                 265                 270

Thr Lys Ile Leu Gly Asn Ile Gly Lys Ala Val Ser Gln Tyr Ile Ile
        275                 280                 285

Ala Gln Arg Val Ala Ala Gly Leu Ser Thr Thr Ala Ala Thr Gly Gly
    290                 295                 300

Leu Ile Gly Ser Val Val Ala Leu Ala Ile Ser Pro Leu Ser Phe Leu
305                 310                 315                 320

Asn Val Ala Asp Lys Phe Glu Arg Ala Lys Gln Leu Glu Gln Tyr Ser
                325                 330                 335
```

```
Glu Arg Phe Lys Lys Phe Gly Tyr Glu Gly Asp Ser Leu Leu Ala Ser
            340                 345                 350

Phe Tyr Arg Glu Thr Gly Ala Ile Glu Ala Ala Leu Thr Thr Ile Asn
            355                 360                 365

Ser Val Leu Ser Ala Ala Ser Ala Gly Val Gly Ala Ala Ala Thr Gly
            370                 375                 380

Ser Leu Val Gly Ala Pro Val Ala Ala Leu Val Ser Ala Ile Thr Gly
385                 390                 395                 400

Ile Ile Ser Gly Ile Leu Asp Ala Ser Lys Gln Ala Ile Phe Glu Arg
                405                 410                 415

Val Ala Thr Lys Leu Ala Asn Lys Ile Asp Glu Trp Glu Lys Lys His
            420                 425                 430

Gly Lys Asn Tyr Phe Glu Asn Gly Tyr Asp Ala Arg His Ser Ala Phe
            435                 440                 445

Leu Glu Asp Thr Phe Glu Leu Leu Ser Gln Tyr Asn Lys Glu Tyr Ser
            450                 455                 460

Val Glu Arg Val Val Ala Ile Thr Gln Gln Arg Trp Asp Val Asn Ile
465                 470                 475                 480

Gly Glu Leu Ala Gly Ile Thr Arg Lys Gly Ser Asp Thr Lys Ser Gly
                485                 490                 495

Lys Ala Tyr Val Asp Phe Phe Glu Glu Gly Lys Leu Leu Glu Lys Glu
            500                 505                 510

Pro Asp Arg Phe Asp Lys Lys Val Phe Asp Pro Leu Glu Gly Lys Ile
            515                 520                 525

Asp Leu Ser Ser Ile Asn Lys Thr Thr Leu Leu Lys Phe Val Thr Pro
            530                 535                 540

Val Phe Thr Ala Gly Glu Glu Ile Arg Glu Arg Lys Gln Thr Gly Lys
545                 550                 555                 560

Tyr Glu Tyr Met Thr Glu Leu Phe Val Lys Gly Lys Glu Lys Trp Val
                565                 570                 575

Val Thr Gly Val Gln Ser His Asn Ala Ile Tyr Asp Tyr Thr Asn Leu
            580                 585                 590

Ile Gln Leu Ala Ile Asp Lys Lys Gly Glu Lys Arg Gln Val Thr Ile
            595                 600                 605

Glu Ser His Leu Gly Glu Lys Asn Asp Arg Ile Tyr Leu Ser Ser Gly
            610                 615                 620

Ser Ser Ile Val Tyr Ala Gly Asn Gly His Asp Val Ala Tyr Tyr Asp
625                 630                 635                 640

Lys Thr Asp Thr Gly Tyr Leu Thr Phe Asp Gly Gln Ser Ala Gln Lys
                645                 650                 655

Ala Gly Glu Tyr Ile Val Thr Lys Glu Leu Lys Ala Asp Val Lys Val
            660                 665                 670

Leu Lys Glu Val Val Lys Thr Gln Asp Ile Ser Val Gly Lys Arg Ser
            675                 680                 685

Glu Lys Leu Glu Tyr Arg Asp Tyr Glu Leu Ser Pro Phe Glu Leu Gly
            690                 695                 700

Asn Gly Ile Arg Ala Lys Asp Glu Leu His Ser Val Glu Glu Ile Ile
705                 710                 715                 720

Gly Ser Asn Arg Lys Asp Lys Phe Phe Gly Ser Arg Phe Thr Asp Ile
                725                 730                 735

Phe His Gly Ala Lys Gly Asp Asp Glu Ile Tyr Gly Asn Asp Gly His
            740                 745                 750

Asp Ile Leu Tyr Gly Asp Asp Gly Asn Asp Val Ile His Gly Gly Asp
```

|                  |                  |           755                |                  |                     |           760              |                |                     |        765             |                    |               |           |
|------|------|------|------|------|------|------|------|------|------|------|------|

Gly Asn Asp His Leu Val Gly Gly Asn Gly Asn Asp Arg Leu Ile Gly
            770                        775                        780

Gly Lys Gly Asn Asn Phe Leu Asn Gly Gly Asp Gly Asp Asp Glu Leu
785                        790                        795                                    800

Gln Val Phe Glu Gly Gln Tyr Asn Val Leu Leu Gly Gly Ala Gly Asn
                        805                        810                        815

Asp Ile Leu Tyr Gly Ser Asp Gly Thr Asn Leu Phe Asp Gly Gly Val
                        820                        825                        830

Gly Asn Asp Lys Ile Tyr Gly Leu Gly Lys Asp Ile Tyr Arg Tyr
                        835                        840                        845

Ser Lys Glu Tyr Gly Arg His Ile Ile Ile Glu Lys Gly Gly Asp Asp
850                        855                        860

Asp Thr Leu Leu Leu Ser Asp Leu Ser Phe Lys Asp Val Gly Phe Ile
865                        870                        875                                    880

Arg Ile Gly Asp Asp Leu Leu Val Asn Lys Arg Ile Gly Gly Thr Leu
                        885                        890                        895

Tyr Tyr His Glu Asp Tyr Asn Gly Asn Ala Leu Thr Ile Lys Asp Trp
                        900                        905                        910

Phe Lys Glu Gly Lys Glu Gly Gln Asn Asn Lys Ile Glu Lys Ile Val
                        915                        920                        925

Asp Lys Asp Gly Ala Tyr Val Leu Ser Gln Tyr Leu Thr Glu Leu Thr
930                        935                        940

Ala Pro Gly Arg Gly Ile Asn Tyr Phe Asn Gly Leu Glu Glu Lys Leu
945                        950                        955                                    960

Tyr Tyr Gly Glu Gly Tyr Asn Ala Leu Pro Gln Leu Arg Lys Asp Ile
                        965                        970                        975

Glu Gln Ile Ile Ser Ser Thr Gly Ala Phe Thr Gly Asp His Gly Lys
                        980                        985                        990

Val Ser Val Gly Ser Gly Gly Pro Leu Val Tyr Asn Asn Ser Ala Asn
                        995                        1000                        1005

Asn Val Ala Asn Ser Leu Ser Tyr Ser Leu Ala Gln Ala Ala
            1010                        1015                        1020

(2) INFORMATION FOR SEQ ID NO:3:

(i) SEQUENCE CHARACTERISTICS:
        (A) LENGTH: 3762 base pairs
        (B) TYPE: nucleic acid
        (C) STRANDEDNESS: single
        (D) TOPOLOGY: circular (ii) MOLECULE TYPE: DNA (genomic)

(vi) ORIGINAL SOURCE:
        (A) ORGANISM: Actinobacillus pleuropneumoniae (xi) SEQUENCE DESCRIPTION: SEQ ID NO:3:

| | | | | | |
|---|---|---|---|---|---|
| AGATTAATGA | GCGATATTGT | TATAAAATCA | TAATGTAAAC | CTCATTTGTA | ATGAATTGGT | 60 |
| AAATTATATA | AATAATCAAA | AAACTTACTT | TTTTTTATTT | TTATCGGTAA | GTATTTACAA | 120 |
| TCAAGTCAGA | CAAACGGCAA | TATTGTTATA | AATCTGGGGG | GATGAATGAG | TAAAAAAATT | 180 |
| AATGGATTTG | AGGTTTTAGG | AGAGGTGGCA | TGGTTATGGG | CAAGTTCTCC | TTTACATCGA | 240 |
| AAGTGGCCGC | TTTCTTTGTT | AGCAATTAAT | GTGCTACCTG | CGATTGAGAG | TAATCAATAT | 300 |
| GTTTTGTTAA | AGCGTGACGG | TTTTCCTATT | GCATTTGTA | GCTGGGCAAA | TTTGAATTTG | 360 |
| GAAAATGAAA | TTAAATACCT | TGATGATGTT | GCCTCGCTAG | TTGCGGATGA | TTGGACTTCC | 420 |

```
GGCGATCGTC GATGGTTTAT AGATTGGATA GCACCGTTCG GAGACAGTGC CGCATTATAC       480

AAACATATGC GAGATAACTT CCCGAATGAG CTGTTTAGGG CTATTCGAGT TGATCCGGAC       540

TCTCGAGTAG GGAAAATTTC AGAATTTCAT GGAGGAAAAA TTGATAAGAA ACTGGCAAGT       600

AAAATTTTTC AACAATATCA CTTTGAATTA ATGAGTGAGC TAAAAAATAA ACAAAATTTT       660

AAATTTTCAT TAGTAAATAG CTAAGGAGAC AACATGGCTA ACTCTCAGCT CGATAGAGTC       720

AAAGGATTGA TTGATTCACT TAATCAACAT ACAAAAAGTG CAGCTAAATC AGGTGCCGGC       780

GCATTAAAAA ATGGTTTGGG ACAGGTGAAG CAAGCAGGGC AGAAATTAAT TTTATATATT       840

CCGAAAGATT ATCAAGCTAG TACCGGCTCA AGTCTTAATG ATTTAGTGAA AGCGGCGGAG       900

GCTTTAGGGA TCGAAGTACA TCGCTCGGAA AAAACGGTA CCGCACTAGC GAAAGAATTA       960

TTCGGTACAA CGGAAAAACT ATTAGGTTTC TCGGAACGAG GCATCGCATT ATTTGCACCT      1020

CAGTTTGATA AGTTACTGAA TAAGAACCAA AAATTAAGTA AATCGCTCGG CGGTTCATCG      1080

GAAGCATTAG GACAACGTTT AAATAAAACG CAAACGGCAC TTTCAGCCTT ACAAAGTTTC      1140

TTAGGTACGG CTATTGCGGG TATGGATCTT GATAGCCTGC TTCGTCGCCG TAGAAACGGT      1200

GAGGACGTCA GTGGTTCGGA ATTAGCTAAA GCAGGTGTGG ATCTAGCCGC TCAGTTAGTG      1260

GATAACATTG CAAGTGCAAC GGGTACGGTG GATGCGTTTG CCGAACAATT AGGTAAATTG      1320

GGCAATGCCT TATCTAACAC TCGCTTAAGC GGTTTAGCAA GTAAGTTAAA TAACCTTCCA      1380

GATTTAAGCC TTGCAGGACC TGGGTTTGAT GCCGTATCAG GTATCTTATC TGTTGTTTCG      1440

GCTTCATTCA TTTTAAGTAA TAAAGATGCC GATGCAGGTA CAAAAGCGGC GGCAGGTATT      1500

GAAATCTCAA CTAAAATCTT AGGCAATATC GGTAAAGCGG TTTCTCAATA TATTATTGCG      1560

CAACGTGTGG CGGCAGGCTT ATCCACAACT GCGGCAACCG GTGGTTTAAT CGGTTCGGTC      1620

GTAGCATTAG CGATTAGCCC GCTTTCGTTC TTAAATGTTG CGGATAAGTT TGAACGTGCG      1680

AAACAGCTTG AACAATATTC GGAGCGCTTT AAAAAGTTCG GTTATGAAGG TGATAGTTTA      1740

TTAGCTTCAT TCTACCGTGA AACCGGTGCG ATTGAAGCGG CATTAACCAC GATTAACAGT      1800

GTGTTAAGTG CGGCTTCCGC AGGTGTTGGG GCTGCTGCAA CCGGCTCATT AGTCGGTGCG      1860

CCGGTAGCAG CTTTAGTTAG TGCAATCACC GGTATTATTT CAGGTATTTT AGATGCTTCT      1920

AAACAGGCAA TCTTCGAACG AGTTGCAACG AAATTAGCGA ATAAGATTGA CGAATGGGAG      1980

AAAAAACACG GTAAAAACTA TTTTGAAAAC GGTTATGACG CCCGCCATTC CGCATTCTTA      2040

GAAGATACCT TGAATTGTT ATCACAATAC AATAAAGAGT ATTCGGTAGA GCGTGTCGTT       2100

GCTATTACGC AACAGCGTTG GGATGTCAAT ATCGGTGAAC TTGCCGGCAT TACTCGCAAA      2160

GGTTCTGATA CGAAAAGCGG TAAAGCTTAC GTTGATTTCT TTGAAGAAGG AAAACTTTTA      2220

GAGAAAGAAC CGGATCGTTT TGATAAAAAA GTGTTTGATC CGCTTGAAGG TAAAATCGAC      2280

CTTTCTTCAA TTAACAAAAC CACTTTATTG AAATTTGTTA CGCCGGTCTT TACCGCAGGT      2340

GAAGAGATTC GTGAGCGTAA GCAAACCGGT AAATACGAAT ATATGACCGA ATTATTCGTT      2400

AAAGGTAAAG AAAAATGGGT GGTAACCGGT GTGCAGTCAC ATAATGCGAT TTATGACTAT      2460

ACGAATCTTA TCCAATTAGC GATAGATAAA AAAGGTGAAA ACGTCAAGT GACCATTGAA       2520

TCTCATTTGG GTGAGAAAAA TGATCGTATA TATCTTTCAT CCGGTTCATC TATCGTATAT      2580

GCGGGTAACG GACATGATGT AGCATATTAC GATAAAACCG ATACAGGTTA CTTAACATTT      2640

GACGGACAAA GTGCACAGAA AGCCGGTGAA TATATTGTCA CTAAAGAACT TAAAGCTGAT      2700

GTAAAAGTTT TAAAGAAGT GGTTAAAACT CAGGATATTT CAGTTGGAAA ACGCAGTGAA       2760

AAATTAGAAT ATCGTGATTA TGAGTTAAGC CCATTCGAAC TTGGGAACGG TATCAGAGCT      2820
```

-continued

```
AAAGATGAAT TACATTCTGT TGAAGAAATT ATCGGTAGTA ATCGTAAAGA CAAATTCTTT    2880

GGTAGTCGCT TTACCGATAT TTTCCATGGT GCGAAAGGCG ATGATGAAAT CTACGGTAAT    2940

GACGGCCACG ATATCTTATA CGGAGACGAC GGTAATGATG TAATCCATGG CGGTGACGGT    3000

AACGACCATC TTGTTGGTGG TAACGGAAAC GACCGATTAA TCGGCGGAAA AGGTAATAAT    3060

TTCCTTAATG GCGGTGATGG TGACGATGAG TTGCAGGTCT TTGAGGGTCA ATACAACGTA    3120

TTATTAGGTG GTGCGGGTAA TGACATTCTG TATGGCAGCG ATGGTACTAA CTTATTTGAC    3180

GGTGGTGTAG GCAATGACAA AATCTACGGT GGTTTAGGTA AGGATATTTA TCGCTACAGT    3240

AAGGAGTACG GTCGTCATAT CATTATTGAG AAAGGCGGTG ATGATGATAC GTTATTGTTA    3300

TCGGATCTTA GTTTTAAAGA TGTAGGATTT ATCAGAATCG GTGATGATCT TCTTGTGAAT    3360

AAAAGAATCG GAGGAACACT GTATTACCAT GAAGATTACA ATGGGAATGC GCTCACGATT    3420

AAAGATTGGT TCAAGGAAGG TAAAGAAGGA CAAAATAATA AAATTGAAAA ATCGTTGAT     3480

AAAGATGGAG CTTATGTTTT AAGCCAATAT CTGACTGAAC TGACAGCTCC TGGAAGAGGT    3540

ATCAATTACT TTAATGGGTT AGAAGAAAAA TTGTATTATG GAGAAGGATA TAATGCACTT    3600

CCTCAACTCA GAAAAGATAT TGAACAAATC ATTTCATCTA CGGGTGCATT TACCGGTGAT    3660

CACGGAAAAG TATCTGTAGG CTCAGGCGGA CCGTTAGTCT ATAATAACTC AGCTAACAAT    3720

GTAGCAAATT CTTTGAGTTA TTCTTTAGCA CAAGCAGCTT AA                       3762
```

(2) INFORMATION FOR SEQ ID NO:4:

(i) SEQUENCE CHARACTERISTICS:
  (A) LENGTH: 707 amino acids
  (B) TYPE: amino acid
  (C) STRANDEDNESS: single
  (D) TOPOLOGY: linear (ii) MOLECULE TYPE: protein (vi) ORIGINAL SOURCE:
  (A) ORGANISM: Actinobacillus pleuropneumoniae (xi) SEQUENCE DESCRIPTION: SEQ ID NO:4:

```
Met Asp Phe Tyr Arg Glu Glu Asp Tyr Gly Leu Tyr Ala Leu Thr Ile
1               5                   10                  15

Leu Ala Gln Tyr His Asn Ile Ala Val Asn Pro Glu Glu Leu Lys His
            20                  25                  30

Lys Phe Asp Leu Glu Gly Lys Gly Leu Asp Leu Thr Ala Trp Leu Leu
        35                  40                  45

Ala Ala Lys Ser Leu Glu Leu Lys Ala Lys Gln Val Lys Lys Ala Ile
    50                  55                  60

Asp Arg Leu Ala Phe Ile Ala Leu Pro Ala Leu Val Trp Arg Glu Asp
65                  70                  75                  80

Gly Lys His Phe Ile Leu Thr Lys Leu Ile Asp Asn Glu Ala Lys Lys Tyr
                85                  90                  95

Leu Ile Phe Asp Leu Glu Thr His Asn Pro Arg Ile Leu Glu Gln Ala
            100                 105                 110

Glu Phe Glu Ser Leu Tyr Gln Gly Lys Leu Ile Leu Val Ala Ser Arg
        115                 120                 125

Ala Ser Ile Val Gly Lys Leu Ala Lys Phe Asp Phe Thr Trp Phe Ile
    130                 135                 140

Pro Ala Val Ile Lys Tyr Arg Lys Ile Phe Glu Thr Leu Ile Val
145                 150                 155                 160

Ser Ile Phe Leu Gln Ile Phe Ala Leu Ile Thr Pro Leu Phe Phe Gln
                165                 170                 175
```

```
Val Val Met Asp Lys Val Leu Val His Arg Gly Phe Ser Thr Leu Asn
            180                 185                 190

Val Ile Thr Val Ala Leu Ala Ile Val Val Leu Phe Glu Ile Val Leu
            195                 200                 205

Asn Gly Leu Arg Thr Tyr Ile Phe Ala His Ser Thr Ser Arg Ile Asp
            210                 215                 220

Val Glu Leu Gly Ala Arg Leu Phe Arg His Leu Leu Ala Leu Pro Ile
225                 230                 235                 240

Ser Tyr Phe Glu Asn Arg Arg Val Gly Asp Thr Val Ala Arg Val Arg
            245                 250                 255

Glu Leu Asp Gln Ile Arg Asn Phe Leu Thr Gly Gln Ala Leu Thr Ser
            260                 265                 270

Val Leu Asp Leu Met Phe Ser Phe Ile Phe Phe Ala Val Met Trp Tyr
            275                 280                 285

Tyr Ser Pro Lys Leu Thr Leu Val Ile Leu Gly Ser Leu Pro Phe Tyr
            290                 295                 300

Met Gly Trp Ser Ile Phe Ile Ser Pro Ile Leu Arg Arg Arg Leu Asp
305                 310                 315                 320

Glu Lys Phe Ala Arg Gly Ala Asp Asn Gln Ser Phe Leu Val Glu Ser
            325                 330                 335

Val Thr Ala Ile Asn Thr Ile Lys Ala Leu Ala Val Thr Pro Gln Met
            340                 345                 350

Thr Asn Thr Trp Asp Lys Gln Leu Ala Ser Tyr Val Ser Ala Gly Phe
            355                 360                 365

Arg Val Thr Thr Leu Ala Thr Ile Gly Gln Gln Gly Val Gln Phe Ile
            370                 375                 380

Gln Lys Val Val Met Val Ile Thr Leu Trp Leu Gly Ala His Leu Val
385                 390                 395                 400

Ile Ser Gly Asp Leu Ser Ile Gly Gln Leu Ile Ala Phe Asn Met Leu
            405                 410                 415

Ser Gly Gln Val Ile Ala Pro Val Ile Arg Leu Ala Gln Leu Trp Gln
            420                 425                 430

Asp Phe Gln Gln Val Gly Ile Ser Val Thr Arg Leu Gly Asp Val Leu
            435                 440                 445

Asn Ser Pro Thr Glu Ser Tyr Gln Gly Lys Leu Ala Leu Pro Glu Ile
            450                 455                 460

Lys Gly Asp Ile Thr Phe Arg Asn Ile Arg Phe Arg Tyr Lys Pro Asp
465                 470                 475                 480

Ala Pro Val Ile Leu Asn Asp Val Asn Leu Ser Ile Gln Gln Gly Glu
            485                 490                 495

Val Ile Gly Ile Val Gly Arg Ser Gly Ser Gly Lys Ser Thr Leu Thr
            500                 505                 510

Lys Leu Ile Gln Arg Phe Tyr Ile Pro Glu Asn Gly Gln Val Leu Ile
            515                 520                 525

Asp Gly His Asp Leu Ala Leu Ala Asp Pro Asn Trp Leu Arg Arg Gln
            530                 535                 540

Val Gly Val Val Leu Gln Asp Asn Val Leu Leu Asn Arg Ser Ile Arg
545                 550                 555                 560

Asp Asn Ile Ala Leu Ala Asp Pro Gly Met Pro Met Glu Lys Ile Val
            565                 570                 575

His Ala Ala Lys Leu Ala Gly Ala His Glu Phe Ile Ser Glu Leu Arg
            580                 585                 590

Glu Gly Tyr Asn Thr Ile Val Gly Glu Gln Gly Ala Gly Leu Ser Gly
```

```
                    595                 600                 605
Gly Gln Arg Gln Arg Ile Ala Ile Ala Arg Ala Leu Val Asn Asn Pro
            610                 615                 620
Lys Ile Leu Ile Phe Asp Glu Ala Thr Ser Ala Leu Asp Tyr Glu Ser
625                 630                 635                 640
Glu His Ile Ile Met Arg Asn Met His Gln Ile Cys Lys Gly Arg Thr
                    645                 650                 655
Val Ile Ile Ile Ala His Arg Leu Ser Thr Val Lys Asn Ala Asp Arg
            660                 665                 670
Ile Ile Val Met Glu Lys Gly Gln Ile Val Gln Gly Lys His Lys
            675                 680                 685
Glu Leu Leu Ala Asp Pro Asn Gly Leu Tyr His Tyr Leu His Gln Leu
690                 695                 700
Gln Ser Glu
705

(2) INFORMATION FOR SEQ ID NO:5:

(i) SEQUENCE CHARACTERISTICS:
         (A) LENGTH: 478 amino acids
         (B) TYPE: amino acid
         (C) STRANDEDNESS: single
         (D) TOPOLOGY: linear (ii) MOLECULE TYPE: protein (vi) ORIGINAL SOURCE:
         (A) ORGANISM: Actinobacillus pleuropneumoniae (xi) SEQUENCE DESCRIPTION: SEQ ID NO:5:

Met Lys Thr Trp Leu Met Gly Leu Tyr Glu Phe Phe Gln Arg Tyr Lys
1               5                   10                  15
Thr Val Trp Thr Glu Ile Trp Lys Ile Arg His Gln Leu Asp Thr Pro
            20                  25                  30
Asp Arg Glu Lys Asp Glu Asn Glu Phe Leu Pro Ala His Leu Glu Leu
        35                  40                  45
Ile Glu Thr Pro Val Ser Lys Lys Pro Arg Leu Ile Ala Tyr Leu Ile
50                  55                  60
Met Leu Phe Leu Phe Leu Ala Leu Val Ile Ser Ile Val Ser His Val
65                  70                  75                  80
Glu Ile Val Ala Thr Ala Thr Gly Lys Leu Ala Phe Ser Asp Arg Ser
                    85                  90                  95
Lys Glu Ile Lys Pro Ile Glu Asn Ala Leu Val Lys Glu Ile Phe Val
            100                 105                 110
Gln Asp Gly Gln Phe Val Glu Lys Asp Gln Leu Leu His Leu Thr
        115                 120                 125
Ala Leu Gly Ala Asp Ala Asp Gln Gln Lys Thr Lys Ser Ser Leu Ser
130                 135                 140
Leu Thr Lys Leu Glu Arg Tyr Arg Tyr Glu Ile Leu Leu Glu Ala Val
145                 150                 155                 160
Ala Ala Asp Arg Leu Pro Leu Ile Glu Leu Thr Lys Asp Glu Phe Lys
                    165                 170                 175
His Ala Thr Glu Glu Asp Lys Thr Arg Ile Arg Tyr Leu Ile Thr Glu
            180                 185                 190
Gln Phe Glu Ala Trp Gln Lys Gln Lys Tyr Gln Lys Glu Leu Ala Leu
        195                 200                 205
Gln Arg Arg Glu Ala Glu Lys Gln Thr Val Leu Ala Asn Ile Arg Lys
210                 215                 220
```

```
Tyr Glu Gly Ile Ser Arg Val Glu Asn Glu Arg Leu Lys Asp Leu Lys
225                 230                 235                 240

Lys Leu Phe Asn Ser Lys Ser Thr Ser Lys His Asp Val Leu Thr Gln
            245                 250                 255

Glu Asn Arg His Ile Glu Ala Val Asn Glu Leu Ala Val Tyr Lys Ser
                260                 265                 270

Arg Leu Asn Glu Val Glu Ser Asp Leu Arg Gln Ala Lys Glu Glu Ile
            275                 280                 285

His Leu Ile Thr Gln Leu Phe Arg Ala Asp Ile Leu Glu Lys Leu Lys
290                 295                 300

Gln Asn Val Glu Ala Glu Lys Gln Leu Ser Leu Glu Leu Glu Lys Asn
305                 310                 315                 320

Glu Gln Arg Gln Ile Ala Ser Val Ile Arg Ala Pro Val Ser Gly Thr
                325                 330                 335

Val Gln Gln Leu Lys Thr His Thr Val Gly Gly Val Val Thr Thr Ala
            340                 345                 350

Glu Thr Leu Met Val Ile Ala Pro Glu Asp Asp Val Leu Glu Val Thr
            355                 360                 365

Ala Leu Ile Gln Asn Lys Asp Ile Gly Phe Ile Glu Val Gly Gln Asp
370                 375                 380

Ala Val Ile Lys Val Glu Thr Phe Pro Tyr Thr Arg Tyr Gly Tyr Leu
385                 390                 395                 400

Met Gly Lys Val Lys Asn Ile Thr Leu Glu Ala Ile Glu His Pro Gln
                405                 410                 415

Leu Gly Leu Val Phe Asn Ser Ile Ile Ser Ile Asp Arg Lys Thr Leu
            420                 425                 430

Ser Gly Lys Asp Gly Lys Glu Ile Glu Leu Gly Ser Gly Met Ser Val
            435                 440                 445

Thr Ala Glu Ile Lys Thr Gly Glu Arg Ser Val Ile Ser Tyr Leu Leu
            450                 455                 460

Ser Pro Leu Glu Glu Ser Val Ser Glu Ser Leu Arg Glu Arg
465                 470                 475

(2) INFORMATION FOR SEQ ID NO:6:

(i) SEQUENCE CHARACTERISTICS:
        (A) LENGTH: 5120 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Actinobacillus pleuropneumoniae (xi) SEQUENCE DESCRIPTION: SEQ ID NO:6:

TCGTCATATC ATTATTGAGA AAGGCGGTGA TGATGATACG TTATTGTTAT CGGATCTTAG      60

TTTTAAAGAT GTAGGATTTA TCAGAATCGG TGATGATCTT CTTGTGAATA AAAGAATCGG    120

AGGAACACTG TATTACCATG AAGATTACAA TGGGAATGCG CTCACGATTA AGATTGGTT     180

CAAGGAAGGT AAAGAAGGAC AAAATAATAA AATTGAAAAA ATCGTTGATA AGATGGAGC     240

TTATGTTTTA AGCCAATATC TGACTGAACT GACAGCTCCT GGAAGAGGTA TCAATTACTT    300

TAATGGGTTA GAAGAAAAAT TGTATTATGG AGAAGGATAT AATGCACTTC CTCAACTCAG    360

AAAAGATATT GAACAAATCA TTTCATCTAC GGGTGCATTT ACCGGTGATC ACGGAAAAGT    420

ATCTGTAGGC TCAGGCGGAC CGTTAGTCTA TAATAACTCA GCTAACAATG TAGCAAATTC    480
```

```
TTTGAGTTAT TCTTTAGCAC AAGCAGCTTA AGATAGTTAT TTTTAGATGA TAAATAGCAA     540

TCCTATATAT ATTAGGTGTG TAGGATTGCT ATTTTATTTA TGGAGGAGCA AATGGATTTT     600

TATCGGGAAG AAGACTACGG ATTATACGCA CTGACGATTT TAGCCCAGTA CCATAATATT     660

GCTGTAAATC CGGAAGAACT AAAACATAAA TTCGACCTTG AAGGAAAAGG CTTAGATCTA     720

ACCGCTTGGC TATTAGCCGC AAAATCATTA GAACTTAAAG CAAACAAGT AAAAAAAGCG      780

ATTGATCGTT TGGCGTTTAT CGCACTACCG GCACTTGTAT GGCGAGAAGA CGGTAAACAT     840

TTTATTTTGA CTAAAATTGA TAATGAAGCA AAAAAATATT TAATTTTTGA TTTGAAAACG     900

CATAATCCTC GCATTTTGGA ACAAGCGGAA TTCGAGAGCT TATACCAAGG AAAACTGATT     960

TTAGTTGCAT CAAGAGCTTC CATCGTAGGT AAGCTGGCAA AGTTTGACTT CACTTGGTTT    1020

ATACCGGCGG TAATTAAGTA TCGTAAGATT TTTATTGAAA CGTTAATTGT TTCAATTTTT    1080

TTGCAAATTT TCGCACTAAT TACACCGCTT TTTTTCCAAG TCGTGATGGA TAAAGTCTTG    1140

GTACACCGAG GTTTTTCAAC CTTAAATGTG ATTACGGTGG CATTAGCGAT CGTCGTGCTG    1200

TTTGAAATTG TGCTAAACGG TTTACGTACC TATATTTTTG CGCATAGTAC CAGCCGTATT    1260

GATGTGGAGT TGGGAGCAAG ATTATTCAGA CATTTATTAG CACTCCCAAT CTCTTATTTT    1320

GAAAATCGTC GAGTCGGCGA TACGGTGGCT CGTGTACGAG AACTCGATCA AATTCGTAAC    1380

TTCTTAACCG GGCAGGCACT TACTTCCGTG TTGGATTTAA TGTTTTCCTT TATCTTCTTT    1440

GCAGTGATGT GGTATTACAG CCCTAAACTT ACTCTTGTGA TTTTAGGCTC GTTACCGTTT    1500

TATATGGGT GGTCGATTTT TATCAGCCCT ATTTTACGTC GCCGTTTAGA TGAAAAATTC    1560

GCACGTGGTG CGGACAATCA GTCATTCTTA GTGGAATCGG TGACTGCAAT CAATACGATT    1620

AAAGCGTTGG CGGTTACCCC TCAAATGACT AATACCTGGG ATAAGCAATT AGCCAGCTAT    1680

GTATCGGCGG GATTCCGTGT AACCACATTA GCTACTATCG GACAGCAAGG TGTACAATTT    1740

ATTCAAAAAG TCGTGATGGT TATTACCTTA TGGCTAGGCG CACATTTAGT GATTTCAGGC    1800

GATTTAAGTA TCGGACAATT AATCGCATTT AATATGTTAT CCGGTCAAGT GATTGCACCG    1860

GTGATTCGTT TAGCGCAACT TTGGCAAGAT TTCCAACAAG TGGGAATTTC GGTAACGCGT    1920

TTAGGTGATG TTTTAAACTC TCCGACCGAG AGCTATCAAG GAAAATTGGC GTTACCGGAA    1980

ATTAAAGGCG ATATTACCTT CCGTAATATA CGCTTCCGCT ACAAACCGGA TGCGCCGGTG    2040

ATTTTAAATG ATGTGAATTT ATCGATTCAG CAAGGTGAAG TGATCGGTAT CGTAGGACGT    2100

TCAGGCTCAG GGAAGAGCAC CTTAACGAAA TTAATTCAAC GTTTTTATAT TCCGGAAAAC    2160

GGTCAGGTAT TAATAGATGG GCATGATTTA GCATTGGCGG ATCCGAACTG GCTACGTCGT    2220

CAAGTCGGGG TGGTATTACA AGATAACGTA CTATTAAATC GTAGTATTCG AGATAATATT    2280

GCCTTAGCGG ATCCGGGTAT GCCAATGGAA AAAATTGTCC ATGCGGCAAA ATTAGCCGGC    2340

GCACATGAAT TTATTTCTGA ATTGCGTGAG GGATATAACA CGATTGTTGG TGAGCAAGGT    2400

GCGGGCTAT CTGGCGGGCA ACGCCAACGT ATTGCGATTG CACGCGCTTT GGTGAATAAC    2460

CCGAAAATCT TAATTTTTGA TGAAGCGACC AGCGCATTAG ATTATGAATC CGAGCATATC    2520

ATCATGCGCA ATATGCACCA GATTTGTAAA GGGAGAACGG TAATTATCAT TGCACACCGT    2580

TTATCTACGG TAAAAAATGC CGACCGTATT ATTGTGATGA AAAAAGGTCA GATTGTGGAA    2640

CAAGGTAAGC ATAAAGAGCT GCTTGCTGAT CCAAACGGCT TATATCACTA CTTACACCAA    2700

TTACAATCGG AATAGGAGGA CTTATGAAAA CATGGCTAAT GGGTTATAT GAGTTTTTCC     2760

AACGCTATAA AACGGTTTGG ACGGAGATCT GGAAAATTCG TCATCAATTG GATACGCCGG    2820

ATCGAGAAAA GGATGAAAAT GAATTTTTAC CTGCACACTT AGAGCTGATT GAAACACCGG    2880
```

```
TGTCAAAAAA ACCGAGATTG ATCGCTTATT TAATTATGCT GTTCCTATTT TTGGCATTAG      2940

TTATTTCAAT TGTCAGTCAC GTAGAAATTG TGGCGACCGC AACGGGTAAA TTAGCGTTTA      3000

GCGACCGTAG CAAAGAAATT AAGCCGATTG AAAACGCCTT GGTTAAAGAA ATCTTTGTGC      3060

AAGACGGACA ATTTGTTGAG AAAGATCAGT TGCTGTTACA CTTGACCGCA TTGGGAGCCG      3120

ATGCGGATCA ACAAAAAACC AAAAGTTCGT TATCGCTGAC TAAATTGGAA CGTTATCGTT      3180

ATGAAATTTT ATTAGAGGCG GTTGCGGCGG ATAGGTTGCC GCTCATTGAA CTGACAAAGG      3240

ATGAATTTAA ACATGCTACG GAAGAAGATA AAACCAGAAT TCGCTATTTG ATCACCGAGC      3300

AATTTGAAGC TTGGCAAAAG CAAAAGTATC AAAAAGAATT AGCTTTGCAA CGTAGAGAAG      3360

CAGAAAAACA AACGGTTCTA GCTAATATTC GTAAATATGA GGGAATCAGT CGAGTTGAAA      3420

ATGAAAGATT AAAAGATCTT AAAAAATTAT TTAATTCGAA ATCGACTTCT AAACATGATG      3480

TCTTGACTCA AGAAAATCGT CATATCGAAG CGGTAAATGA GTTGGCGGTG TATAAATCTC      3540

GGTTGAATGA AGTGGAAAGT GACTTACGTC AAGCCAAAGA GGAAATACAT TTAATAACTC      3600

AGTTGTTTAG AGCCGATATT CTGGAGAAGT TGAAACAAAA TGTTGAAGCG GAGAAACAGC      3660

TTTCGCTCGA ATTAGAAAAA AATGAGCAGC GTCAAATTGC TTCGGTGATT CGTGCGCCGG      3720

TTTCCGGTAC GGTTCAGCAA CTTAAAACCC ATACGGTAGG CGGCGTCGTG ACGACTGCCG      3780

AAACCTTGAT GGTAATTGCT CCGGAAGATG ATGTTTTAGA GGTAACGGCG TTAATTCAAA      3840

ATAAGGATAT CGGTTTTATC GAGGTCGGTC AGGATGCGGT GATTAAAGTA GAAACTTTTC      3900

CTTATACTCG TTACGGCTAT TTAATGGGTA AAGTAAAAAA TATCACGCTG GAAGCCATCG      3960

AACATCCGCA ACTCGGTCTA GTTTTTAACT CGATTATTTC TATTGATAGA AAAACTTTAT      4020

CCGGCAAAGA CGGCAAAGAA ATTGAACTTG GATCAGGTAT GAGTGTGACG GCGGAAATTA      4080

AAACTGGAGA ACGTAGCGTT ATTAGTTATT TACTCAGTCC GTTGGAAGAA TCCGTTTCGG      4140

AGAGTTTAAG AGAACGCTAA AGCAGATAAA ACAAGCGGCC ATATTTCTT ACTTTTTTGC       4200

AAAAAACGTA TGAAATATGA CCGCTTGTCG TTTGTAAAAG ACTATTTATT TACAATAATT      4260

TTAGCACCGT TAGAAAATAC GATCTGACGA GCTTCAAATT GAGCGGAGAG CTGTGCTTGC      4320

GGGTTTAGAA ATACGGCTTG TGCTTCTTGC GGTAAGTCTG AAACCGGTAC GCAAAGGCAA      4380

GTTCCGCCGT GGTTTGGCGT TTTAAGTTAT CTTTAAAGGT AACGGGCGCA TCTTGCGTGA      4440

GGATAACTTT ATCATTGTAA ACATAGTTTA CCGCCCATTG AACGATACGA ATATTGCGTT      4500

TGGTTTTATT TTCAATACTG TATTTAAAGC TAACCATCGG CTGCCCTTCT TTATTTTTAG      4560

CCAATTCATA ACCGAAAAAA CGTAACCCGA TACTGTCATT AAATTGTTTA AGGCGTTTTT      4620

CTTTAGCCGA AAGAGGTGCA TTTTTCGTTA CTGATTTATG TTCAACCGTC GGTTGAATTT      4680

TATTGCCTTC AGCTTGAGCA TTAAACGCTA AAAAGAATGA TGCTACCGCC GTGCTAAGTA      4740

ATTTAATGTG TTTCATAATT CACCTCGTAA TGAGAGCTAA AAGCCGACTT GATATATTAC      4800

GCTATATATT GTCAGATTTA CGGCACAGTT GCAATGACCG CATAACCGTC CGATTCGGCA      4860

ATAATCTCGA CTTGGCTTTC CGCCGCAATG AAAATCGCTT CGCCTTGTTG GAGATAAATG      4920

GACTCTTCAC CGAGGTCGAT ATAGATACTG CCTTTCATCA CCAATAAGAT ACTTGCACAG      4980

TCGGCCGTAA AGTTTTCTTC GTCAAATGCG TTGAATTGCA TATGTTGCAA TGCAAAATCT      5040

TTCGCTTCAG GCGTCGGATA AAGATGAATG AAACCGTCGT TTTCTTGATA AGGCGGAATA      5100

ACTTCGGGGT AATCGGGCGA                                                  5120

(2) INFORMATION FOR SEQ ID NO:7:
```

-continued

```
    (i) SEQUENCE CHARACTERISTICS:
        (A) LENGTH: 159 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:7:

Met Leu Lys Asn Asp Phe Asn Val Leu Gly Gln Ile Ala Trp Leu Trp
1               5                  10                  15

Ala Asn Ser Pro Met His Arg Asn Trp Ser Val Ser Leu Leu Met Lys
            20                  25                  30

Asn Val Ile Pro Ala Ile Glu Asn Asp Gln Tyr Leu Leu Leu Val Asp
        35                  40                  45

Asp Gly Phe Pro Ile Ala Tyr Cys Ser Trp Ala Lys Leu Thr Leu Glu
    50                  55                  60

Ser Glu Ala Arg Tyr Val Lys Asp Thr Asn Ser Leu Lys Ile Asp Asp
65                  70                  75                  80

Trp Asn Ala Gly Asp Arg Ile Trp Ile Ile Asp Trp Ile Ala Pro Phe
                85                  90                  95

Gly Asp Ser Ser Leu Leu Tyr Lys His Met Arg Gln Arg Phe Pro Tyr
            100                 105                 110

Asp Ile Gly Arg Ala Ile Arg Ile Tyr Pro Ser Lys Lys Asp Thr Gly
        115                 120                 125

Lys Ile Ile Tyr Leu Lys Gly Gly Lys Ile Thr Lys Lys Val Ala Glu
    130                 135                 140

Lys Thr Phe Leu Gln Tyr Glu Gln Glu Leu Ile Thr Ala Leu Gln
145                 150                 155

(2) INFORMATION FOR SEQ ID NO:8:

(i) SEQUENCE CHARACTERISTICS:
        (A) LENGTH: 956 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:8:

Met Ser Lys Ile Thr Leu Ser Ser Leu Lys Ser Ser Leu Gln Gln Gly
1               5                  10                  15

Leu Lys Asn Gly Lys Asn Lys Leu Asn Gln Ala Gly Thr Thr Leu Lys
            20                  25                  30

Asn Gly Leu Thr Gln Thr Gly His Ser Leu Gln Asn Gly Ala Lys Lys
        35                  40                  45

Leu Ile Leu Tyr Ile Pro Gln Gly Tyr Asp Ser Gln Gly Asn Gly
    50                  55                  60

Val Gln Asp Leu Val Lys Ala Ala Asn Asp Leu Gly Ile Glu Val Trp
65                  70                  75                  80

Arg Glu Glu Arg Ser Asn Leu Asp Ile Ala Lys Thr Ser Phe Asp Thr
                85                  90                  95

Thr Gln Lys Ile Leu Gly Phe Asp Arg Gly Ile Val Leu Phe Ala
        100                 105                 110
```

```
Pro Gln Leu Asp Asn Leu Leu Lys Lys Asn Pro Lys Ile Gly Asn Thr
        115                 120                 125
Leu Gly Ser Ala Ser Ser Ile Ser Gln Asn Ile Gly Lys Ala Asn Thr
    130                 135                 140
Val Leu Gly Gly Ile Gln Ser Ile Leu Gly Ser Val Leu Ser Gly Val
145                 150                 155                 160
Asn Leu Asn Glu Leu Leu Gln Asn Lys Asp Pro Asn Gln Leu Glu Leu
                165                 170                 175
Ala Lys Ala Gly Leu Glu Leu Thr Asn Glu Leu Val Gly Asn Ile Ala
            180                 185                 190
Ser Ser Val Gln Thr Val Asp Ala Phe Ala Glu Gln Ile Ser Lys Leu
        195                 200                 205
Gly Ser His Leu Gln Asn Val Lys Gly Leu Gly Leu Ser Asn Lys
        210                 215                 220
Leu Gln Asn Leu Pro Asp Leu Gly Lys Ala Ser Leu Gly Leu Asp Ile
225                 230                 235                 240
Ile Ser Gly Leu Leu Ser Gly Ala Ser Ala Gly Leu Ile Leu Ala Asp
                245                 250                 255
Lys Glu Ala Ser Thr Glu Lys Lys Ala Ala Gly Val Glu Phe Ala
            260                 265                 270
Asn Gln Ile Ile Gly Asn Val Thr Lys Ala Val Ser Ser Tyr Ile Leu
        275                 280                 285
Ala Gln Arg Val Ala Ser Gly Leu Ser Ser Thr Gly Pro Val Ala Ala
    290                 295                 300
Leu Ile Ala Ser Thr Val Ala Leu Ala Val Ser Pro Leu Ser Phe Leu
305                 310                 315                 320
Asn Val Ala Asp Lys Phe Lys Gln Ala Asp Leu Ile Lys Ser Tyr Ser
                325                 330                 335
Glu Arg Phe Gln Lys Leu Gly Tyr Asp Gly Asp Arg Leu Leu Ala Asp
            340                 345                 350
Phe His Arg Glu Thr Gly Thr Ile Asp Ala Ser Val Thr Thr Ile Asn
        355                 360                 365
Thr Ala Leu Ala Ala Ile Ser Gly Gly Val Gly Ala Ala Ser Ala Gly
    370                 375                 380
Ser Leu Val Gly Ala Pro Val Ala Leu Leu Val Ala Gly Val Thr Gly
385                 390                 395                 400
Leu Ile Thr Thr Ile Leu Glu Tyr Ser Lys Gln Ala Met Phe Glu His
                405                 410                 415
Val Ala Asn Lys Val His Asp Arg Ile Val Glu Trp Glu Lys Lys His
            420                 425                 430
Asn Lys Asn Tyr Phe Glu Gln Gly Tyr Asp Ser Arg His Leu Ala Asp
        435                 440                 445
Leu Gln Asp Asn Met Lys Phe Leu Ile Asn Leu Asn Lys Glu Leu Gln
    450                 455                 460
Ala Glu Arg Val Val Ala Ile Thr Gln Gln Arg Trp Asp Asn Gln Ile
465                 470                 475                 480
Gly Asp Leu Ala Ala Ile Ser Arg Arg Thr Asp Lys Ile Ser Ser Gly
                485                 490                 495
Lys Ala Tyr Val Asp Ala Phe Glu Glu Gly Gln His Gln Ser Tyr Asp
            500                 505                 510
Ser Ser Val Gln Leu Asp Asn Lys Asn Gly Ile Ile Asn Ile Ser Asn
        515                 520                 525
Thr Asn Arg Lys Thr Gln Ser Val Leu Phe Arg Thr Pro Leu Leu Thr
    530                 535                 540
```

-continued

```
Pro Gly Glu Glu Asn Arg Glu Arg Ile Gln Glu Gly Lys Asn Ser Tyr
545                 550                 555                 560

Ile Thr Lys Leu His Ile Gln Arg Val Asp Ser Trp Thr Val Thr Asp
                565                 570                 575

Gly Asp Ala Ser Ser Val Asp Phe Thr Asn Val Val Gln Arg Ile
            580                 585                 590

Ala Val Lys Phe Asp Asp Ala Gly Asn Ile Ile Glu Ser Lys Asp Thr
        595                 600                 605

Lys Ile Ile Ala Asn Leu Gly Ala Gly Asn Asp Asn Val Phe Val Gly
    610                 615                 620

Ser Ser Thr Thr Val Ile Asp Gly Gly Asp His Asp Arg Val His
625                 630                 635                 640

Tyr Ser Arg Gly Glu Tyr Gly Ala Leu Val Ile Asp Ala Thr Ala Glu
                645                 650                 655

Thr Glu Lys Gly Ser Tyr Ser Val Lys Arg Tyr Val Gly Asp Ser Lys
                660                 665                 670

Ala Leu His Glu Thr Ile Ala Thr His Gln Thr Asn Val Gly Asn Arg
            675                 680                 685

Glu Glu Lys Ile Glu Tyr Arg Arg Glu Asp Asp Arg Phe His Thr Gly
690                 695                 700

Tyr Thr Val Thr Asp Ser Leu Lys Ser Val Glu Ile Ile Gly Ser
705                 710                 715                 720

Gln Phe Asn Asp Ile Phe Lys Gly Ser Gln Phe Asp Val Phe His
                725                 730                 735

Gly Gly Asn Gly Val Asp Thr Ile Asp Gly Asn Asp Gly Asp His
            740                 745                 750

Leu Phe Gly Gly Ala Gly Asp Val Ile Asp Gly Asn Gly Asn
        755                 760                 765

Asn Phe Leu Val Gly Gly Thr Gly Asn Asp Ile Ile Ser Gly Gly Lys
    770                 775                 780

Asp Asn Asp Ile Tyr Val His Lys Thr Gly Asp Gly Asn Asp Ser Ile
785                 790                 795                 800

Thr Asp Ser Gly Gly Gln Asp Lys Leu Ala Phe Ser Asp Val Asn Leu
            805                 810                 815

Lys Asp Leu Thr Phe Lys Lys Val Asp Ser Ser Leu Glu Ile Ile Asn
        820                 825                 830

Gln Lys Gly Glu Lys Val Arg Ile Gly Asn Trp Phe Leu Glu Asp Asp
    835                 840                 845

Leu Ala Ser Thr Val Ala Asn Tyr Lys Ala Thr Asn Asp Arg Lys Ile
850                 855                 860

Glu Glu Ile Ile Gly Lys Gly Gly Glu Arg Ile Thr Ser Glu Gln Val
865                 870                 875                 880

Asp Lys Leu Ile Lys Glu Gly Asn Asn Gln Ile Ser Ala Glu Ala Leu
            885                 890                 895

Ser Lys Val Val Asn Asp Tyr Asn Thr Ser Lys Asp Arg Gln Asn Val
        900                 905                 910

Ser Asn Ser Leu Ala Lys Leu Ile Ser Ser Val Gly Ser Phe Thr Ser
    915                 920                 925

Ser Ser Asp Phe Arg Asn Asn Leu Gly Thr Tyr Val Pro Ser Ser Ile
930                 935                 940

Asp Val Ser Asn Asn Ile Gln Leu Ala Arg Ala Ala
945                 950                 955
```

(2) INFORMATION FOR SEQ ID NO:9:

(i) SEQUENCE CHARACTERISTICS:
        (A) LENGTH: 4731 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Actinobacillus pleuropneumoniae (xi) SEQUENCE DESCRIPTION: SEQ ID NO:9:

```
CTTAACCATT ACAGAACGTT GGTACAAAAA ATTTTACAGG AAAATGATGG ATAGTCCTTA      60
ACAAAAATTA ATGTTTTATT TCCTATAAAA CATCCGACCA GTATTATTTT TGATTAAAAA     120
AAGAACAAAC AGATCATGAC AAACGTTTGC CTTGTTTTCC TTCACAAAAA TATTATGGTT     180
TTTTATTTAG AATAAATTAT CTATATTCAT TTTTTAGGGA ATGGGAGGGA TGATGCTAAA     240
AAATGATTTT AACGTATTGG GACAAATTGC TTGGTTATGG GCAAATTCTC CAATGCACCG     300
AAATTGGTCA GTTTCACTGT TAATGAAGAA TGTTATTCCT GCAATTGAAA ATGACCAATA     360
TTTGTTACTA GTTGATGATG GTTTTCCTAT TGCATATTGC AGTTGGGCCA AATTAACTCT     420
AGAGAGTGAG GCTCGCTATG TAAAGGACAC CAATTCATTA AAAATAGATG ATTGGAATGC     480
AGGAGATCGT ATATGGATCA TTGATTGGAT TGCCCCATTC GGGGATTCAT CTCTATTGTA     540
TAAACATATG AGACAACGTT TTCCATACGA TATTGGAAGG GCAATTAGAA TCTATCCTAG     600
CAAAAAAGAT ACTGGAAAAA TCATATATTT AAAAGGAGGA AAAATAACAA AAAAGTAGC     660
TGAAAAGACA TTTCTTCAGT ATGAGCAAGA GTTAATAACA GCTCTACAAT AATATCTTTA     720
AATGATCAAT TATATAAAGG AGACTCTTTT ATGTCAAAAA TCACTTTGTC ATCATTAAAA     780
TCGTCCTTAC AACAAGGATT GAAAAATGGG AAAAACAAGT TAAATCAAGC AGGTACAACA     840
CTGAAGAATG GTTTAACTCA AACTGGTCAT TCTCTACAGA ATGGGCTAA AAAATTAATC     900
TTATATATTC CTCAAGGCTA TGATTCGGGT CAAGGAAATG GAGTTCAAGA TTTAGTTAAA     960
GCTGCTAATG ATTTAGGTAT TGAAGTATGG CGAGAAGAAC GCAGCAATTT GGACATTGCA    1020
AAAACTAGCT TGATACAAC TCAGAAAATT CTAGGTTTTA CTGATAGAGG AATTGTATTA    1080
TTTGCACCTC AGCTAGATAA TTTATTAAAG AAGAATCCTA AAATTGGCAA TACATTAGGA    1140
AGTGCTTCTA GCATCTCACA AAATATAGGT AAAGCCAATA CTGTATTAGG TGGTATTCAA    1200
TCTATTTTAG GATCTGTTTT ATCTGGAGTA AATCTGAATG AATTACTTCA AAATAAAGAT    1260
CCTAATCAAT TAGAACTTGC AAAAGCAGGG CTAGAACTGA CTAATGAATT AGTTGGTAAT    1320
ATTGCTAGCT CGGTGCAAAC TGTAGATGCA TTTGCAGAAC AAATATCTAA ACTAGGTTCA    1380
CATTTACAGA ATGTGAAAGG ATTAGGAGGA TTGAGTAATA AATTACAAAA TCTACCAGAT    1440
CTAGGAAAAG CAAGTTTAGG TTTGACATT ATCTCTGGTT TACTTTCTGG AGCATCTGCA    1500
GGTCTCATTT TAGCAGATAA AGAGGCTTCA ACAGAAAAGA AAGCTGCCGC AGGTGTAGAA    1560
TTTGCTAACC AAATTATAGG TAATGTAACA AAAGCGGTCT CATCTTACAT TCTTGCCCAA    1620
CGAGTCGCTT CAGGTTTGTC TTCAACTGGT CCTGTCGCTG CATTAATCGC ATCTACAGTT    1680
GCACTAGCTG TTAGCCCTCT TTCATTCTTA AATGTAGCTG ATAAGTTTAA ACAAGCTGAT    1740
TTAATCAAAT CATATTCTGA ACGCTTCCAA AAATTAGGAT ATGATGGAGA TCGTTTATTA    1800
GCTGATTTTC ACCGTGAGAC AGGAACTATT GATGCTTCTG TAACAACAAT TAACACTGCT    1860
TTAGCAGCTA TCTCCGGTGG AGTTGGAGCT GCAAGCGCGG GTTCTCTAGT CGGAGCTCCA    1920
GTTGCGTTAC TCGTTGCTGG TGTTACGGGA CTTATTACAA CTATTCTAGA ATATTCTAAA    1980
```

| | | | | | |
|---|---|---|---|---|---|
| CAAGCCATGT | TTGAACATGT | TGCAAATAAG | GTTCATGACA | GAATAGTTGA | ATGGGAGAAA | 2040 |
| AAACATAATA | AAAACTATTT | TGAGCAAGGT | TATGATTCTC | GTCATTTAGC | TGATTTACAA | 2100 |
| GACAATATGA | AGTTTCTTAT | CAATTTAAAT | AAAGAACTTC | AGGCTGAACG | CGTAGTAGCT | 2160 |
| ATTACCCAAC | AAAGATGGGA | TAACCAAATT | GGAGACCTAG | CGGCAATTAG | CCGTAGAACG | 2220 |
| GATAAAATTT | CCAGTGGAAA | AGCTTATGTG | GATGCTTTTG | AGGAGGGGCA | ACACCAGTCC | 2280 |
| TACGATTCAT | CCGTACAGCT | AGATAACAAA | AACGGTATTA | TTAATATTAG | TAATACAAAT | 2340 |
| AGAAAGACAC | AAAGTGTTTT | ATTCAGAACT | CCATTACTAA | CTCCAGGTGA | AGAGAATCGG | 2400 |
| GAACGTATTC | AGGAAGGTAA | AAATTCTTAT | ATTACAAAAT | TACATATACA | AAGAGTTGAC | 2460 |
| AGTTGGACTG | TAACAGATGG | TGATGCTAGC | TCAAGCGTAG | ATTTCACTAA | TGTAGTACAA | 2520 |
| CGAATCGCTG | TGAAATTTGA | TGATGCAGGT | AACATTATAG | AATCTAAAGA | TACTAAAATT | 2580 |
| ATCGCAAATT | TAGGTGCTGG | TAACGATAAT | GTATTTGTTG | GGTCAAGTAC | TACCGTTATT | 2640 |
| GATGGCGGGG | ACGGACATGA | TCGAGTTCAC | TACAGTAGAG | GAGAATATGG | CGCATTAGTT | 2700 |
| ATTGATGCTA | CAGCCGAGAC | AGAAAAAGGC | TCATATTCAG | TAAAACGCTA | TGTCGGAGAC | 2760 |
| AGTAAAGCAT | TACATGAAAC | AATTGCCACC | CACCAAACAA | ATGTTGGTAA | TCGTGAAGAA | 2820 |
| AAAATTGAAT | ATCGTCGTGA | AGATGATCGT | TTTCATACTG | GTTATACTGT | GACGGACTCA | 2880 |
| CTCAAATCAG | TTGAAGAGAT | CATTGGTTCA | CAATTTAATG | ATATTTTCAA | AGGAAGCCAA | 2940 |
| TTTGATGATG | TGTTCCATGG | TGGTAATGGT | GTAGACACTA | TTGATGGTAA | CGATGGTGAC | 3000 |
| GATCATTTAT | TTGGTGGCGC | AGGCGATGAT | GTTATCGATG | GAGGAAACGG | TAACAATTTC | 3060 |
| CTTGTTGGAG | GAACCGGTAA | TGATATTATC | TCGGGAGGTA | AAGATAATGA | TATTTATGTC | 3120 |
| CATAAAACAG | GCGATGGAAA | TGATTCTATT | ACAGACTCTG | GCGGACAAGA | TAAACTGGCA | 3180 |
| TTTTCGGATG | TAAATCTTAA | AGACCTCACC | TTTAAGAAAG | TAGATTCTTC | TCTCGAAATC | 3240 |
| ATTAATCAAA | AAGGAGAAAA | AGTTCGTATT | GGGAATTGGT | TCTTAGAAGA | TGATTTGGCT | 3300 |
| AGCACAGTTG | CTAACTATAA | AGCTACGAAT | GACCGAAAAA | TTGAGGAAAT | TATTGGTAAA | 3360 |
| GGAGGAGAAC | GTATTACATC | AGAACAAGTT | GATAAACTGA | TTAAGGAGGG | TAACAATCAA | 3420 |
| ATCTCTGCAG | AAGCATTATC | CAAAGTTGTG | AATGATTACA | ATACGAGTAA | AGATAGACAG | 3480 |
| AACGTATCTA | ATAGCTTAGC | AAAATTGATT | TCTTCAGTCG | GGAGCTTTAC | GTCTTCCTCA | 3540 |
| GACTTTAGGA | ATAATTTAGG | AACATATGTT | CCTTCATCAA | TAGATGTCTC | GAATAATATT | 3600 |
| CAATTAGCTA | GAGCCGCTTA | ATATTCAAAT | CATAGCAATC | CTATGGTGTA | AATTATAGGA | 3660 |
| TTGTTATTTT | TTTAAAGGAG | AAGTTATGGA | ACCCAATAAA | AATAAGGATC | TTGGTTTAGC | 3720 |
| TGTAGAAAAT | CAAACCTAAT | CTGACAGTTC | CCGTTTAAAA | TTACCGTGTC | TGTCAGATTA | 3780 |
| ATTTGAGCTT | AAATTCTTTT | CTGCCCAAAT | CCGTTTTCCA | TCAAGTAATG | TTGCCATCGG | 3840 |
| TGTTCTGCCA | CAGCACACTT | TTCCTTGATG | TGTTCGATGG | TGATTATAAT | ACATTCATCT | 3900 |
| AAATCAGCTT | GTAATGTCGC | TAAATCCGTA | TATATTTTCT | TCCTAAATGC | GACTTGGTAA | 3960 |
| AATTCTTGTA | AGATAGTCTT | ATGAAAACGT | TCACAGATAC | CATTCGTCTG | TGGATGCTTC | 4020 |
| ACTTTCGTTT | TAGTATGCTC | TATGTCATTT | ATCGCTAAAT | AAAGCTCATA | ATCGTGATTT | 4080 |
| TCCACTTTGC | CACAATATTC | ACTGCCACGG | TCGGTGAGAA | TACGCAACAT | CGGTAATCCT | 4140 |
| TGGGCTTCAA | AGAACGGCAG | TACTTTATGA | TTGAGCATAT | CTGCAGCGGC | AATTGCGGTT | 4200 |
| TTCATTGTGT | AGAGCTTTGC | AAAAGCAACC | TTACTATAAG | TATCAACAAA | TGTTTGCTGA | 4260 |
| TAAATGCGTC | CAACACCTTT | TAAATTACCT | ACATAAAAGG | TATCTTGTGA | ACCTAAATAG | 4320 |
| CCCGGATGAG | CGGTTTCAAT | TTCTCCACTC | GATATATCAT | CCTCTTTCTT | ACGTTCTAGG | 4380 |

```
GCTTGGACTT GACTTTCATT TAGAATAATG CCTTTCTCAG CCACTTCTTT CTCTAGTGCA    4440

TTTAAACGCT GTTTAAAGTT AGTAAGATTA TGACGTAGCC AAATGGAACG AACACCACCG    4500

GCTGAAACAA ACACACCTTG CTTGCGAAGT TCGTTACTCA CTCGAACTTG TCCGTAAGCT    4560

GGAAAATCTA GAGCAAATTT TACAACAGCT TGCTCAATGT GCTCGTCTAC TCGATTTTTG    4620

ATATTCGGTA CCCGACGAGT TTGCTTAAGT AATGCTTCAA CACCGCCTTG CGCTACGGCT    4680

TGTTGATAGC GATAGAATGT ATCTCGGCTC ATTCCCATCG CTTTACAAGC T             4731
```

(2) INFORMATION FOR SEQ ID NO:10:

(i) SEQUENCE CHARACTERISTICS:
        (A) LENGTH: 173 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:10:

```
Met Ser Tyr Lys Asn Val Lys Asn Leu Thr Asp Asp Phe Thr Thr Leu
1               5                   10                  15

Gly His Ile Ala Trp Leu Trp Ala Asn Ser Pro Leu His Lys Glu Trp
            20                  25                  30

Ser Ile Ser Leu Phe Thr Lys Asn Ile Leu Pro Ala Ile Gln His Asp
        35                  40                  45

Gln Tyr Ile Leu Leu Met Arg Asp Glu Phe Pro Val Ala Phe Cys Ser
50                  55                  60

Trp Ala Asn Leu Thr Leu Thr Asn Glu Val Lys Tyr Val Arg Asp Val
65                  70                  75                  80

Thr Ser Leu Thr Phe Glu Asp Trp Asn Ser Gly Glu Arg Lys Trp Leu
                85                  90                  95

Ile Asp Trp Ile Ala Pro Phe Gly Asp Asn Asn Thr Leu Tyr Arg Tyr
            100                 105                 110

Met Arg Lys Lys Phe Pro Asn Glu Val Phe Arg Ala Ile Arg Val Tyr
        115                 120                 125

Pro Gly Ser Thr Glu Ala Lys Ile Ile His Val Gln Gly Gly Gln Ile
130                 135                 140

Asn Lys Phe Thr Ala Lys Lys Leu Ile Gln Gln Tyr Gln Glu Glu Leu
145                 150                 155                 160

Ile Gln Val Leu Asn Asn His Lys Lys Ile Val Arg Gly
                165                 170
```

(2) INFORMATION FOR SEQ ID NO:11:

(i) SEQUENCE CHARACTERISTICS:
        (A) LENGTH: 1049 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:11:

```
Met Ser Thr Trp Ser Ser Met Leu Ala Asp Leu Lys Lys Arg Ala Glu
1               5                   10                  15
```

```
Glu Ala Lys Arg Gln Val Lys Lys Gly Tyr Asp Val Thr Lys Asn Gly
                20                  25                  30

Leu Gln Tyr Gly Val Ser Gln Ala Lys Leu Gln Ala Leu Ala Ala Gly
            35                  40                  45

Lys Ala Val Gln Lys Tyr Gly Asn Lys Leu Val Leu Val Ile Pro Lys
 50                  55                  60

Glu Tyr Asp Gly Ser Val Gly Asn Gly Phe Phe Asp Leu Val Lys Ala
 65                  70                  75                  80

Ala Glu Glu Leu Gly Ile Gln Val Lys Tyr Val Asn Arg Asn Glu Leu
                85                  90                  95

Glu Val Ala His Lys Ser Leu Gly Thr Ala Asp Gln Phe Leu Gly Leu
            100                 105                 110

Thr Glu Arg Gly Leu Thr Leu Phe Ala Pro Gln Leu Asp Gln Phe Leu
        115                 120                 125

Gln Lys His Ser Lys Ile Ser Asn Val Val Gly Ser Ser Thr Gly Asp
130                 135                 140

Ala Val Ser Lys Leu Ala Lys Ser Gln Thr Ile Ile Ser Gly Ile Gln
145                 150                 155                 160

Ser Val Leu Gly Thr Val Leu Ala Gly Ile Asn Leu Asn Glu Ala Ile
                165                 170                 175

Ile Ser Gly Gly Ser Glu Leu Glu Leu Ala Glu Ala Gly Val Ser Leu
            180                 185                 190

Ala Ser Glu Leu Val Ser Asn Ile Ala Lys Gly Thr Thr Thr Ile Asp
        195                 200                 205

Ala Phe Thr Thr Gln Ile Gln Asn Phe Gly Lys Leu Ala Glu Asn Ala
210                 215                 220

Lys Gly Leu Gly Gly Val Gly Arg Gln Leu Gln Asn Ile Ser Gly Ser
225                 230                 235                 240

Ala Leu Ser Lys Thr Gly Leu Gly Leu Asp Ile Ile Ser Ser Leu Leu
                245                 250                 255

Ser Gly Val Thr Arg Ser Phe Ala Leu Arg Asn Lys Asn Ala Ser Thr
            260                 265                 270

Ser Thr Lys Val Ala Ala Gly Phe Glu Leu Ser Asn Gln Val Ile Gly
        275                 280                 285

Gly Ile Thr Lys Ala Val Ser Ser Tyr Ile Leu Ala Gln Arg Leu Arg
290                 295                 300

Ala Gly Leu Ser Thr Thr Gly Pro Ala Ala Leu Ile Ala Ser Ser
305                 310                 315                 320

Ile Ser Leu Ala Ile Ser Pro Leu Ala Phe Leu Arg Val Ala Asp Asn
                325                 330                 335

Phe Asn Arg Ser Lys Glu Ile Gly Glu Phe Ala Glu Arg Phe Lys Lys
            340                 345                 350

Leu Gly Tyr Asp Gly Asp Lys Leu Leu Ser Glu Phe Tyr His Glu Ala
        355                 360                 365

Gly Thr Ile Asp Ala Ser Ile Thr Thr Ile Ser Thr Ala Leu Ser Ala
370                 375                 380

Ile Ala Ala Gly Thr Ala Ala Ser Ala Gly Ala Leu Val Gly Ala
385                 390                 395                 400

Pro Ile Thr Leu Leu Val Thr Gly Ile Thr Gly Leu Ile Ser Gly Ile
                405                 410                 415

Leu Glu Phe Ser Lys Gln Pro Met Leu Asp His Val Ala Ser Lys Ile
            420                 425                 430

Gly Asn Lys Ile Asp Glu Trp Glu Lys Lys Tyr Gly Lys Asn Tyr Phe
```

|     | 435 |     |     |     | 440 |     |     |     | 445 |     |     |
| --- | --- | --- | --- | --- | --- | --- | --- | --- | --- | --- | --- |

Glu Asn Gly Tyr Asp Ala Arg His Lys Ala Phe Leu Glu Asp Ser Phe
450                     455                     460

Ser Leu Leu Ser Ser Phe Asn Lys Gln Tyr Glu Thr Glu Arg Ala Val
465                     470                     475                     480

Leu Ile Thr Gln Gln Arg Trp Asp Glu Tyr Ile Gly Glu Leu Ala Gly
                        485                     490                     495

Ile Thr Gly Lys Gly Asp Lys Leu Ser Ser Gly Lys Ala Tyr Val Asp
                500                     505                     510

Tyr Phe Gln Glu Gly Lys Leu Leu Glu Lys Lys Pro Asp Asp Phe Ser
                515                     520                     525

Lys Val Val Phe Asp Pro Thr Lys Gly Glu Ile Asp Ile Ser Asn Ser
530                     535                     540

Gln Thr Ser Thr Leu Leu Lys Phe Val Thr Pro Leu Leu Thr Pro Gly
545                     550                     555                     560

Thr Glu Ser Arg Glu Arg Thr Gln Thr Gly Lys Tyr Glu Tyr Ile Thr
                565                     570                     575

Lys Leu Val Val Lys Gly Lys Asp Lys Trp Val Val Asn Gly Val Lys
                580                     585                     590

Asp Lys Gly Ala Val Tyr Asp Tyr Thr Asn Leu Ile Gln His Ala His
                595                     600                     605

Ile Ser Ser Val Ala Arg Gly Glu Glu Tyr Arg Glu Val Arg Leu
610                     615                     620

Val Ser His Leu Gly Asn Gly Asn Asp Lys Val Phe Leu Ala Ala Gly
625                     630                     635                     640

Ser Ala Glu Ile His Ala Gly Glu Gly His Asp Val Val Tyr Tyr Asp
                645                     650                     655

Lys Thr Asp Thr Gly Leu Leu Val Ile Asp Gly Thr Lys Ala Thr Glu
                660                     665                     670

Gln Gly Arg Tyr Ser Val Thr Arg Glu Leu Ser Gly Ala Thr Lys Ile
                675                     680                     685

Leu Arg Glu Val Ile Lys Asn Gln Lys Tyr Ala Val Gly Lys Arg Glu
                690                     695                     700

Glu Thr Leu Glu Tyr Arg Asp Tyr Glu Leu Thr Gln Ser Gly Asn Ser
705                     710                     715                     720

Asn Leu Lys Ala His Asp Glu Leu His Ser Val Glu Glu Ile Gly Ser
                725                     730                     735

Asn Gln Arg Asp Glu Phe Lys Gly Ser Lys Phe Arg Asp Ile Phe His
                740                     745                     750

Gly Ala Asp Gly Asp Asp Leu Leu Asn Gly Asn Asp Gly Asp Asp Ile
                755                     760                     765

Leu Tyr Gly Asp Lys Gly Asn Asp Glu Leu Arg Gly Asp Asn Gly Asn
770                     775                     780

Asp Gln Leu Tyr Gly Gly Glu Gly Asp Asp Lys Leu Leu Gly Gly Asn
785                     790                     795                     800

Gly Asn Asn Tyr Leu Ser Gly Gly Asp Gly Asn Asp Glu Leu Gln Val
                805                     810                     815

Leu Gly Asn Gly Phe Asn Val Leu Arg Gly Gly Lys Gly Asp Asp Lys
                820                     825                     830

Leu Tyr Gly Ser Ser Gly Ser Asp Leu Leu Asp Gly Gly Glu Gly Asn
                835                     840                     845

Asp Tyr Leu Glu Gly Gly Asp Gly Ser Asp Phe Tyr Val Tyr Arg Ser
850                     855                     860

-continued

```
Thr Ser Gly Asn His Thr Ile Tyr Asp Gln Gly Lys Ala Ser Asp Ser
865                 870                 875                 880

Asp Lys Leu Tyr Leu Ser Asp Leu Ser Phe Asp Asn Ile Leu Val Lys
                885                 890                 895

Arg Val Asn Asp Asn Leu Glu Phe Arg Ser Asn Asn Ser Asn Ser
            900                 905                 910

Gly Val Leu Thr Ile Lys Asp Trp Phe Lys Gly Gly Asn Ser Tyr Asn
        915                 920                 925

His Lys Ile Glu Gln Ile Val Asp Lys Asn Gly Arg Lys Leu Thr Ala
    930                 935                 940

Gly Asn Leu Gly Asn Asn Phe His Asp Thr Gln Gln Ala Ser Ser Leu
945                 950                 955                 960

Leu Lys Asn Val Thr Gln Glu Gln Asn Glu Ser Asn Leu Ser Ser Leu
                965                 970                 975

Lys Thr Glu Leu Gly Lys Ile Ile Thr Asn Ala Gly Asn Phe Gly Val
            980                 985                 990

Ala Lys Gln Gly Asn Thr Gly Ile Asn Thr Ala Leu Asn Asn Glu
        995                 1000                1005

Val Asn Lys Ile Ile Ser Ser Ala Asn Thr Phe Ala Thr Ser Gln Leu
    1010                1015                1020

Gly Gly Ser Gly Met Gly Thr Leu Pro Ser Thr Asn Val Asn Ser Met
1025                1030                1035                1040

Met Leu Gly Asn Leu Ala Arg Ala Ala
            1045
```

(2) INFORMATION FOR SEQ ID NO:12:

(i) SEQUENCE CHARACTERISTICS:
        (A) LENGTH: 711 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:12:

```
Met Glu Ser Gln Met Pro Phe Asn Glu Lys Ile Asp Tyr Gly Leu His
1                   5                   10                  15

Ala Leu Val Ile Leu Ala Gln Tyr His Asn Val Ala Val Asn Pro Glu
                20                  25                  30

Glu Val Lys His Lys Phe Asp Leu Asp Gly Lys Gly Leu Asp Leu Val
            35                  40                  45

Ala Trp Leu Leu Ala Ala Lys Ser Leu Glu Leu Lys Val Lys Arg Val
50                  55                  60

Lys Lys Ser Ile Glu Arg Leu Pro Phe Ile His Leu Pro Ala Leu Ile
65                  70                  75                  80

Trp Arg Asp Asp Gly Gln His Val Ile Leu Met Lys Ile Asp Thr Gln
                85                  90                  95

Thr Asn Arg Tyr Leu Ile Phe Asp Leu Glu Glu Arg Asn Pro Lys Val
            100                 105                 110

Leu Ser Ala Ala Glu Phe His Glu Ile Phe Gln Gly Met Ile Leu
        115                 120                 125

Ile Thr Ser Arg Ala Ser Ile Met Gly Gln Leu Ala Lys Phe Asp Phe
    130                 135                 140

Thr Trp Phe Ile Pro Ala Val Ile Lys Tyr Arg Lys Ile Phe Val Glu
```

-continued

```
                145                 150                 155                 160
Thr Ile Ile Val Ser Ile Phe Leu Gln Leu Phe Ala Leu Ile Thr Pro
                    165                 170                 175
Leu Phe Phe Gln Val Val Met Asp Lys Val Leu Val His Arg Gly Phe
                180                 185                 190
Ser Thr Leu Asn Val Ile Thr Val Ala Leu Ser Val Val Val Ile Phe
                195                 200                 205
Glu Ile Val Leu Ser Gly Leu Arg Thr Tyr Ile Phe Ser His Ser Thr
            210                 215                 220
Ser Arg Ile Asp Val Glu Leu Gly Ala Lys Leu Phe Arg His Leu Leu
225                 230                 235                 240
Ala Leu Pro Ile Ser Tyr Phe Glu Asn Arg Arg Val Gly Asp Thr Val
                    245                 250                 255
Ala Arg Val Arg Glu Leu Asp Gln Ile Arg Asn Phe Leu Thr Gly Gln
                260                 265                 270
Ala Leu Thr Ser Val Leu Asp Leu Leu Phe Ser Phe Ile Phe Phe Ala
                275                 280                 285
Val Met Trp Tyr Tyr Ser Pro Lys Leu Thr Ile Val Ile Leu Leu Ser
            290                 295                 300
Leu Pro Cys Tyr Ile Ala Trp Ser Ile Phe Ile Ser Pro Ile Leu Arg
305                 310                 315                 320
Arg Arg Leu Asp Glu Lys Phe Ala Arg Asn Ala Asp Asn Gln Ser Phe
                    325                 330                 335
Leu Val Glu Ser Val Ser Ala Ile Asp Thr Ile Lys Ala Leu Ala Val
                340                 345                 350
Thr Pro Gln Met Thr Asn Ile Trp Asp Lys Gln Leu Ala Ser Tyr Val
                355                 360                 365
Ser Ala Asp Phe Arg Val Thr Val Leu Ala Thr Ile Gly Gln Gln Gly
            370                 375                 380
Val Gln Leu Ile Gln Lys Thr Val Met Ile Ile Asn Leu Trp Leu Gly
385                 390                 395                 400
Ala His Leu Val Ile Ser Gly Asp Leu Ser Ile Gly Gln Leu Ile Thr
                    405                 410                 415
Phe Asn Met Leu Ser Gly Gln Val Ile Ala Pro Val Val Arg Leu Ala
                420                 425                 430
Gln Leu Trp Gln Asp Phe Gln Gln Val Gly Ile Ser Ile Thr Arg Leu
                435                 440                 445
Gly Asp Val Leu Asn Ser Pro Thr Glu Asn Tyr Gln Gly Lys Leu Ser
            450                 455                 460
Leu Pro Glu Ile Phe Gly Asp Ile Ala Phe Lys His Ile Arg Phe Arg
465                 470                 475                 480
Tyr Lys Pro Asp Ala Pro Ile Ile Leu Asp Asp Val Asn Leu Ser Val
                    485                 490                 495
Lys Gln Gly Glu Val Ile Gly Ile Val Gly Arg Ser Gly Ser Gly Lys
                500                 505                 510
Ser Thr Leu Thr Lys Leu Leu Gln Arg Phe Tyr Ile Pro Glu Asn Gly
                515                 520                 525
Gln Val Leu Ile Asp Gly His Asp Leu Ala Leu Ala Asp Pro Asn Trp
            530                 535                 540
Leu Arg Arg Gln Ile Gly Val Val Leu Gln Asp Asn Val Leu Leu Asn
545                 550                 555                 560
Arg Ser Ile Arg Asp Asn Ile Ala Leu Thr Asp Pro Ser Met Ser Met
                    565                 570                 575
```

```
Glu Arg Val Ile Tyr Ala Ala Lys Leu Ala Gly Ala His Asp Phe Ile
            580                 585                 590

Ser Glu Leu Arg Glu Gly Tyr Asn Thr Ile Val Gly Glu Leu Gly Ala
            595                 600                 605

Gly Leu Ser Gly Gly Gln Arg Gln Arg Ile Ala Ile Ala Arg Ala Leu
            610                 615                 620

Val Asn Asn Pro Arg Ile Leu Ile Phe Asp Glu Ala Thr Ser Ala Leu
625                 630                 635                 640

Asp Tyr Glu Ser Glu His Ile Ile Met Gln Asn Met Gln Lys Ile Cys
            645                 650                 655

His Gly Arg Thr Val Ile Ile Ile Ala His Arg Leu Ser Thr Val Lys
            660                 665                 670

Asn Ala Asp Arg Ile Ile Val Met Glu Lys Gly His Ile Val Glu Gln
            675                 680                 685

Gly Lys His Asn Gln Leu Leu Glu Asn Glu Asn Gly Leu Tyr Tyr Tyr
            690                 695                 700

Leu Asn Gln Leu Gln Ser Asn
705                 710

(2) INFORMATION FOR SEQ ID NO:13:

(i) SEQUENCE CHARACTERISTICS:
        (A) LENGTH: 477 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Actinobacillus pleuropneumoniae (xi) SEQUENCE DESCRIPTION: SEQ ID NO:13:

Met Lys Leu Trp Ile Leu Gly Leu Gly Glu Phe Phe Gln Arg Tyr Arg
1               5                   10                  15

Asn Ile Trp Arg Glu Ile Trp Lys Ile Arg Lys Gln Leu Asp Thr Pro
            20                  25                  30

Ala Arg Gln Lys Asp Glu Asn Glu Phe Leu Pro Arg His Leu Glu Leu
            35                  40                  45

Ile Glu Thr Pro Ile Ser Lys Lys Pro Arg Leu Ile Ala Tyr Leu Ile
50                  55                  60

Met Leu Phe Leu Phe Leu Ala Ile Val Ile Ser Ile Ile Ser Lys Val
65                  70                  75                  80

Glu Ile Val Ala Ser Ala Thr Gly Lys Leu Val Phe Ser Gly His Ser
            85                  90                  95

Lys Glu Ile Lys Pro Ile Glu Asn Ala Leu Val Lys Asp Ile Phe Val
            100                 105                 110

Lys Asp Gly Gln Phe Val Glu Lys Gly Gln Leu Leu Leu Asn Leu Thr
            115                 120                 125

Ala Leu Gly Cys Asp Ala Asp Lys Gln Lys Thr Lys Val Ser Leu Gly
            130                 135                 140

Leu Glu Arg Leu Asp Gly Tyr Arg Tyr Lys Ser Leu Leu Tyr Ser Ile
145                 150                 155                 160

Glu His Asn Arg Leu Pro Leu Leu Asp Phe Asn Gln Ala Asp Phe Asp
            165                 170                 175

Ser Val Gln Glu Glu Asp Lys Thr Gly Ala Arg His Leu Ile Thr Glu
            180                 185                 190

Gln Phe Glu Thr Trp Gln Lys Gln Lys Tyr Gln Lys Glu Leu Ala Tyr
```

-continued

```
        195                 200                 205

Gln Arg Lys Gln Ala Glu Lys Gln Thr Val Leu Ala Asn Ile Arg Lys
    210                 215                 220

Tyr Glu Ser Ala Ser Arg Ile Glu Lys Glu Lys Leu Ser Asp Leu Lys
225                 230                 235                 240

Lys Leu Tyr Asp Val Lys Ser Ile Ser Lys His Glu Leu Leu Ala Gln
                245                 250                 255

Glu Asn Arg Tyr Val Glu Ala Ser Asn Glu Leu Ser Val Tyr Gln Ser
            260                 265                 270

His Leu Lys Glu Val Glu Ser Asp Leu Leu Lys Ala Gln Glu Asp Leu
        275                 280                 285

Lys Leu Val Thr Gln Leu Phe Lys Ser Asp Ile Leu Glu Lys Leu Gln
    290                 295                 300

Gln Asn Ile Gln Arg Glu Lys Gln Leu Thr Leu Glu Leu Glu Lys Asn
305                 310                 315                 320

Glu Gln Arg Gln Leu Ala Ser Ile Ile Arg Ala Pro Val Ser Gly Thr
                325                 330                 335

Val Gln Gln Leu Lys Thr His Thr Lys Gly Gly Val Val Thr Thr Ala
            340                 345                 350

Glu Thr Leu Met Val Ile Ala Pro Glu Asp Asp Val Leu Glu Val Ser
        355                 360                 365

Ala Leu Ile Gln Asn Lys Asp Val Gly Phe Val Glu Ile Gly Gln Glu
    370                 375                 380

Ala Val Ile Lys Val Glu Thr Phe Pro Tyr Thr Arg Tyr Gly Tyr Leu
385                 390                 395                 400

Tyr Gly Lys Val Lys Thr Ile Thr Leu Asp Ala Ile Glu His Pro Gln
                405                 410                 415

Leu Gly Leu Val Phe Asn Ser Ile Ile Glu Ile Asn Lys Lys Thr Leu
            420                 425                 430

Thr Asp Gly Asp Lys Glu Ile Gln Leu Gly Ser Gly Met Ser Val Ile
        435                 440                 445

Ala Glu Ile Lys Thr Gly Glu Arg Ser Val Ile Ser Phe Leu Leu Ser
    450                 455                 460

Pro Leu Glu Glu Ser Ile Thr Glu Ser Leu Arg Glu Arg
465                 470                 475
```

(2) INFORMATION FOR SEQ ID NO:14:

(i) SEQUENCE CHARACTERISTICS:
(A) LENGTH: 7721 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Actinobacillus pleuropneumoniae (xi) SEQUENCE DESCRIPTION: SEQ ID NO:14:

```
TCTTGAATAA TAGTTGGTTT TGTAGATATT CTTTTAATAT CAAACAACTA TTGTTATTTG     60

TCTGAGTGTA GATATGTAGC ATTGTGTATT TCTTTATTTA CAACTCTAAT CTTAATCTAA    120

AAAGATTTCT ATATTTTCTT TGTAAGAAAT TTTGTTAAAA TCCGACTAAC TATATAATTA    180

ACGGTTCTTA AAGTGGATAA ATAATAAAAT TATGAGTTAT AAAAATGTTA AAAATTTAAC    240

AGATGATTTT ACAACTTTAG GGCATATCGC TTGGTTGTGG GCTAATTCTC CGTTACATAA    300

GGAGTGGTCT ATCTCTTTGT TTACTAAGAA TATTTTGCCA GCCATTCAAC ATGATCAATA    360
```

```
TATTTTACTT ATGCGAGATG AGTTCCCTGT AGCGTTTTGT AGTTGGGCAA ATTTAACGTT      420

AACTAATGAA GTGAAGTATG TACGTGATGT GACGTCATTG ACTTTTGAAG ATTGGAATTC      480

AGGAGAACGA AAATGGTTGA TCGATTGGAT TGCGCCATTT GGGGATAACA ATACGCTTTA      540

TAGATATATG CGTAAAAAAT TTCCTAATGA AGTATTCCGG GCCATTCGAG TATATCCTGG      600

TTCTACAGAA GCGAAAATCA TTCATGTTCA AGGAGGACAA ATTAATAAAT TTACAGCTAA      660

AAAATTAATA CAACAATATC AGGAAGAACT TATTCAAGTT CTTAACAATC ACAAAAAAAT      720

TGTAAGAGGA TAAAATATGA GTACTTGGTC AAGCATGTTA GCCGACTTAA AAAAAAGGGC      780

TGAAGAAGCC AAAAGACAAG TTAAAAAAGG CTACGATGTA ACTAAAAATG GTTTGCAATA      840

TGGGGTGAGT CAAGCAAAAT TACAAGCATT AGCAGCTGGT AAAGCCGTTC AAAAGTACGG      900

TAATAAATTA GTTTTAGTTA TTCCAAAAGA GTATGACGGA AGTGTTGGTA ACGGTTTCTT      960

TGATTTAGTA AAAGCAGCTG AGGAATTAGG CATTCAAGTT AAATATGTTA ACCGTAATGA     1020

ATTGGAAGTT GCCCATAAAA GTTAGGTAC CGCAGACCAA TTCTTGGGTT TAACAGAACG     1080

TGGACTTACT TTATTTGCAC CGCAACTAGA TCAGTTCTTA CAAAAACATT CAAAAATTTC     1140

TAACGTAGTG GGCAGTTCTA CTGGTGATGC AGTAAGTAAA CTTGCTAAGA GTCAAACTAT     1200

TATTTCAGGA ATTCAATCTG TATTAGGTAC TGTATTAGCA GGTATTAATC TTAATGAAGC     1260

TATTATTAGT GGCGGTTCAG AGCTCGAATT AGCTGAAGCT GGTGTTTCTT TAGCCTCTGA     1320

GCTCGTTAGC AATATTGCTA AAGGTACAAC AACAATAGAT GCTTTCACTA CACAAATCCA     1380

GAACTTTGGG AAATTAGCGG AAAATGCTAA AGGGTTAGGT GGTGTTGGCC GCCAATTACA     1440

GAATATTTCA GGTTCTGCAT TAAGCAAAAC TGGATTAGGT TTGGATATTA TCTCAAGCTT     1500

ACTTTCAGGA GTAACTCGAA GTTTTGCTTT ACGGAATAAG AATGCTTCAA CAAGCACTAA     1560

AGTTGCTGCT GGCTTTGAAC TCTCAAATCA GTAATTGGT GGTATTACGA AGCAGTATC     1620

AAGCTATATT CTTGCACAGC GTTACGTGC TGGTTTATCA ACGACAGGTC CTGCTGCAGC     1680

ACTAATTGCG TCTAGTATTT CTTTAGCAAT CAGTCCATTG GCGTTTTTAC GTGTAGCTGA     1740

TAATTTTAAT CGTTCTAAAG AAATTGGCGA ATTTGCTGAA CGTTTCAAAA AATTGGGCTA     1800

TGACGGCGAT AAAACTACTTT CAGAGTTTTA TCACGAAGCT GGTACTATTG ATGCCTCAAT     1860

TACTACAATT AGTACAGCAC TTTCTGCTAT CGCAGCTGGA ACGGCCGCCG CGAGTGCAGG     1920

TGCATTAGTT GGCGCACCAA TTACTTTGTT GGTTACTGGT ATCACAGGAT TAATTTCTGG     1980

TATTTTAGAG TTCTCTAAAC AACCAATGTT AGATCATGTT GCATCGAAAA TTGGTAACAA     2040

AATTGACGAA TGGGAGAAAA AATACGGTAA AAATTACTTC GAGAATGGCT ATGATGCTCG     2100

TCATAAAGCT TTCTTAGAAG ATTCATTCTC ATTATTGTCT AGTTTTAATA AACAATATGA     2160

AACTGAAAGA GCTGTTTTAA TTACACAACA ACGTTGGGAT GAATATATTG GCGAACTTGC     2220

GGGTATTACT GGTAAAGGTG ACAAACTCTC TAGTGGTAAG GCGTATGTAG ATTACTTTCA     2280

AGAAGGTAAA TTATTAGAGA AAAAACCTGA TGACTTTAGC AAAGTAGTTT TCGATCCAAC     2340

TAAGGGCGAA ATTGATATTT CAAATAGCCA AACGTCAACG TTGTTAAAAT TTGTTACGCC     2400

ATTATTAACA CCAGGTACAG AGTCACGTGA AGAACTCAA ACAGGTAAAT ATGAATATAT     2460

CACGAAGTTA GTTGTAAAAG GTAAAGATAA ATGGGTTGTT AATGGCGTTA AAGATAAAGG     2520

TGCCGTTTAT GATTATACTA ATTTAATTCA ACATGCTCAT ATTAGTTCAT CAGTAGCACG     2580

TGGTGAAGAA TACCGTGAAG TTCGTTTGGT ATCTCATCTA GGCAATGGTA ATGACAAAGT     2640

GTTCTTAGCT GCGGGTTCCG CAGAAATTCA CGCTGGTGAA GGTCATGATG TGGTTTATTA     2700

TGATAAAACC GATACAGGTC TTTTAGTAAT TGATGGAACC AAAGCGACTG AACAAGGGCG     2760
```

```
TTATTCTGTT ACGCGCGAAT TGAGTGGTGC TACAAAAATC CTGAGAGAAG TAATAAAAAA    2820

TCAAAAATAT GCTGTTGGTA AACGTGAAGA AACCTTGGAA TATCGTGATT ATGAATTAAC    2880

GCAATCAGGT AATAGTAACC TAAAAGCACA TGATGAATTA CATTCAGTAG AAGAAATTGG    2940

AAGTAATCAG AGAGACGAAT TTAAAGGTAG TAAATTCAGA GATATTTTCC ATGGTGCCGA    3000

TGGTGATGAT CTATTAAATG GTAATGATGG GGATGATATT CTATACGGTG ATAAAGGTAA    3060

CGATGAGTTA AGAGGTGATA ACGGTAACGA CCAACTTTAT GGTGGTGAAG GTGATGACAA    3120

ACTATTAGGA GGTAATGGCA ATAATTACCT CAGTGGTGGT GATGGCAATG ATGAGCTTCA    3180

AGTATTAGGC AATGGTTTTA ATGTGCTTCG TGGCGGTAAA GGCGATGATA AACTTTATGG    3240

TAGCTCAGGT TCTGATTTAC TTGATGGTGG AGAAGGTAAT GATTATCTAG AAGGAGGCGA    3300

TGGTAGCGAT TTTTATGTTT ATCGTTCCAC TTCAGGTAAT CATACTATTT ATGATCAAGG    3360

TAAAGCTAGC GATTCAGATA AGCTATATTT GTCAGATCTT TCTTTTGATA ATATTTTAGT    3420

TAAAAGGGTT AACGATAACC TTGAGTTTAG AAGCAATAAT AACAGTAATA GTGGTGTGCT    3480

TACGATCAAG GACTGGTTCA AAGGCGGCAA TAGTTACAAT CATAAAATTG AACAAATTGT    3540

TGATAAAAAT GGTAGAAAAT TGACAGCTGG GAATTTAGGA ATAACTTCC ATGATACTCA     3600

ACAAGCTAGT AGTTTACTTA AAAATGTTAC ACAAGAACAA AATGAAAGCA ATTTATCTTC    3660

ACTTAAAACT GAATTAGGTA AAATTATTAC TAATGCAGGT AATTTTGGTG TGGCAAAACA    3720

AGGTAATACT GGAATCAATA CAGCTGCCTT GAACAATGAA GTGAATAAAA TCATTTCTTC    3780

TGCTAATACC TTTGCTACTT CACAATTGGG TGGCTCAGGG ATGGGAACAT TACCATCAAC    3840

GAATGTAAAT TCAATGATGC TAGGTAACCT AGCTAGAGCA GCTTAATCAT CTGCAATAAT    3900

CAATAGCAAT CCTATGGTTA TTCTAGGATT GCTATTTTAT TTATGGAGTC ACAAATGCCT    3960

TTTAACGAAA AAATAGATTA CGGATTACAT GCATTGGTAA TTCTCGCGCA ATATCACAAT    4020

GTTGCCGTAA ACCCTGAAGA GGTAAAACAT AAATTTGATC TTGATGGCAA AGGATTGGAT    4080

CTTGTTGCTT GGTTATTAGC AGCAAAATCA TTAGAATTAA AAGTCAAACG AGTAAAAAAG    4140

AGTATTGAGC GTTTACCATT TATTCATCTT CCTGCTTTAA TCTGGCGAGA TGATGGTCAA    4200

CACGTTATTT TGATGAAAAT TGACACCCAA ACTAACCGTT ACCTTATTTT TGACTTAGAA    4260

GAACGAAACC CTAAAGTACT AAGTGCGGCT GAATTTCACG AAATTTTTCA AGGTGGTATG    4320

ATTCTTATTA CTTCACGAGC TTCTATTATG GGGCAATTGG CGAAGTTTGA TTTCACTTGG    4380

TTTATCCCCG CAGTAATTAA ATACCGTAAA ATTTTTGTAG AAACTATTAT TGTTTCTATT    4440

TTTTTGCAGC TTTTTGCACT AATTACTCCC TTATTTTTCC AAGTTGTGAT GGATAAAGTT    4500

CTTGTCCATC GTGGATTTTC TACACTTAAT GTTATCACGG TTGCATTATC TGTAGTGGTT    4560

ATCTTTGAAA TTGTATTAAG CGGTCTACGG ACTTATATAT TTTCCCATAG CACTAGCCGA    4620

ATTGATGTAG AACTTGGTGC AAAATTATTT CGTCACTTGT TAGCGTTACC TATTTCTTAT    4680

TTCGAAAATA GACGTGTAGG TGACACAGTT GCTCGAGTAC GAGAATTGGA TCAAATACGC    4740

AATTTTTTAA CAGGTCAGGC ACTTACCTCT GTATTAGATC TCTTATTCTC TTTTATTTTC    4800

TTTGCAGTGA TGTGGTATTA CAGCCCAAAA CTAACTATTG TGATTTTACT TCATTACCT     4860

TGTTATATCG CATGGTCAAT ATTTATTAGC CCAATATTAC GTCGTCGTCT AGATGAAAAA    4920

TTTGCTCGTA ATGCTGATAA TCAATCTTTT TTAGTTGAAT CTGTTTCTGC AATAGACACG    4980

ATCAAGGCTC TTGCTGTAAC ACCTCAAATG ACAAATATTT GGGATAAACA GTTAGCAAGT    5040

TATGTATCAG CAGATTTTAG AGTGACAGTA TTGGCAACTA TTGGACAGCA AGGTGTACAA    5100

CTTATCCAAA AAACAGTAAT GATAATTAAT TTATGGTTAG GTGCACATTT AGTAATTTCA    5160
```

```
GGGGATCTTA GCATTGGACA ATTAATTACT TTTAATATGC TTTCAGGACA AGTTATTGCA       5220

CCTGTAGTTC GTTTAGCACA ATTGTGGCAA GACTTTCAAC AAGTAGGAAT TTCTATTACA       5280

CGATTGGGAG ATGTCTTAAA TTCACCTACA GAAAATTATC AAGGTAAGCT TTCACTACCA       5340

GAAATCTTTG GGGATATCGC ATTTAAACAT ATTCGCTTTC GCTATAAGCC CGATGCTCCA       5400

ATCATTTTAG ATGATGTAAA TTTATCGGTT AAACAGGGGG AAGTTATTGG GATAGTAGGA       5460

CGTTCAGGTT CAGGTAAAAG TACTCTCACT AAATTATTAC AACGTTTTTA TATTCCGGAA       5520

AATGGCCAAG TATTGATTGA TGGTCACGAT CTTGCGCTTG CTGATCCTAA TTGGTTACGT       5580

CGTCAAATTG GTGTTGTTTT ACAAGATAAT GTGTTATTAA ACCGTAGTAT TCGCGATAAT       5640

ATCGCACTCA CTGATCCAAG CATGTCTATG GAACGTGTTA TCTATGCGGC AAAATTAGCA       5700

GGGGCACATG ATTTTATTTC TGAATTACGT GAAGGTTACA ATACTATTGT AGGAGAGCTT       5760

GGTGCAGGCT TATCTGGTGG ACAACGTCAA CGGATTGCTA TTGCACGAGC TTTAGTCAAT       5820

AACCCTAGGA TTTTGATTTT TGATGAGGCG ACAAGTGCAT TAGATTATGA ATCTGAACAT       5880

ATCATTATGC AAAATATGCA AAAAATCTGC CATGGACGGA CAGTAATCAT TATTGCCCAC       5940

CGTCTTTCTA CAGTAAAAAA TGCGGATCGC ATTATTGTTA TGGAAAAGGG ACATATTGTA       6000

GAGCAAGGTA AACATAACCA ATTACTGGAA AATGAAAATG GACTCTATTA TTACCTCAAC       6060

CAACTACAAT CAAATTAAGG TGAAACAACA TGAAGTTATG GATTCTAGGA CTTGGGGAAT       6120

TTTTTCAACG TTATCGTAAT ATTTGGCGTG AAATATGGAA AATCCGCAAA CAATTAGATA       6180

CCCCAGCAAG ACAAAAGAT GAAAACGAAT TTTTGCCTCG GCATTTAGAG TTAATTGAGA        6240

CACCTATTTC AAAAAAGCCA CGGCTGATCG CTTATTTGAT AATGCTATTT CTATTTTTAG       6300

CTATTGTAAT TTCCATTATT AGTAAAGTAG AAATTGTTGC TAGTGCTACA GGTAAGTTGG       6360

TATTTAGTGG ACATAGTAAA GAAATAAAGC CTATTGAGAA TGCTTTAGTA AAAGACATTT       6420

TTGTTAAAGA TGGACAATTT GTTGAAAAAG GACAATTATT ATTAAATCTC ACCGCACTTG       6480

GCTGCGATGC AGACAAACAA AAAACTAAAG TATCGTTAGG ATTGGAAAGA TTAGATGGTT       6540

ACCGATATAA GTCATTGTTA TATAGCATTG AACACAATAG ATTACCTTTA TTGGATTTTA       6600

ACCAAGCTGA TTTTGATTCT GTTCAGGAAG AAGATAAGAC TGGCGCACGT CATTTAATTA       6660

CCGAACAATT TGAGACTTGG CAAAAACAAA AATATCAGAA GGAATTAGCG TATCAACGTA       6720

AACAAGCTGA AAAACAAACA GTATTAGCAA ATATCCGTAA ATATGAAAGC GCTAGTCGTA       6780

TTGAAAAGGA GAAATTAAGT GATTTAAAAA AATTATATGA TGTAAAGTCT ATTTCTAAGC       6840

ATGAGTTGTT AGCACAAGAA AATAGATATG TTGAAGCTAG TAATGAATTG TCTGTTTATC       6900

AATCTCATCT CAAAGAAGTA GAAAGTGACT TGCTTAAAGC ACAAGAAGAT TTAAAGCTTG       6960

TTACTCAATT ATTTAAGAGT GATATTTTGG AAAAACTACA GCAAAATATA CAACGCGAAA       7020

AGCAGCTCAC TTTAGAACTT GAGAAAAATG AACAACGTCA ATTAGCCTCT ATCATTAGGG       7080

CGCCAGTATC AGGCACAGTC CAACAATTAA AAACTCATAC TAAAGGTGGC GTAGTAACTA       7140

CTGCAGAAAC CTTAATGGTC ATTGCTCCTG AGGATGACGT GTTGGAAGTA AGTGCTTTAA       7200

TTCAAAACAA AGATGTTGGT TTTGTTGAAA TTGGACAGGA AGCAGTTATT AAAGTGGAAA       7260

CTTTTCCCTA CACAAGATAT GGTTATCTCT ATGGAAAAGT AAAAACTATT ACTCTTGATG       7320

CTATTGAGCA CCCTCAGCTT GGTTTAGTTT TCAATTCTAT TATTGAGATT AACAAGAAAA       7380

CATTAACAGA TGGTGATAAA GAATTCAAT TAGGTTCTGG AATGAGCGTT ATTGCAGAAA        7440

TTAAAACAGG AGAACGCAGT GTTATCAGTT TCCTACTCAG TCCATTAGAA GAATCTATTA       7500

CTGAAAGTCT AAGAGAACGT TAATTATCTC TTCTAAATTA AGCAAATATA TAACTTTTGT       7560
```

```
AAAAACGTTA TTTAAGGAGA GTTGCTAATA GAAGTTAAAA TATCTATTAG CAACTATATT    7620

ATCTCTTTGA GCTATTTTTA GCTTCTTTAG AAGTTAGAGA TTTTTAGATA TTCATAATAT    7680

ATGAAACTAT TTGCTGATCT AATTTAAAAC TAAAATCTAG A                        7721
```